US008877171B2

(12) United States Patent
Licha et al.

(10) Patent No.: US 8,877,171 B2
(45) Date of Patent: Nov. 4, 2014

(54) POLYANIONIC MULTIVALENT MACROMOLECULES FOR INTRACELLULAR TARGETING OF PROLIFERATION AND PROTEIN SYNTHESIS

(75) Inventors: Kai Licha, Falkensee (DE); Michael Schirner, Berlin (DE); Pia Welker, Berlin (DE); Rainer Haag, Berlin (DE); Marie Weinhart, Berlin (DE); Florian Paulus, Berlin (DE)

(73) Assignee: Mivenion GmbH, Berlin (DE)

( * ) Notice: Subject to any disclaimer, the term of this patent is extended or adjusted under 35 U.S.C. 154(b) by 0 days.

(21) Appl. No.: 13/576,779

(22) PCT Filed: Jan. 31, 2011

(86) PCT No.: PCT/EP2011/000425
§ 371 (c)(1),
(2), (4) Date: Oct. 22, 2012

(87) PCT Pub. No.: WO2011/095311
PCT Pub. Date: Aug. 11, 2011

(65) Prior Publication Data
US 2013/0095035 A1 Apr. 18, 2013

(30) Foreign Application Priority Data

Feb. 3, 2010 (EP) .................................... 10001104
Feb. 18, 2010 (EP) .................................... 10001655
Mar. 2, 2010 (EP) .................................... 10002121

(51) Int. Cl.
*A61K 31/74* (2006.01)
*C08G 83/00* (2006.01)
(Continued)

(52) U.S. Cl.
CPC ............ *C07D 487/22* (2013.01); *C08G 83/003* (2013.01); *A61K 49/0041* (2013.01); *A61K*
(Continued)

(58) Field of Classification Search
None
See application file for complete search history.

(56) References Cited

U.S. PATENT DOCUMENTS 5,474,765 A 12/1995 Thorpe
5,762,918 A 6/1998 Thorpe
(Continued)

FOREIGN PATENT DOCUMENTS

| WO | WO-93 18793 | 9/1993 |
| WO | WO-2008 015015 | 2/2008 |
| WO | WO-2009 112488 | 9/2009 |

OTHER PUBLICATIONS

Dernedde, J. et al., "Dendritic polyglycerol sulfates as multivalent inhibitors of inflammation," PNAS, Nov. 16, 2010, vol. 107, No. 46, pp. 19679-19684.

(Continued)

*Primary Examiner* — Paul Dickinson
(74) *Attorney, Agent, or Firm* — Millen, White, Zelano & Branigan P.C.

(57) ABSTRACT

The present invention relates generally to methods and compositions for targeting of intracellular molecules involved in proliferation and protein synthesis of activated cells using polyanionic multivalent macromolecules. In particular aspect, multiple sulfate groups linked to polyol are specifically targeted to the cytoplasm and nucleus of proliferating and activated cells. The invention further comprises novel polyanionic macromolecular compounds and formulations.

24 Claims, 21 Drawing Sheets

(51) Int. Cl.
  *A61K 49/00*   (2006.01)
  *A61K 41/00*   (2006.01)
  *C07D 487/22*  (2006.01)
  *A61K 49/08*   (2006.01)
  *C07C 237/14*  (2006.01)
  *C07D 403/14*  (2006.01)
  *C07D 403/10*  (2006.01)
  *C07D 405/12*  (2006.01)
  *A61K 47/48*   (2006.01)
  *A61K 49/12*   (2006.01)
  *C07H 21/02*   (2006.01)
  *A61K 51/06*   (2006.01)

(52) U.S. Cl.
  CPC ... 41/0071 (2013.01); *A61K 49/085* (2013.01); *A61K 49/0032* (2013.01); *C07C 237/14* (2013.01); *C07D 403/14* (2013.01); *C07D 403/10* (2013.01); *C07D 405/12* (2013.01); *A61K 47/48192* (2013.01); *A61K 49/124* (2013.01); *C07H 21/02* (2013.01); *A61K 51/065* (2013.01); *A61K 49/0054* (2013.01)
  USPC .................................................... 424/78.17

(56) References Cited

U.S. PATENT DOCUMENTS

2011/0065896 A1   3/2011   Licha et al.
2012/0328519 A1   12/2012  Haag et al.

OTHER PUBLICATIONS

International Search Report for PCT/EP2011/000425, Date of the actual completion of the international search: May 18, 2011, Date of mailing of the international search report: Jun. 1, 2011.

KhanDare, J. et al., "Structure-biocompatibility relationship of dendritic polyglycerol derivatives," Biomaterials, 2010, vol. 31, pp. 4268-4277.

Türk, H. et al., "Dendritic polyglycerol sulfates as new heparin analogues and potent inhibitors of the complement system," Bioconjugate Chem., 2004, vol. 15, pp. 162-167.

Written Opinion of the International Search Authority for PCT/EP2011/000425 dated Aug. 3, 2012.

Compound P14 / P20 / P22 / P23 / P28 (after cleavage of protecting group)

Compound P22

Compound P17

Compound P18

Diagnostic effector conjugate derived from P14 and E3 (example 3a)

Diagnostic effector conjugate derived from P26 and E2 (example 3b)

Diagnostic effector conjugate derived from P17 and E5 (example 3c)

Conjugate for radioimaging or radiotherapy derived from P17 and E13 (example 4a; chelator without radioisotope)

Diagnostic effector conjugate for MRI derived from P27 and E16 (example 5a; chelator without radioisotope)

Therapeutic effector conjugate from P16 and E20 (example 6a)

Therapeutic effector conjugate from P14 and E25 (example 6b)

Therapeutic effector conjugate from P16 and E26 (example 6c)

Therapeutic effector conjugate from P16 and E33 (example 6e)

a)

b)

c)

d)

US 8,877,171 B2

POLYANIONIC MULTIVALENT MACROMOLECULES FOR INTRACELLULAR TARGETING OF PROLIFERATION AND PROTEIN SYNTHESIS

SEQUENCE LISTING

The instant application contains a Sequence Listing which has been submitted in ASCII format via EFS-Web and is hereby incorporated by reference in its entirety. Said ASCII copy, created on Dec. 6, 2012, is named ANDRAE-0002SQL.txt and is 1,784 bytes in size.

FIELD OF THE INVENTION

The present invention relates generally to methods and compositions for targeting of intracellular molecules involved in proliferation and protein synthesis of activated cells using polyanionic multivalent macromolecules. In particular aspect, multiple sulfate groups linked to polyol are specifically targeted to the cytoplasm and nucleus of proliferating and activated cells. The invention further comprises novel polyanionic macromolecular compounds and formulations.

BACKGROUND OF THE INVENTION AND DESCRIPTION OF RELATED ART

During the last decades much progress has been made to improve the efficacy of diagnostic and therapeutic drugs. Major achievements have been made in acute diseases. Today, acute diseases such as infectious diseases, acute thrombosis or acute dysregulation of blood pressure can be treated with high efficacy. Most drug treatments for acute diseases do not seriously affect healthy tissues and organs. Because of the short period of drug treatment healthy tissues and organs can sufficiently recover from unwanted drug effects. In contrast to the short lasting drug treatment of acute diseases which is usually accompanied with a short period of drug exposure, treatment of chronic diseases is indispensible associated with a long lasting exposure of the human body to the applied drugs. The long lasting exposure of the drug, however, often harms healthy tissues and organs.

Two different strategies were followed during the last decades to avoid severe unwanted drug effects on healthy tissues and organs. On the one hand, drug research was focused on new drug targets that promised a disease-specific expression of the target mechanism. With respect to the discovery of signal transduction mechanisms in proliferating and activated cells, numerous new targets have been identified. However, with few exceptions therapeutic attack of the majority of newly discovered drug targets did not improve therapeutic outcome. On the other hand side, much effort has been devoted to improve the bioavailability of clinically established therapeutic drugs. In order to improve bioavailability drug research focused on the chemical modification or pharmaceutical formulations of the therapeutic or diagnostic effector molecules.

Over the past three decades the use of targeted effector conjugates has been well established. In particular, molecules which can induce diagnostic or therapeutic effects are linked to a carrier molecule with targeting properties. Due to the high binding affinity of immunoglobulins, protein antibodies or antibody fragments are frequently used as carrier molecules for targeted delivery. With respect to the treatment of neoplastic diseases, antibodies may carry toxins or chemotherapeutic agents to the tumor. Because of the strong binding of the antibody-effector conjugates to certain target molecule of tumors, a significantly higher concentration of the effector in the tumor environment is achieved. Meanwhile, antibody-effector conjugates have proven effective in a series of experimental and clinical tumors. Another advantage of the targeted delivery of effector molecules is the reduction of unwanted effects of the effector molecule. In detail, the majority of drug molecules which are not linked to the carrier with targeting properties do not reach the site of the disease and are only applied into the human body in order to achieve necessary drug concentration in the blood. Therefore, the utmost portion of the applied drug is eliminated from blood circulation without reaching the site of the disease. For example, malignant solid tumors which can be regarded as a chronic disease have a size of 1 to 10 gram at the time point of diagnosis and treatment, therefore, represent 0.01 to 0.001% of the human body. This ratio illustrates that drug treatment can be significantly optimized by directing the applied drug to the disease, and, therefore, enable reduction of the applied dose.

However, despite of remarkable progress in the treatment of acute diseases, the majority of treatments fail to achieve cure from the chronic disease. In contrast to acute diseases, most chronic diseases can only be treated if disease-related signal transduction and gene transcription can be selectively targeted. In order to achieve this goal, therapeutic drugs have to sufficiently permeate the cell membrane and to accumulate within the target cell of the disease. Because of the ubiquitous expression of the key target molecules of gene transcription and protein synthesis, future therapeutic drugs have to demonstrate selective uptake at the site of the disease. The latter characteristic of future therapeutic drugs is of crucial importance because binding to and inhibition of key regulators of gene transcription and protein synthesis outside the disease process may harm the human body.

Results from scientific investigations provided evidence for a role of more than 500 factors in gene transcription and protein synthesis. However, among the different factors, NF-kappaB and AP-1 are crucial and have already been established as therapeutic targets (Letoha et al., Mol. Pharmacol. 69: 2027, 2006; Sliva et al., Curr Cancer Drug Targets. 4: 327, 2004) These two regulators of gene transcription play a central role in activation and proliferation of cells and are the downstream signal of different signaling cascades. Both NF-kappaB and AP-1 are located in the cytoplasm and nuclei of cells. With respect to therapeutic targeting of NF-kappaB and AP-1, drugs have to fulfill two important prerequisites. First, a therapeutic drug has to permeate the cell membrane in sufficient amount and to accumulate within the cytoplasm. Second, the therapeutic drug has to discriminate between cells in healthy organs or tissues and cells in the disease process. The latter aspect is of great significance because NF-kappaB and AP-1 are expressed in every cell of the human body and an inhibition of these two disease targets may significantly harm sensitive body functions.

NF-kappaB (nuclear factor kappa-light-chain-enhancer of activated B cells) is a protein complex that controls the transcription of DNA. NF-kappaB is found in almost all animal cell types and is involved in cellular responses to stimuli such as stress, cytokines, free radicals, ultraviolet irradiation, oxidized LDL, and bacterial or viral antigens. NF-kappaB plays a key role in regulating the immune response to infection. Conversely, incorrect regulation of NF-kappaB has been linked to cancer, inflammatory and autoimmune diseases, septic shock, viral infection, and improper immune development. NF-kappaB has also been implicated in processes of synaptic plasticity and memory (Baud et al., Nat Drug Discov. 8:33, 2009).

NF-kappaB is widely used by eukaryotic cells as a regulator of genes that control cell proliferation and cell survival. As such, many different types of human tumors have misregulated NF-kappaB: that is, NF-kappaB is constitutively active. Active NF-kappaB turns on the expression of genes that keep the cell proliferating and protect the cell from conditions that would otherwise cause it to die via apoptosis. Defects in NF-kappaB result in increased susceptibility to apoptosis leading to increased cell death. Because NF-kappaB controls many genes involved in inflammation, it is not surprising that NF-kappaB is found to be chronically active in many inflammatory diseases, such as inflammatory bowel disease, arthritis, sepsis, gastritis, asthma, among others. Many natural products (including anti-oxidants) that have been promoted to have anti-cancer and anti-inflammatory activity have also been shown to inhibit NF-kappaB (Kaur et al., Curr Cancer Drug Targets 7: 355, 2007).

Activator protein 1 (AP-1) is a transcription factor which is a heterodimeric protein composed of proteins belonging to the c-Fos, c-Jun, ATF and JDP families. It regulates gene expression in response to a variety of stimuli, including cytokines, growth factors, stress, and bacterial and viral infections. AP-1 in turn controls a number of cellular processes including differentiation, proliferation, and apoptosis (Vesely et al., Mutat Res. 682: 7, 2009).

Activation of NF-kappaB and AP-1 results into transcription of genes encoding for numerous signaling molecules involved in tumor growth, apoptosis, inflammation, autoimmune disease and fibrosis. Cytokines such as interleukin-1, interleukin-6, TNF-alpha or growth factors like TGF-beta (TGF-β) represent the most important downstream signals of NF-kappaB and AP-1 activation. In particular, transforming growth factor beta (TGF-beta) is a highly pleiotropic cytokine that controls many aspects of cellular function, including cellular proliferation, differentiation, migration, apoptosis, adhesion, angiogenesis, immune surveillance, and survival and, therefore, represents an important target for therapeutic drugs (Jakowlew, Cancer Metastasis Rev 2006; 25:435-57). TGF-beta is produced by many cell types, is always present in the plasma (in its latent form) and permeates all organs, binding to matrix components and creating a reservoir of this immunosuppressive molecule. Anyway, it is overproduced in many pathological conditions. This includes pulmonary fibrosis, glomerulosclerosis, renal interstitial fibrosis, cirrhosis, Crohn's disease, cardiomyopathy, scleroderma and chronic graft-versus-host disease (Prud'homme et al., Lab Invest 2007; 87:1077-91). In neoplastic disease, TGF-beta suppresses the progression of early lesions, but later this effect is lost and cancer cells produce TGF-beta, which then promotes metastasis. This cytokine also contributes to the formation of the tumor stroma, angiogenesis and immunosuppression (Jakowlew, Cancer Metastasis Rev 2006; 25:435-57). In view of this, several approaches are being studied to inhibit TGF-beta activity, including neutralizing antibodies, soluble receptors, receptor kinase antagonist drugs, and antisense reagents. The benefits of new therapies targeting TGF-beta are under intense investigation (Prud'homme, Lab Invest 2007; 87:1077-91).

For a therapeutic intervention all autoimmune diseases are considered where the pathological process is characterized by a defect and unregulated interaction of cellular and non-cellular components of the immune system such as coeliac disease, diabetes mellitus type 1 (IDDM), systemic lupus erythematosus (SLE), Sjögren's syndrome, Churg-Strauss Syndrome, multiple sclerosis (MS), Hashimoto's thyroiditis, Graves' disease, idiopathic thrombocytopenic purpura, Addisons disease, anemia, ankylosing spondylitis, osteoarthritis, Behcets Syndrome, Canker Sores, chronic fatigue, chronic obstructive pulmonary disease (COPD), Crohns disease, Cushings disease, dermatitis herpetiformis, dermatomyositis, eczema, fibromyalgia, hair loss, hepatitis, hypothyroidism, lichen planus, Meniere's Disease, myasthenia, Reiters Syndrome, sarcoidosis, scleroderma, sepsis, Sjogrens Syndrome, sun poisoning, SIRS (systemic inflammatory response syndrome) and uveitis (Masters et al, Annu Rev Immunol 2009; 27:621-68).

In human cancers, TGF-beta is produced by activation of NF-kappaB or AP1 and promotes tumorigenesis through both decreased TGF-beta signaling during early tumorigenesis and increased TGF-beta signaling in advanced, progressive disease. There is evidence that TGF-beta regulates the cell-cycle activity of tumor cells leading to a control of tumor cell proliferation. While the growth of normal cells and differentiated tumor cells is blocked by TGF-beta, the growth of undifferentiated tumor cells is stimulated. The stimulatory action of TGF-beta in undifferentiated tumor cells is due to a mutated signaling pathway. Despite the effect of TGF-beta on the growth of primary tumor cells, TGF-beta is one of the most potent regulators of the tumor metastasis through a stimulation of the tumor cell extravasation. An effect on the tumor angiogenesis is another mechanism of TGF-beta to stimulate tumor growth and metastasis (Tian et al., Future Oncol 2009; 5:259-71). Elevated levels of TGF-beta were found in a number of tumors as acute lymphoblastic leukemia, acute myeloid leukemia, adrenocortical carcinoma, AIDS-related cancers, AIDS-related lymphoma, astrocytoma, basal cell carcinoma, skin cancer (nonmelanoma), bile duct cancer, bladder cancer, bone cancer, fibrous histiocytoma, brain tumor, breast cancer, bronchial tumors, Burkitt lymphoma, carcinoid tumor, cervical cancer, chronic lymphocytic leukemia, chronic myelogenous leukemia, chronic myeloproliferative disorders, colon cancer, cutaneous T-Cell lymphoma, Mycosis Fungoides, embryonal tumors, esophageal cancer, eye Cancer, gallbladder cancer, gastric (stomach) cancer, gastrointestinal carcinoid tumor, germ cell tumor, glioma, hairy cell leukemia, head and neck cancer, hepatocellular (liver) cancer, Hodgkin lymphoma, islet cell tumors, kidney (renal cell) cancer, laryngeal cancer, liver cancer, lung cancer, lymphoma, melanoma, mesothelioma, myelodysplastic syndromes, nasopharyngeal cancer, ovarian cancer, pancreatic cancer, parathyroid cancer, prostate cancer, benign prostate hyperplasie, rectal cancer, sarcoma, stomach cancer, thyroid cancer, vaginal cancer (Jones et al., Expert Opin Ther Targets 2009; 13:227-34).

A critical role for TGF-beta was also corroborated in diseases of the cardiovascular system. Very similar to the mechanism of TGF-beta induction in tumors, a major stimuli of TGF-beta synthesis in cardiovascular disease is activation of NF-kappaB, too (Frangogiannis, Pharmacol Res 2008; 58:88). TGF-beta has been implicated in many cardiovascular disorders such as stroke reperfusion, ischemia, heart attack, myocarditis, endocarditis, myocardial insufficiency (Goumans et al, Trends Cardiovasc 2008; 18:293-8). TGF-beta has important roles in the development of the neointima and constrictive remodeling associated with angioplasty. In atherosclerosis its actions are yet to be fully elucidated but its ability to control the immune system has profound effects on lesion development, particularly by influencing the types of lesions that develop. TGF-beta can also induce arteriogenesis and markedly influences angiogenic processes, possessing both pro- and anti-angiogenic effects (Galinka et al, Annu Rev Immunol 2009; 27:165-97). It is also a major contributor to the development of various cardiovascular fibrotic disorders including those in the vasculature, heart and kidney.

TGF-beta was also shown to play an important role in the development and progression of fibrosis. Fibrosis is the formation or development of excess fibrous connective tissue in an organ or tissue as a reparative or reactive process, as opposed to a formation of fibrous tissue as a normal constituent of an organ or tissue. Examples are cystic fibrosis of the pancreas and lungs, injection fibrosis, which can occur as a complication of intramuscular injections, endomyocardial fibrosis, idiopathic pulmonary fibrosis of the lung, mediastinal fibrosis, myelofibrosis, retroperitoneal fibrosis, progressive massive fibrosis, a complication of coal workers' pneumoconiosis, nephrogenic systemic fibrosis (Pohlers et al., Biochim Biophys Acta, 2009, 1792, 746-756).

Currently available anti-TGF-beta therapeutic drugs exert several disadvantages. The significant disadvantage of established drugs for treatment of autoimmune disease is their small therapeutic window. Repeated applications usually lead to adverse drug effects and severe organ damages. Cardiotoxicity, nephrotoxicity and hepatitis are common side effects of clinically available drugs for treatment of autoimmune disease (Cohen, International Journal of Clinical Practice 2007; 1922-1930). In the clinical setting, most established drugs are intermittently applied to avoid irreversible toxicity. However, intermittent treatment schedules increase the risk of disease progression. For these reasons, a significant need for more efficient and well tolerated drugs for treatment of TGF-beta related diseases exists.

It is known that TGF-beta can be inhibited by several approaches leading to an inhibition of the receptor signaling. However, these approaches are hampered by a limited efficacy and lack of tolerability in vivo. The synthesis of antisense oligonucleotides to block TGF-beta was described (Flanders, Clinical Medicine & Research 2003, 1, 13-20). Antisense oligonucleotides can diminish the synthesis of the TGF-beta protein. However, this approach does often lead to an incomplete inhibition of TGF-beta synthesis. Another disadvantage of antisense oligonucleotides is the low amount of drug accumulated at the site of disease. Small molecule inhibitors (SMIs) of the TGF-beta receptor are also known (Hjelmeland et al., Mol Cancer Ther 2004; 3: 737-745). These molecules are often orally available but lack sufficient tolerability and safety. The toxic side effects of known SMI's of the TGF-beta receptor are due to a lack of specificity. The known compound do not only inhibit signaling of the TGF-beta receptor but also many other receptors with structural similarities. Antibodies that bind TGF-beta or block TGF-beta binding to its receptors are also known. These molecules show sufficient accumulation at the site of the disease and do block signaling over a long period (Saunier et al, Curr Cancer Drug Targets 2006; 6:565-78). However, antibodies bear several disadvantages which do limit their therapeutic application. First, antibodies interfering with TGF-beta may exert unwanted side effects due to activation of the immune system by parts of the antibodies carrying binding sites to components of the immune system. This activation of the immune system can lead to toxicity of the treatment. Another disadvantage may be the production of neutralizing antibodies. The onset of neutralizing antibodies is frequently observed after multiple applications. In case of neutralizing antibodies the efficacy of the treatment is decreased.

Because of the limitation of the known treatments, novel approaches to treat diseases related to activated NF-kappaB and AP-1 and elevated synthesis of TGF-beta are required. The ultimate goal of a novel therapeutic approach is high efficacy and good tolerability. Therefore, it is an objective of the present invention to provide compounds and compound classes which are easy to synthesize and which are suitable for the treatment of disease associated with activation of NF-kappaB or AP-1 and elevated synthesis of cytokines such as TGF-beta. According to the invention, it was surprisingly found that polyanionic multivalent macromolecules represent a novel class of therapeutic molecules that selectively deliver effector molecules into the cytoplasm and nuclei of proliferating and activated cells.

The invention proposes the use of polyanionic macromolecules based on the multivalent assembly of a plurality of sulfate groups on a dendritic branched macromolecular carrier for intracellular delivery of diagnostic or therapeutic effector molecules. More specifically, the invention comprises the use of sulfated polyols with hyperbranched structure to which diagnostic or therapeutic effector molecules are covalently attached as drugs to treat diseases related to activated NF-kappaB and AP-1 and elevated synthesis of TGF-beta.

SUMMARY OF THE INVENTION

Subject matter of the present invention is:

A pharmaceutical composition comprising a sulfated polyglycerol and a therapeutic or diagnostic effector molecule that is covalently conjugated to said sulfated polyglycerol.

In a preferred embodiment a pharmaceutical composition of the formula $P(OSO_3^-M^+)_n(L-G-E)_m$ with P is a polyol macromolecule wherein a number n of hydroxyl groups is substituted by sulfate groups $OSO_3^-M^+$, M is a cationic inorganic or organic counter ion to the anionic sulfate group, E is therapeutic or diagnostic effector molecule, L is a linker or spacer between P and E, G is a reactive group for the covalent attachment between L and E, and m is a number of 1-100.

In a more preferred embodiment a pharmaceutical composition for treating a disease by intracellular uptake of said sulfated polyglycerol and a therapeutic or diagnostic effector molecule into activated cells or proliferative cells and by inhibiting NF-kappaB and/or AP-1 and/or inhibiting TGF-beta synthesis in said cells.

A conjugate comprising a sulfated polyglycerol and a therapeutic or diagnostic effector molecule that is covalently conjugated to said sulfated polyglycerol.

In a preferred embodiment a conjugate of the formula $P(OSO_3^-M^+)_n(L-G-E)_m$ with P is a polyol macromolecule wherein a number n of hydroxyl groups is substituted by sulfate groups $OSO_3^-M^+$, M is a cationic inorganic or organic counter ion to the anionic sulfate group, E is therapeutic or diagnostic effector molecule, L is a linker or spacer between P and E, G is a reactive group for the covalent attachment between L and E, and m is a number of 1-100.

In a more preferred embodiment a conjugate of the formula $P(OSO_3^-M^+)_n(L-G-E)_m$ wherein a number n of hydroxyl groups is substituted by sulfate groups $OSO_3^-M^+$, with n is a number >10.

In an even more preferred embodiment a conjugate, wherein the effector molecule accounts to less than 50% by weight to the conjugate, and the conjugate has a solubility in water of more than 100 mg/mL.

In an even more preferred embodiment a conjugate comprising a sulfated polyglycerol and a therapeutic or diagnostic effector molecule that is covalently conjugated to said sulfated polyglycerol for treating a disease by intracellular uptake into activated cells or proliferative cells and by inhibiting NF-kappaB and/or AP-1 and/or inhibiting TGF-beta synthesis in said cells.

In an even more preferred embodiment a conjugate comprising a sulfated polyglycerol and a therapeutic or diagnostic effector molecule that is covalently conjugated to said sulfated polyglycerol for treating a disease selected from the group comprising cancer, inflammation, autoimmune disease and fibrosis.

In an even more preferred embodiment a conjugate comprising a sulfated polyglycerol and a therapeutic or diagnostic effector molecule that is covalently conjugated to said sulfated polyglycerol for treating a disease by intracellular uptake of said sulfated polyglycerol and a therapeutic or diagnostic effector molecule into activated cells or proliferative cells and by inhibiting NF-kappaB and/or AP-1 and/or inhibiting TGF-beta synthesis in said cells, wherein multiple treatment with doses of 1 mg/kg to 1000 mg/kg per administration is performed.

In an even more preferred embodiment a conjugate comprising
a) a polymeric polyglycerol P, composed of repeated units of glycerol with the formula (RO—CH$_2$)$_2$CH—OR on a multifunctional starter molecule, which is a polyhydroxy compound having 1 to 1,000 OH groups, wherein R is H or further glycerol units, the core having a branching degree of 0 to 67%, an average molecular weight of 500 to 1,000,000 g/mol,
b) the substitution of a plurality of OH groups of the glycerol units with —OSO$_3$H or —OSO$_3^-$M$^+$, with a preferred number of —OSO$_3$H or —OSO$_3^-$M$^+$ groups being above 10, and a degree of sulfation X of 30 to 100% is obtained, with M$^+$ being a cationic inorganic or organic counter ion.
c) a resulting average molecular weight of the sulfated polyglycerol 1,000 to 5,000,000 g/mol,
d) a linker unit L carrying a functional group G, attached to at least one of the OH groups up to maximal 100-X % of the OH groups, with the functional groups being able to be conjugated with an additional therapeutic or diagnostic effector molecule, wherein X is the degree of sulfation.
e) a diagnostic and/or therapeutic effector molecule covalently attached to one up to the maximal possible number of said functional groups, the diagnostic effector molecule being selected from the group of fluorescent dyes or chelators for radioactive or paramagnetic metals, and the therapeutic effector molecules being selected from the group of cytostatics, anti-angiogenetic drugs, photosensitizers, siRNAs.

In an even more preferred embodiment a conjugate of the formula P(OSO$_3^-$M$^+$)$_n$(L-G-E)$_m$ wherein L is a branched or linear C$_{1-20}$-alkyl group in which one or more non-consecutive methylene groups may be replaced by a group selected from O, S, NH, C(O)NH, C(O), SO$_2$, SO, aryl, ethene or ethyne, and wherein G is selected from the group comprising —OH, —OSO$_3$H, —OSO$_3^-$, —NH$_2$, —N$_3$, —COOH, —SH, —SO$_3^-$, —C≡C.

A sulfated polyglycerol of the general formula P(OSO$_3^-$M$^+$)$_n$(L-G)$_m$, for treating a disease by intracellular uptake into activated cells or proliferative cells and by inhibiting NF-kappaB and/or AP-1 and/or inhibiting TGF-beta synthesis in said cells, with P stands for a polyglycerol wherein a number n of hydroxyl groups is substituted by sulfate groups OSO$_3^-$M$^+$, M is a cationic inorganic or organic counter ion to the anionic sulfate group, m is a number of 1-100, L is a linker, G is a reactive group for the covalent attachment with effector molecules, wherein L is a branched or linear C$_{1-20}$-alkyl group in which one or more non-consecutive methylene groups may be replaced by a group selected from O, S, NH, C(O)NH, C(O), SO$_2$, SO, aryl, ethene or ethyne, and wherein G is selected from the group comprising —OH, —OSO$_3$H, —OSO$_3^-$, —NH$_2$, —N$_3$, —COOH, —SH, —SO$_3^-$, —C≡C.

In a more preferred embodiment a sulfated polyglycerol for treating a disease selected from the group comprising cancer, inflammation, autoimmune disease and fibrosis by intracellular uptake into activated cells or proliferative cells and by inhibiting NF-kappaB and/or AP-1 and/or inhibiting TGF-beta synthesis in said cells.

In an even more preferred embodiment a sulfated polyglycerol for treating a disease selected from the group comprising cancer, inflammation, autoimmune disease and fibrosis by intracellular uptake into activated cells or proliferative cells and by inhibiting NF-kappaB and/or AP-1 and/or inhibiting TGF-beta synthesis in said cells, wherein multiple treatment with doses of 1 mg/kg to 1000 mg/kg per administration is performed.

Use of sulfated polyglycerol according to
a conjugate comprising a sulfated polyglycerol and a therapeutic or diagnostic effector molecule that is covalently conjugated to said sulfated polyglycerol
and
in a preferred embodiment a conjugate of the formula P(OSO$_3^-$M$^+$)$_n$(L-G-E)$_m$ with P is a polyol macromolecule wherein a number n of hydroxyl groups is substituted by sulfate groups OSO$_3^-$M$^+$, M is a cationic inorganic or organic counter ion to the anionic sulfate group, E is therapeutic or diagnostic effector molecule, L is a linker or spacer between P and E, G is a reactive group for the covalent attachment between L and E, and m is a number of 1-100
and
in a more preferred embodiment a conjugate of the formula P(OSO$_3^-$M$^+$)$_n$(L-G-E)$_m$ wherein a number n of hydroxyl groups is substituted by sulfate groups OSO$_3^-$M$^+$, with n is a number >10
for delivery of a therapeutic or diagnostic effector molecule into activated or proliferative cells of a subject.

Use of a sulfated polyglycerol according to
a sulfated polyglycerol of the general formula P(OSO$_3^-$M$^+$)$_n$(L-G)$_m$ for treating a disease by intracellular uptake into activated cells or proliferative cells and by inhibiting NF-kappaB and/or AP-1 and/or inhibiting TGF-beta synthesis in said cells, with P stands for a polyglycerol wherein a number n of hydroxyl groups is substituted by sulfate groups OSO$_3^-$M$^+$, M is a cationic inorganic or organic counter ion to the anionic sulfate group, m is a number of 1-100, L is a linker, G is a reactive group for the covalent attachment with effector molecules, wherein L is a branched or linear C$_{1-20}$-alkyl group in which one or more non-consecutive methylene groups may be replaced by a group selected from O, S, NH, C(O)NH, C(O), SO$_2$, SO, aryl, ethene or ethyne, and wherein G is selected from the group comprising —OH, —OSO$_3$H, —OSO$_3^-$, —NH$_2$, —N$_3$, —COOH, —SH, —SO$_3^-$, —C≡C
and
in a more preferred embodiment a sulfated polyglycerol for treating a disease selected from the group comprising cancer, inflammation, autoimmune disease and fibrosis by intracellular uptake into activated cells or proliferative cells and by inhibiting NF-kappaB and/or AP-1 and/or inhibiting TGF-beta synthesis in said cells
for delivery of a therapeutic or diagnostic effector molecule into activated or proliferative cells of a subject.

In an even more preferred embodiment the use of a sulfated polyglycerol wherein the therapeutic or diagnostic effector molecule is covalently attached to the sulfated polyglycerol.

Waterless formulation of a sulfated polyglycerol according to
a conjugate comprising a sulfated polyglycerol and a therapeutic or diagnostic effector molecule that is covalently conjugated to said sulfated polyglycerol.

Waterless formulation of a sulfated polyglycerol according to a sulfated polyglycerol of the general formula $P(OSO_3^-M^+)_n(L-G)_m$ for treating a disease by intracellular uptake into activated cells or proliferative cells and by inhibiting NF-kappaB and/or AP-1 and/or inhibiting TGF-beta synthesis in said cells, with P stands for a polyglycerol wherein a number n of hydroxyl groups is substituted by sulfate groups $OSO_3^-M^+$, M is a cationic inorganic or organic counter ion to the anionic sulfate group, m is a number of 1-100, L is a linker, G is a reactive group for the covalent attachment with effector molecules, wherein L is a branched or linear $C_{1-20}$-alkyl group in which one or more non-consecutive methylene groups may be replaced by a group selected from O, S, NH, C(O)NH, C(O), $SO_2$, SO, aryl, ethene or ethyne, and wherein G is selected from the group comprising —OH, —$OSO_3H$, —$OSO_3^-$, —$NH_2$, —$N_3$, —COOH, —SH, —$SO_3^-$, —C≡C.

In an even more preferred embodiment a waterless formulation for treating a disease by intracellular uptake in activated cells or proliferative cells and by inhibiting NF-kappaB and/or AP-1 and/or inhibiting TGF-beta synthesis in said cells.

In an even more preferred embodiment a waterless formulation for treating a disease selected from the group comprising cancer, inflammation, autoimmune disease and fibrosis.

In an even more preferred embodiment a waterless formulation wherein multiple treatment with doses of 1 mg/kg to 1000 mg/kg per administration is performed.

In an even more preferred embodiment a waterless formulation, comprising a lyophilisate containing buffer salts and/or at least one cryoprotectant selected from the group of sucrose, mannose, trehalose.

DETAILED DESCRIPTION OF THE INVENTION

Figure 1:
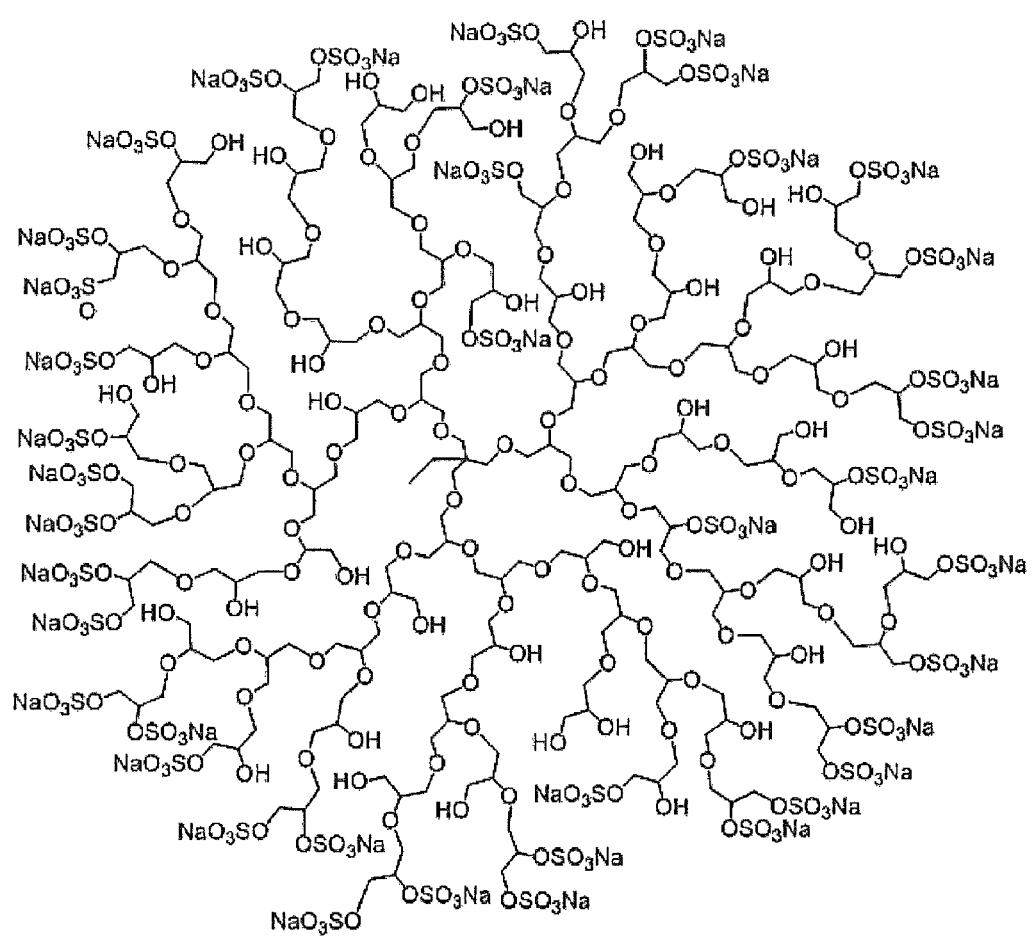
FIG. 1 is a schematic representation of an exemplary chemical structure of a macromolecular polyanionic polysulfate with dendritic polyglycerol backbone. The starter molecule is TMP. The formula depicts the principal structural entity of a dendritic, hyperbranched, sulfated polyglycerol. Synthesis of various derivatives is described in examples 1 and 2.

The objective of the present invention is to provide a drug for the treatment of tumor disease, inflammation, autoimmune disease and fibrosis which is characterized by high therapeutic effectiveness and good tolerability. Polyanionic multivalent macromolecules according to the present invention are suited for delivery of effector molecules into the cytoplasm and nuclei of proliferating and activated cells to diagnose or treat tumor disease, inflammation, autoimmune disease and fibrosis, especially because of their surprisingly found high efficacy and good tolerability even after application of high doses.

A systematically studied cellular pathway is the endocytosis of macromolecules with increasing molecular weight. Endocytosis is the process by which cells absorb molecules (such as macromolecules) from outside the cell by engulfing it with their cell membrane. It is a general mechanism applied by all cells of the body because most substances and substrates important to them are large polar molecules that cannot pass through the hydrophobic plasma membrane or cell membrane. The process of endocytosis is present in both healthy cells and cells involved in the disease process (Liu et al., PLOS Biology 2009; 7:1000204).

The mechanism of endocytosis is involved particularly when large molecules of macromolecular structure or particle-based entities (organic or inorganic nanoparticles) reach the cell membrane. The design of drugs with improved targeting properties has therefore been accomplished by applying macromolecular carrier molecules. In particular, polymeric entities or dendrimers have been synthesized in broad variety (Nori et al., Adv Drug Deliv Rev. 57: 609, 2005, Haag et al., Angew. Chem. Int. Ed. 45: 1198, 2006). Chemical modifications of macromolecules with respect to targeting properties of the molecules are well established. There is strong evidence that cationic structures placed on a macromolecule enable macromolecules to cross the cell membrane through endocytosis. In this regard, cationic macromolecules are used for intracellular delivery of diagnostic and therapeutic effectors (Paleos et al., Curr Top Med. Chem. 8: 1204, 2008). However, cationic macromolecules are taken up by every cell in the human organism according to the general capability of every cell to apply the mechanism of endocytosis. Drug delivery therefore involves components and structures with cationic elements (e.g. WO2009142893). This leads to many unwanted effects and toxicity of the drug treatment, as well as to deposit of the drugs in unwanted compartments of the body. A cationic peptide Penetratin was identified as intracellular inhibitor for NF-kappaB (Letoha et al. Mol. Pharmacol. 69: 2027, 2006).

It is known that the majority of anionic structures are not taken up by cells because of the negative charge of the cell membrane of an intact cell leading to repulsion and prevention of cell membrane permeation. Macromolecular entities possessing polyanionic behavior have been described in broad variety. Among this group are naturally occurring compounds such as proteoglycans, lipid bilayer surfaces, microtubules and polynucleotides such as DNA or RNA. They play a central role in gene transcription and protein synthesis. Other compounds are artificial polymeric macromolecules or dendrimers such polyamino acids, polycarboxylates and synthetic oligonucleotides. Because of the negative charge of the cell membrane of an intact cell it can be expected that the electrostatic interaction of polyanionic macromolecules with the cell membrane may lead to repulsion and prevention of cell membrane permeation. Therefore, it is not known that polyanionic macromolecules can be used for delivery of effector molecules into the cytoplasm and nuclei of proliferating and activated cells. In fact, great efforts have been made to deliver RNA or siRNA to intracellular compartment by the aid of cationic or particular carrier molecules, because RNA or siRNA alone administered as drug effector is not capable to localize sufficiently in the cell (Jeong et al., Bioconjug. Chem. 20: 5, 2009).

In principle, there are many macromolecular compounds known which have been applied as carriers for drug delivery. These macromolecules can differ in their type of chemical structure of the polymeric or dendritic backbone, the attachment of anionic head charges, the molecular weight, and the degree of branching ranging from fully linear to hyperbranched structures. The chemical nature of the polymeric backbone can be derived from polymerization leading to polydisperse molecular weight distributions, or synthesized rationally giving dendrimers of defined structure and molecular weight. Well studied examples are Polyamidoamines (PAMAM), Polylysins (PL), Polyethylene imines (PEI), all of which are synthesized as polydisperse polymers of linear or branched structure, or as dendrimers of defined chemical structure. It is known to a person skilled in the art, that the generally underlying mechanism of cellular uptake of macromolecular entities, such as PAMAM, PEI, PL and others, is based on endocytotic pathways, as discussed above. Further information on macromolecular drug delivery can be found in the following literature: Saovapakhiran et al, Bioconjug. Chem. 20: 693, 2009; Seib et al., J. Contr. Release 117: 291, 2007, Nori et al., Adv Drug Deliv Rev. 57: 609, 2005, Haag et al., Angew. Chem. Int. Ed. 45: 1198, 2006.

Figure 2:
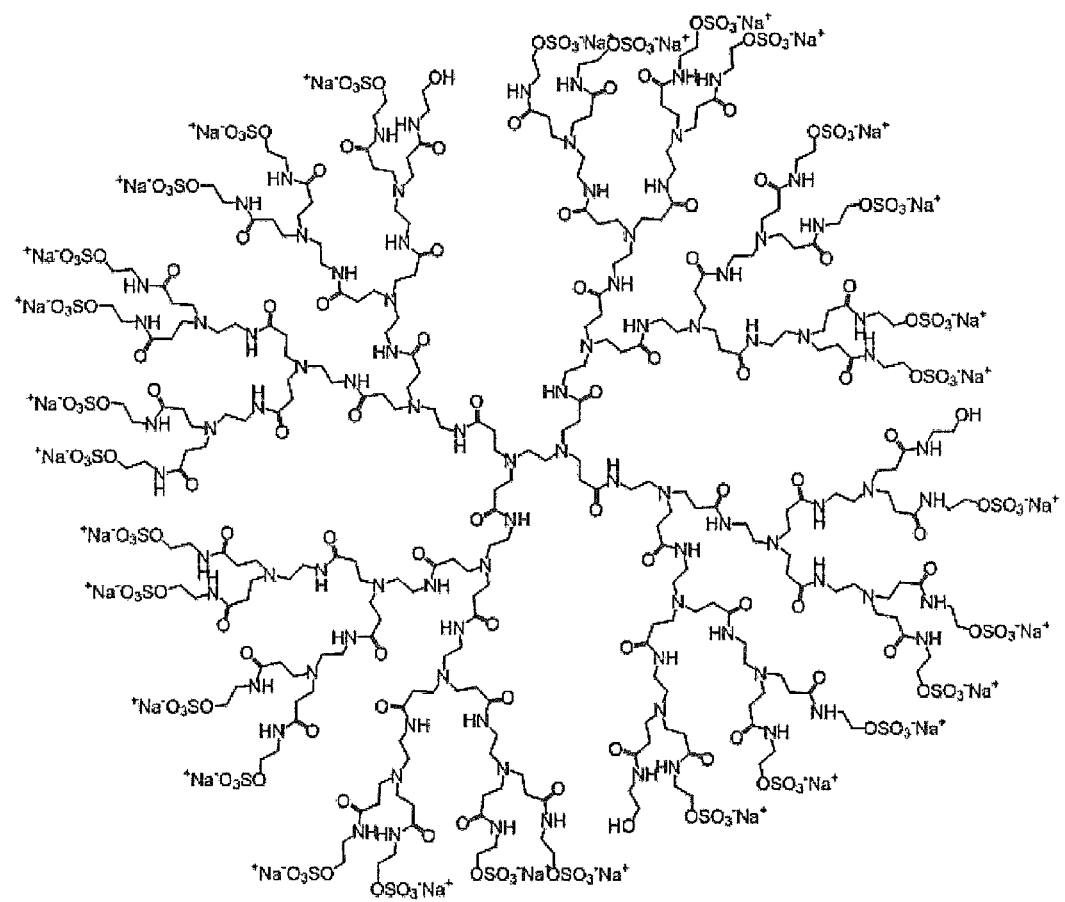
FIG. 2 is a schematic representation of an exemplary chemical structure of a macromolecular polyanionic polysulfate with poly(amidoamine) dendrimer backbone (Bioconjug. Chem. 20: 693, 2009). Sulfation of the dendrimer is performed as for polyglycerol. The formula depicts a compound with average sulfation of 90%.
Figure 3:
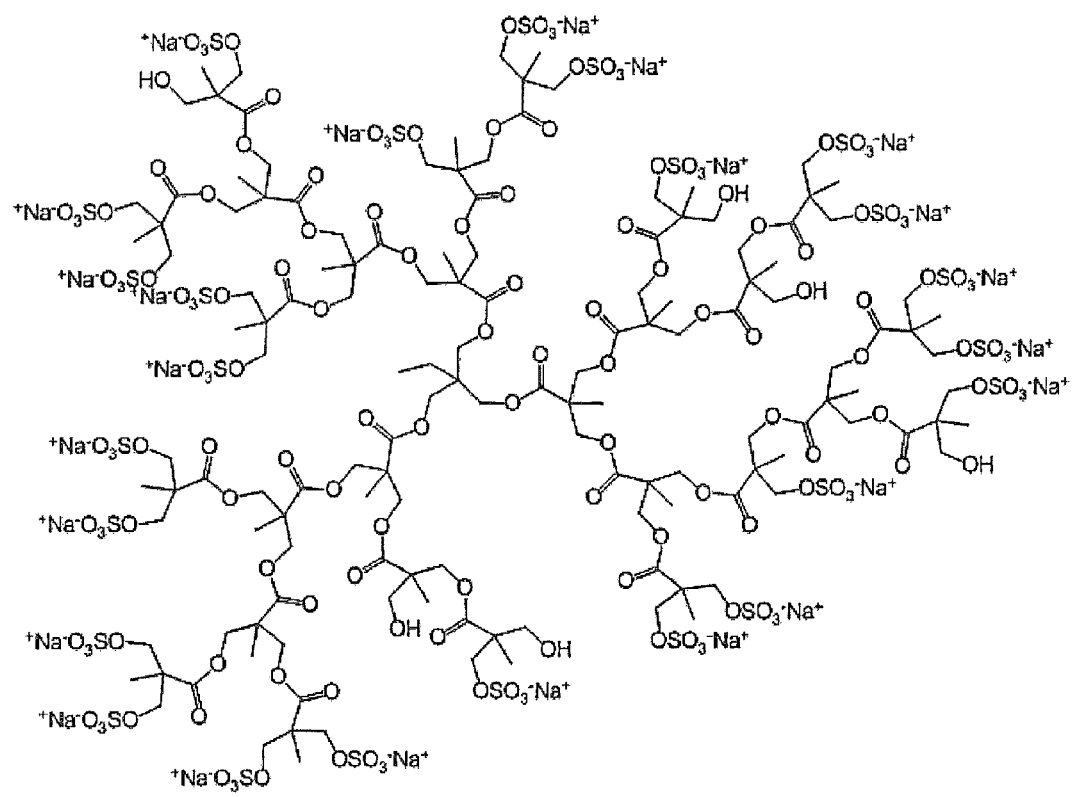
FIG. 3 is a schematic representation of an exemplary chemical structure of a macromolecular polyanionic polysulfate with Boltorn polyester dendrimer backbone (Bioconjug. Chem. 14: 817, 2003). Sulfation of the dendrimer is performed as for polyglycerol. The formula depicts a compound with average sulfation of 83%.

Surprisingly, it was found that the dendritic polyanionic macromolecule of the compound class of sulfated polyol selectively localizes inside the cell by a specific mechanism. Polyol of the same molecular weight but without sulfate groups did not localize in human A549 lung cancer cells. In particular, hyperbranched dendritic polyglycerols of different molecular weights ranging from 5 kDa to 208 kDa, but without sulfate groups, thus having only free hydroxyl groups of the polyol backbone, were labeled with a fluorescence carbocyanine dye (ICC) to comparatively measure the intracellular uptake in human A549 lung cancer cells. The inventors surprisingly found that only macromolecules with a molecular weight of 120 kDa and higher are taken up by human A549 lung cancer cells through endocytosis if they do not carry a plurality of sulfate groups. Furthermore, hyperbranched dendritic polyglycerol of a molecular weight up to 20 kDa and without sulfate groups does not cross the cell membrane via endocytosis (Example 7, FIG. 2), whereas sulfated polyglycerol of a molecular weight up to 20 kDa is localized within the cells. This clearly shows the advantage of sulfated dendritic polyglycerols in comparison to non-sulfated ones as sulfated ones are up-taken intracellulary.

It was further found that oligomeric sulfates do not show intracellular localization and do not have a reasonable binding affinity to NF-kappaB, when the number of sulfate groups assembled as plurality on a macromolecular carrier is below a certain value. A branched sulfated dendrimer based on glycerol ($1^{st}$ generation with 4 sulfates, $2^{nd}$ generation with 8 sulfates, $3^{rd}$ generation with 16 sulfates) conjugated to cyanine dye showed in all cases binding affinities to NF-kappaB of an IC50>1000 nM (example 11 of the present invention). It can be concluded that the multivalent assembly of a plurality of sulfate groups onto a polymeric or dendritic carrier backbone is the crucial enabling factor leading to the surprisingly identified properties of cellular localization and binding of transcription factors NF-kappaB and AP-1, and that a minimal number of sulfate groups is necessary. Therefore preferred are sulfated polyglycerols and sulfated polyglycerol conjugates exhibiting a number above 10 sulfate groups, more preferably above 15 sulfate groups, even more preferably above 20 sulfate groups, and most preferably above 25 sulfate groups.

It is therefore a novel and inventive property that anionic charge is capable to act as specific carrier into the inside of the cells and effector function for intracellular targeting of proliferation and protein synthesis when the anionic charge is assembled as a macromolecular plurality. More specifically, the anionic sulfate group is covalently attached on a macromolecular carrier molecule leading the above described surprisingly identified properties of cellular localization and binding of transcription factors NF-kappaB and AP-1 and inhibition of TGF-beta synthesis. According to the present invention, sulfated polyglycerols with a molecular size below the property of a macromolecule to be localized inside the cell through the process of endocytosis (as shown for polyglycerol without sulfate groups, requiring a much higher molecular weight to localize in the cell; see above) were surprisingly found to be specifically transported by a specific mechanism into the cell not involving endocytosis. In detail, studies on the mechanism of transport using sulfated polyglycerol of molecular weight below 20 kDa provided evidence for an influx pump for organic anionic macromolecules which was not known so far. The influx pump is specifically present in proliferating and activated cells.

Polymers or dendrimers of employing polyanionic character in the physiological pH range can be sulfonates, sulfates, phosphonates, phosphates, carboxylates. Synthetic introduction of these groups to macromolecules is versatile; a reasonable way is to convert hydroxy groups of a polyol into sulfates giving polysulfates. The reaction conditions determine the degree of conversion (details see below). Sulfated polyglycerol was first described as a novel class of polyanionic macromolecules by Türk et al. (Bioconjugate Chemistry 15, 2004, 162-167). WO 2008/015015 describes different substances found to inhibit coagulation. From this prior art publication, there is no hint for intracellular localization and selective binding to NF-kappaB and AP-1, and inhibition of TGF-beta release.

Polyanionic dendrimers based on Polyamidoamine (PAMAM) or polylysine backbone coupled to disulfonated naphthalene is known as microbicide drug candidate for HIV prevention (McCarthy et al., Molecular Pharmaceutics 2005, 2, 312-318; Witvrouw et al., Molecular Pharmacol. 2000, 58, 1100-1108). The compounds target receptors on cell membranes of virus particles. It cannot be derived from these data that intracellular targets can be reached in human cell lines. At a concentration of 2500-fold above the concentration of the ED50, cell permeation was observed, which indicates unspecific mechanism of cell infiltration.

In addition, it was surprisingly found that polyanionic polyols are suited to deliver diagnostic and therapeutic effector molecules into the target cell and thus serve as carrier of therapeutic drugs. WO93018793 described the preparation of polyanionic drug conjugates for the delivery to endothelial cells. The examples outlined in WO93018793 are related to preparation of heparin drug conjugates for the use of targeted delivery of endothelial cells. Evidence is provided that heparin drug conjugates bind onto the endothelial cell membrane. No information is provided that heparin drug conjugates are suited to deliver drugs to the cytoplasm of endothelial cell. In line with WO93018793 the inventors found that heparin does not cross the cell membrane in relevant concentration and does not deliver diagnostic effectors into the cell. Heparin has a molecular weight in the range of 7 kDa to 30 kDa which is below the size necessary for endocytotic intracellular uptake. In addition, the experimental results of the present invention thereby confirm the failure of heparin to localize inside the cell (example 8 of the present invention).

More specifically, therapeutic effectors with respect to the present invention are molecules which can either directly or indirectly induce inhibitory or toxic effects to the target cell. Therapeutic effectors that bind to a certain intracellular target which is indispensible for proliferation and activation represent a direct effector. The inventors surprisingly found that polyanionic polyols out of the class of sulfated polyglycerols exhibit a strong and long-lasting accumulation inside the cell due to the strong binding to NF-kappaB and AP-1 (example 8). In contrast, polyols without sulfate groups are rapidly eliminated from the cytoplasm of the cell after stop of incubation (example 7). In summary, the inventors surprisingly found that polyanionic polyols bind with high affinity to intracellular target molecules thus preventing rapid elimination. This surprisingly found property demonstrates that a plurality of sulfate groups linked to a polyol-based carrier backbone exhibit a direct therapeutic effect, hence sulfate groups are direct effectors according to the invention. The inventors demonstrated that these effectors against NF-kappaB inhibit very effectively the synthesis of TGF-beta (example 10). As TGF-beta is a main mediator in autoimmune disease, sepsis, SIRS, fibrosis, cancer and cardiovascular disease, an ultimate therapeutic effect can be observed.

Based on the properties identified and described above, sulfated polyols were found to be optimally suited for the delivery of additional diagnostic and therapeutic effector molecules into the cell. These indirect therapeutic effectors with respect to the present invention are molecules which can induce additional inhibitory or toxic effects to the target cell independent of the inhibition of the activity of NF-kappaB and AP-1. A particular property of polyanionic polyols is therefore to deliver therapeutic and diagnostic effectors into the cell that show an accumulation and uptake into the cells, which is lasting longer than the respective therapeutic and diagnostic molecules alone. The therapeutic and diagnostic molecules are conjugated covalently to the sulfated polyol out of the class of polyglycerol thus yielding a conjugate between sulfated polyglycerol and therapeutic and diagnostic effector.

In view of the findings outlined above, the invention comprises therefore the use of polyanionic macromolecules for targeting of intracellular molecules involved in proliferation and protein synthesis of activated cells. In particular aspect, multiple sulfate groups linked to a polyol are specifically targeted to the cytoplasm and nucleus of proliferating and activated cells. The targeting was found to be fundamentally different to the known cellular uptake mechanism of endocytosis and to the uptake of macromolecules known to occur into every cell type. The invention demonstrates polyanionic macromolecules to be effective at molecular weights below endocytosis pathways and to be selective for the activated and proliferating cell (example 8 and example 9).

A skilled person understands an activated cell as a cell with increased metabolic activity. Activated cells can be characterized by the MTT-assay. In addition, cell activation can be demonstrated by detection of different inflammatory cytokines in the supernatants of different cell types such as isolated peripheral blood mononuclear cells or hematopoetic cell lines. According to the invention, activated cells comprise therefore cells of the immune system or tumor cells. Cells of the immune system can be for example monocytes, macrophages, or lymphocytes.

Based on the findings described above, the invention comprises the use of compounds of the general formula:

$P(OSO_3^-M^+)_n(L-G-E)_m$ with P=macromolecule wherein a number of hydroxyl groups is substituted by sulfate groups $OSO_3^-M^+$, the number of sulfate groups being preferably n>10, M=cationic inorganic or organic counter ion to the anionic sulfate group, E=therapeutic or diagnostic effector molecule, L=linker or spacer between P and E, G=reactive group for the attachment between L and E, m=0-100.

In a preferred embodiment, the invention comprises the use of compounds of the general formula $P(OSO_3^-M^+)_n(L-G-E)_m$ with P=polyol wherein a number of hydroxy groups is substituted by sulfate groups $OSO_3^-M^+$, the number of hydroxyl groups being preferably n>10, M=cationic inorganic or organic counter ion to the anionic sulfate group, E=therapeutic or diagnostic effector molecule, L=linker or spacer between P and E, G=reactive group for the attachment between L and E, m=0-100.

In a more preferred embodiment, the invention comprises the use of compounds of the general formula $P(OSO_3^-M^+)_n(L-G-E)_m$ with P=polyglycerol wherein a number of hydroxyl groups is substituted by sulfate groups $OSO_3^-M^+$, the number of sulfate groups being preferably n>10, M=cationic inorganic or organic counter ion to the anionic sulfate group, E=therapeutic or diagnostic effector molecule, L=linker or spacer between P and E, G=reactive group for the attachment between L and E, m=0-100.

Polyanionic polyols with covalently attached therapeutic or diagnostic effector molecules are new and have not been described before. Therefore, the invention comprises compounds of the general formula:
$P(OSO_3^-M^+)_n(L-G-E)_m$ with P=polyol wherein a number of hydroxyl groups is substituted by sulfate groups $OSO_3^-M^+$, the number of sulfate groups being preferably n>10, M=cationic inorganic or organic counter ion to the anionic sulfate group, E=therapeutic or diagnostic effector molecule, L=linker or spacer between P and E, G=reactive group for the attachment between L and E, m=1-100.

Polyanionic polyols with covalently attached linker units for the covalent conjugation with therapeutic or diagnostic effector molecules are new and have not been described before Therefore, the invention comprises compounds of the general formula:
$P(OSO_3^-M^+)_n(L-G)_m$ with P=polyol wherein a number of hydroxyl groups is substituted by sulfate groups $OSO_3^-M^+$, the number of sulfate groups being preferably n>10, M=cationic inorganic or organic counter ion to the anionic sulfate group, E=therapeutic or diagnostic effector molecule, L=linker or spacer between P and E, G=reactive group for the attachment between L and E, m=1-100.

In a more preferred embodiment, the invention comprises compounds of the general formula $P(OSO_3^-M^+)_n(L-G-E)_m$ with P=polyglycerol wherein a number of hydroxyl groups is substituted by sulfate groups $OSO_3^-M^+$, the number of sulfate groups being preferably n>10, M=cationic inorganic or organic counter ion to the anionic sulfate group, E=therapeutic or diagnostic effector molecule, L=linker or spacer between P and E, G=reactive group for the attachment between L and E, m=1-10.

Sulfated polyglycerols with covalently attached linker units for the covalent conjugation with therapeutic or diagnostic effector molecules are new and have not been described before Therefore, the invention comprises compounds of the general formula:
$P(OSO_3^-M^+)_n(L-G)_m$ with P=polyglycerol wherein a number of hydroxyl groups is substituted by sulfate groups $OSO_3^-M^+$, the number of sulfate groups being preferably n>10, M=cationic inorganic or organic counter ion to the anionic sulfate group, L=linker or spacer for the covalent attachment between P and E, G=reactive group for the attachment between L and E, m=1-100.

The possible number of sulfate groups n depends of the molecular weight of the macromolecule. As a particular embodiment, the macromolecule is based on polyglycerol which consists of repeated units of glycerol units for which each unit enables one OH group in the macromolecule. For example, a polyglycerol core of 10,000 g/mol enables 135 OH groups, a polyglycerol core of 2,000 g/mol enables 27 OH groups calculated for a theoretical monodisperse molecule (see further explanation below).

In a more detailed description of the embodiment, the compounds according to the invention are sulfated polyglycerols that comprise a) a polymeric polyglycerol core, composed of repeated units of glycerol with the formula $(RO-CH_2)_2CH-OR$ on a multifunctional starter molecule, which is a polyhydroxy compound having 1 to 1,000 OH groups, preferably 1 to 4 OH groups, wherein R is H or further glycerol units, the core having a branching degree of 0 to 67%, preferably 20 to 67%, more preferably above 60%, an average molecular weight of 500 to 1,000,000 g/mol, preferably 2,000 to 20,000 g/mol, more preferably 4,000 to 15,000 g/mol; most preferably 7,000 to 10,000 g/mol b) the substitution of a plurality of OH groups of the glycerol units with $-OSO_3H$ or $-OSO_3^-M^+$, so that the number of $-OSO_3H$ or $-OSO_3^-M^+$ groups is above 16, and a degree of sulfation X of 30 to 100% is obtained, with $M^+$ being a cationic inorganic or organic counter ion.

c) a resulting average molecular weight of the sulfated polyglycerol 1,000 to 5,000,000 g/mol, preferably 4,000 to 50,000 g/mol, more preferably 6,000 to 30,000, most preferably 10,000 to 20,000 g/mol.

"Branching degree" according to this invention means the degree of branching obtained by the reaction of both available OH groups of a glycerol unit with two further monomer molecules during the polymerization process (glycidol in case of the anionic polymerization). A branching degree of 0 describes a fully linear polyglycerol, with no glycerol units attached to both OH groups of a glycerol unit. A branching degree of 67% (⅔) is the theoretically achievable maximum for highly branched polyglycerols and means that all OH groups of a glycerol unit have reacted with two further glycerol units. According to the present invention polymeric polyglycerol cores with a branching of 20 to 67% are used. Preferably, highly branched structures are used, preferably with a branching degree of 30 to 67%, more preferably 50 to 67%, particularly preferably with a branching degree above 60%.

The polymeric polyglycerol core is produced by using a (multi)functional starter molecule or initiator, respectively, during the ring-opening polymerization of glycidol. The starter molecule or initiator, respectively, is a polyhydroxy compound, having 1 to 1,000, preferably 1 to 100 and more preferably 1 to 10, most preferably 1 to 4 OH groups. The starter molecule has the generic formula $R—(OH)_x$, wherein R can be any molecule, which is stable under the conditions of the anionic polymerization, and x is 1 to 1,000; preferably 1 to 100 and more preferably 1 to 10, most preferably 1 to 4. Preferably the used initiators are tris- or tetrafunctional initiators, such as 1,1,1-trishydroxymethylpropane (TMP) or 1,1,1-trishydroxymethylethane (TME) as preferred trisfunctional initiator or pentaerythrol (PE) as preferred tetrafunctional initiator. The starter molecule or the initiator, respectively, can carry further functional groups, such as particularly SH groups, $NH_2$ groups. In a particular embodiment the starter molecule contains OH groups and/or further heterofunctionalities (like SH, $NH_2$ derivatized with suited protecting groups). Another starter molecule can be a small polymeric polyglycerol with more than 3, preferably above 10, more preferably above 20 OH groups. Further suitable initiators, heterofunctionalities and protecting groups are known to the person of skill in the art.

The term "polyglycerol core" according to the present invention describes the polymeric molecules consisting of the repeating units of glycerol with the formula (RO—$CH_2)_2CH$—OR on generated by the polymerization process a multifunctional starter molecule. Hence, the core includes only free hydroxyl groups and the elements C, H, O. The core molecular weight can be determined by e.g. mass spectroscopy (MALDI). The core is subjected to further derivatizations or functionalizations leading to the inventive compounds. These functionalizations include the sulfation using suited reagents known to persons skilled in the art, or include the covalent attachment of linker molecules. Preferably a complex of $SO_3$ and pyridine is used as sulfation reagent. This reagent converts a —OH group into a —$OSO_3H$ or —$OSO_3^-$$Na^+$-group. Said sulfation reagent is preferably used in a concentration which corresponds to the desired sulfation degree. This means that the sulfation reagent is used in a concentration equimolar or of higher molar equivalents relative to the OH groups of the polymeric polyglycerol core to be converted. The resulting functionalization, i.e. sulfation, can thus be adjusted via the ratio of $SO_3$ to the OH groups of the polyglycerol.

"Degree of sulfation" according to this invention means the percentage of functionalized (sulfated) OH groups of the glycerol units of the polymeric polyglycerol core relative to the number of overall OH groups. The functionalization results either from the substitution of one or more OH groups of the glycerol units with —$OSO_3H$ or —$OSO_3^-M^+$ groups or from the attachment of an oligomeric spacer carrying —$OSO_3H$ or —$OSO_3^-M^+$ groups at one or more OH groups of the glycerol units.

The cationic counter ion $M^+$ is selected from the group of inorganic alkali metals sodium, potassium, lithium, calcium, or from organic cationic compounds meglumine, lysine, glycine, or mixtures thereof. Preferred is sodium leading to —$SO_3^-Na^+$ groups.

For polyols, in particular polyglycerols, the present invention provides data that the parameter of molecular weight of the polymer as well as the degree of sulfation of the hydroxyl groups is important for the improvement of binding affinity to intracellular targets. Surprisingly, it was found that both the increase of the degree of sulfation and the increase of molecular weight increases the binding affinity to NF-kappaB. This increase was not expected and is a strong indication of a new property of the molecule. Preferred sulfated polyglycerols are therefore polyglycerols of molecular weights of the core at above 3,000 g/mol, more preferably above 6,000 g/mol, even more preferably above 10,000 g/mol. The preferred degree of sulfation is above 38%, more preferably above 50%, even more preferably above 76%, most preferred above 86% and even most preferred above 90%. The preferred values and maximal achievable degree of 100% is understood to be based on a general standard error of measurement by elementary analysis of the sulfur at +/−5%.

Depending on the choice of the initiator and the polymerization conditions the polymeric polyglycerol core reaches a branching degree and an arbitrarily adjustable mean molecular weight, which is not a defined molecular weight but a distribution covering a molecular weight range. This so called polydispersity can be described by the polydispersity index (PDI). The PDI is defined as $M_w/M_n$, with $M_w$ being the weight average molecular mass, and $M_n$ being the number average molecular mass. Preferred polydispersity indices of the highly sulfated polyglycerols are below 2.3, more preferred below 1.8, most preferred below 1.5. The average molecular weights used for the description of the polyglycerol cores are the number average molecular mass $M_n$.

Sulfation reactions are known to persons skilled in the art as described above. Sulfation is achieved preferably by using sulfurtrioxide complexes (pyridinium-$SO_3$, trimethylamine-$SO_3$, triethylamine-$SO_3$, dimethylformamide-$SO_3$). Sulfation is performed either on isolated polyglycerol, or subsequently after the polymerization in one step by adding the sulfation reagent directly into the polymerization reactor. This one-step procedure to obtain sulfated polyglycerol according to the invention is new and has not been described before. The degree of sulfation was improved over the state of the art by modifying the sulfation conditions. A 1.2-fold excess of sulfation reagent combined with a maintained reaction temperature of above 80° C., preferably above 90° C. for at least 18 h reaction time, is suited to obtain sulfation degrees above 85%. Surprisingly, no decomposition and by-products were detected.

It was found surprisingly, that additional linker units attached to the macromolecule, demonstrated for sulfated polyglycerol, do not hamper the inventive mode-of-action and use of the compounds. In example 11 is shown that modification with linker leads to binding affinity to NF-kappaB at an identical $IC_{50}$ value compared to sulfated polyglycerol without linker. Using the synthetic approach of linker modification followed by the sulfation and the deprotection step to yield derivatives with reactive functional groups, it was shown that an efficient covalent conjugation to diagnostic and/or therapeutic effector molecules is possible. WO2008/

015015 claims polyglycerol sulfates with signalling molecules, however, does not teach detailed synthetic information to obtain such conjugates via a reasonable linker modification and does not exemplify said conjugates.

WO2008/015015 does not provide chemical detail on signalling molecules and technical solutions on how to be applied. Moreover, the type of synthetic chemistry substantiating the used term "loaded" or "bound to" is not provided and is unclear.

The linker unit L is an alkyl carrying a functional group attached to at least one of the OH groups, with the functional group G being potentially able to be conjugated with an additional therapeutic or diagnostic effector molecule E. According to the invention, the linker is attached to at least one OH group thereby forming an ether, carboxyl ester, sulfonyl ester, carbamate, thiocarbamate, urea, thiourea, triazole bond. Polyglycerol sulfates with additional linkers according to the invention are new and have not been described before.

In a more detailed description of the embodiment, the compounds according to the invention are therefore sulfated polyglycerols with linkers $P(OSO_3^-M^+)_n(L-G)_m$ that comprise a) a polymeric polyglycerol P, composed of repeated units of glycerol with the formula $(RO—CH_2)_2CH—OR$ on a multifunctional starter molecule, which is a polyhydroxy compound having 1 to 1,000 OH groups, preferably 1 to 4 OH groups, wherein R is H or further glycerol units, the core having a branching degree of 0 to 67%, preferably 20 to 67%, more preferably above 60%, an average molecular weight of 500 to 1,000,000 g/mol, preferably 2,000 to 20,000 g/mol, more preferably 4,000 to 15,000 g/mol; most preferably 7,000 to 10,000 g/mol.

b) the substitution of a plurality of OH groups of the glycerol units with $—OSO_3H$ or $—OSO_3^-M^+$, with a preferred number of $—OSO_3H$ or $—OSO_3^-M^+$ groups being above 10, and a degree of sulfation X of 30 to 100% is obtained, with $M^+$ being a cationic inorganic or organic counter ion.

c) a resulting average molecular weight of the sulfated polyglycerol 1,000 to 5,000,000 g/mol, preferably 4,000 to 50,000 g/mol, more preferably 6,000 to 30,000, most preferably 10,000 to 20,000 g/mol.

d) a linker unit L carrying a functional group G, attached to at least one of the OH groups up to maximal 100-X % of the OH groups, with the functional groups being potentially able to be conjugated with an additional therapeutic or diagnostic effector molecule, wherein X is the degree of sulfation.

Preferred are sulfated polyglycerols of the formula (I), (II) or (III),

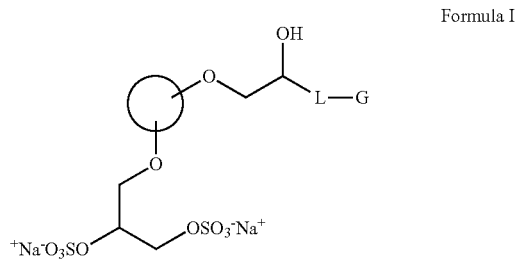

Formula I

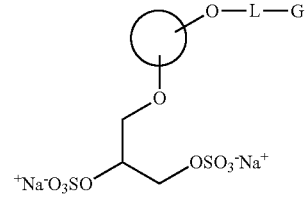

Formula II

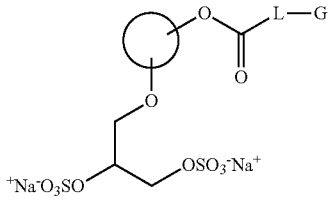

Formula III wherein L is a branched or linear $C_{1-20}$-alkyl group in which one or more (preferably one to three) non-consecutive methylene groups may be replaced by a group selected from the group comprising O, S, NH, C(O)NH, C(O), $SO_2$, SO, aryl, ethene or ethyne, and wherein G is selected from the group comprising —OH, $—OSO_3H$, $—OSO_3Na$, $—NH_2$, $—N_3$, —COOH, —SH, $—SO_3^-$, —C≡C, wherein —OH, $—NH_2$, —SH, —COOH can be or remain functionalized with protecting groups known to the skilled person.

The formula illustrates the chemical structure of one linker unit for simplification and shows the sulfated polyglycerol as sketch (bulb) with two sulfate groups at a glycerol subunit drawn by way of example. It is understood that derived from the respective degree of sulfation, other glycerol subunits can carry free hydroxyl groups beside sulfate groups. According to the invention linker units can be attached to at least one OH group up to maximal 100-X % of the OH groups, wherein X is the degree of sulfation.

The linker-modified sulfated polyglycerols can be applied to covalently attach diagnostic and/or therapeutic effector molecules to the polymer and transport the effector molecules to the target site. According to the invention, these effector molecules are indirect effectors, whereas the plurality of sulfates are direct effectors, as described above. It was shown that the conjugation with diagnostic effector molecules leads to an accumulation in the target tissues giving proof of a target-specific uptake. In example 8 and 9 is shown that sulfated polyglycerol with a diagnostic effector molecule out of the class of fluorescent cyanine dyes leads to improved transport and binding of the dye in the cell compared to the low molecular weight dye conjugated only to one triglycerol unit (ICC-triglycerol). Thus, linker-modified sulfated polyglycerols are a surprisingly identified inventive class of compounds, which provide indirect therapeutic efficacy based on the ability to covalently attach diagnostic and/or therapeutic effector molecules to the polymer. The synthesis of diagnostic conjugates are further described in the examples 2-5.

Furthermore, macromolecular therapeutic compounds can be used for the target-specific delivery of molecules exhibiting indirect therapeutic effects according to the invention. The state-of-the-art describes various conjugates based on macromolecules (Nori et al., Adv Drug Deliv Rev. 57: 609, 2005, Haag et al., Angew. Chem. Int. Ed. 45: 1198, 2006). Macromolecules carrying a plurality of sulfates together with therapeutic effector molecules, especially sulfated polyglycerols carrying such effector molecules, are not known in the literature. Examples 6 and 17 demonstrate that covalent attachment to therapeutic effector molecules out of the class of cytostatics and siRNA induce improved therapeutic effects through the inventive mode-of-action of intracellular uptake, and binding to transcription factors NF-kappaB and AP-1, and inhibition of TGF-beta synthesis.

In a more detailed description of the embodiment, the compounds according to the invention are therefore sulfated polyglycerol conjugates with diagnostic or therapeutic effector molecules according to the formula $P(OSO_3^-M^+)_n(L\text{-}G\text{-}E)_m$, comprising a) a polymeric polyglycerol P, composed of repeated units of glycerol with the formula $(RO\text{---}CH_2)_2CH\text{---}OR$ on a multifunctional starter molecule, which is a polyhydroxy compound having 1 to 1,000 OH groups, preferably 1 to 4 OH groups, wherein R is H or further glycerol units, the core having a branching degree of 0 to 67%, preferably 20 to 67%, more preferably above 60%, an average molecular weight of 500 to 1,000,000 g/mol, preferably 2,000 to 20,000 g/mol, more preferably 4,000 to 15,000 g/mol; most preferably 7,000 to 10,000 g/mol b) the substitution of a plurality of OH groups of the glycerol units with $-\!OSO_3H$ or $-\!OSO_3^-\ M^+$, with a preferred number of $-\!OSO_3H$ or $-\!OSO_3^-M^+$ groups being above 10, and a degree of sulfation X of 30 to 100% is obtained, with $M^+$ being a cationic inorganic or organic counter ion.

c) a resulting average molecular weight of the sulfated polyglycerol 1,000 to 5,000,000 g/mol, preferably 4,000 to 50,000 g/mol, more preferably 6,000 to 30,000, most preferably 10,000 to 20,000 g/mol.

d) a linker unit L carrying a functional group G, attached to at least one of the OH groups up to maximal 100-X % of the OH groups, with the functional groups being potentially able to be conjugated with an additional therapeutic or diagnostic effector molecule, wherein X is the degree of sulfation.

e) a diagnostic and/or therapeutic effector molecule covalently attached to one up to the maximal possible number of said functional groups, the diagnostic effector molecule being selected from the group of fluorescent dyes or chelators for radioactive or paramagnetic metals, and the therapeutic effector molecules being selected from the group of cytostatics, anti-angiogenetic drugs, photosensitizers, siRNAs.

Preferred are therefore derivatives with linker units L employing a heteroatom functionalization G covalently reacted with diagnostic and/or therapeutic effector molecules E, illustrated by the formula (IV), (V) or (VI),

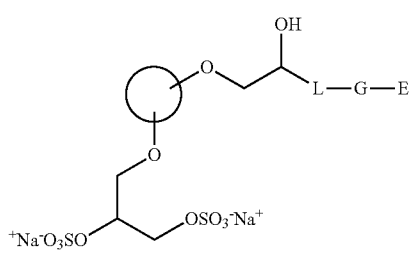

Formula IV

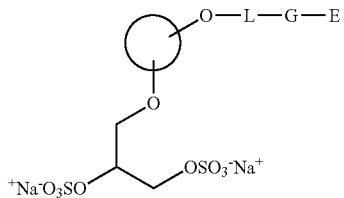

Formula V

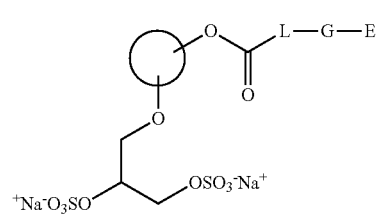

Formula VI

Branching degree, degree of sulfation and the linker unit is described above and used here accordingly. The illustration of sulfated polyglycerol as bulb is described above.

According to the invention, diagnostic effector molecules are selected from the group of fluorescent dyes or chelators with radioactive or paramagnetic metals, and therapeutic effector molecules are selected from the group of cytostatics, anti-angiogenetic drugs, photosensitizers, siRNAs.

As effector molecule with diagnostic function (E) selected from the group of fluorescent dyes, the molecules comprise a fluorescent dye with a fluorescence emission in the UV/visible (400-800 nm) or near-infrared (700-1000 nm) spectral range. Preferably, the optical effector molecule with diagnostic function is selected from the group comprising NBD, fluoresceins, rhodamines, perylene dyes, croconium dyes, squarylium dyes, polymethine dyes, indocarbocyanine dyes, indodicarbocyanine dyes, indotricarbocyanine dyes, merocyanine dyes, phthalocyanines, naphthalocyanines, triphenylmethine dyes, croconium dyes, squarylium dyes, benzophenoxazine dyes, benzophenothiazine dyes, and derivatives thereof. More preferably, the optical effector molecule with diagnostic function is selected from the group comprising polymethine dyes, indocarbocyanine dyes, indodicarbocyanine dyes, indotricarbocyanine dyes, merocyanine dyes, phthalocyanines, naphthalocyanines, triphenylmethine dyes, croconium dyes, squarylium dyes, and derivatives thereof. Even more preferably, the optical effector molecule with diagnostic function is selected from the group comprising indocarbocyanine, indodicarbocyanine, indotricarbocyanine dyes and derivatives thereof. Examples are Cy7, Cy5.5, Cy3, AlexaFluor Dyes, indocyanine green (ICG). Examples of synthesis routes leading to optical effector molecules with diagnostic function which may be used in accordance with the present invention are published in "Topics in Applied Chemistry: Infrared absorbing dyes" Ed. M. Matsuoka, Plenum, N.Y. 1990, "Topics in Applied Chemistry: The Chemistry and Application of Dyes", Waring et al., Plenum, N.Y., 1990, J. Org. Chem. 60: 2391-2395 (1995), Lipowska et al. Heterocyclic Comm 1 427-430 (1995), Fabian et al. Chem. Rev. 92: 1197 (1992), WO 96/23525, Strekowska et al. J. Org. Chem. 57: 4578-4580 (1992), Bioconjugate Chem. 16:1275-128 (2005), Lee et al., J. Org. Chem. 73: 723 (2008).

Figure 20:
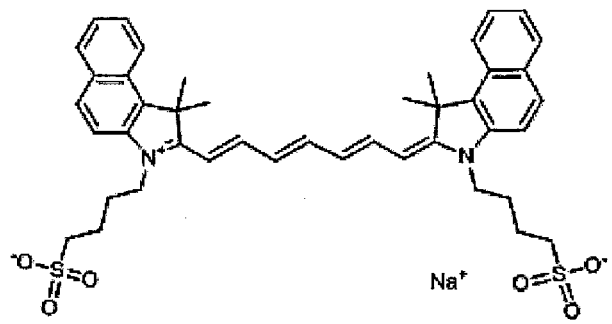
FIG. 20 depicts chemical structures of ICG (FIG. 20a), ICG analogs according to the invention (FIG. 20b) and structures of preferred derivatives used as diagnostic effector molecules (FIG. 20c-d).
Figure 20:
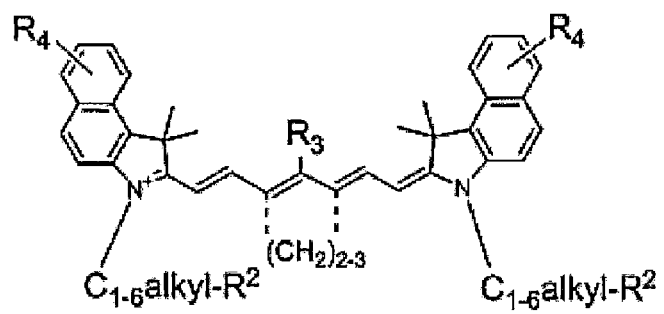
Figure 20:
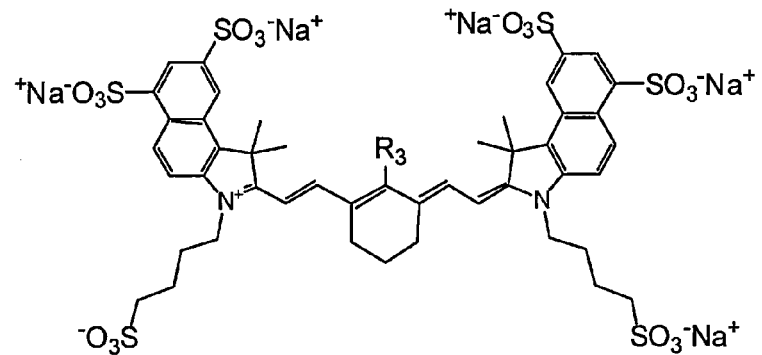
Figure 20:
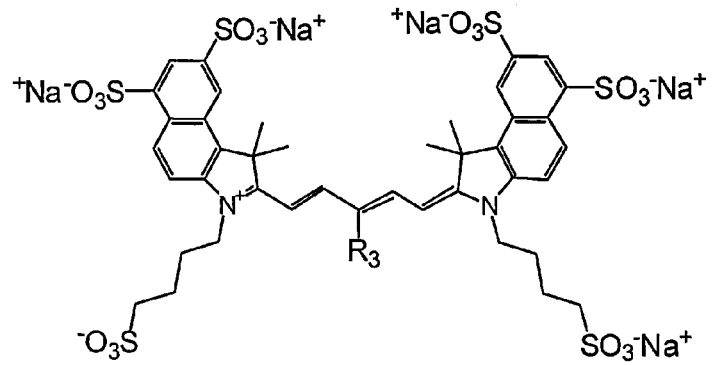

Most preferably, the optical effector molecule with diagnostic function is a fluorescent dye comprising the structural elements of indocyanine green (ICG) and derivatives thereof, according to FIG. 20. Hereby, the derivatives of ICG are preferably structurally described by a) optional replacement of one or two sulfobutyl chains at the indol nitrogen by $-\!C_{1\text{-}6}\text{-alkyl-}R^2$, whereby $R^2$ is $-\!OH$, $-\!COOH$, $-\!OSO_3H$, $-\!OSO_3Na$, $-\!NH_2$, $-\!N_3$, $-\!COOH$, $-\!SH$, or $-\!C\!\!\equiv\!\!C$, and/or b) replacement of the polymethine chain by a substituted polymethine chain with a residue $R^3$ at the central carbon atom, whereby the two adjacent carbons atoms may form a 5- or 6-membered ring together with the three carbon atoms of the polymethine chain, whereby $R^3$ is selected from the group comprising —$C_{1-6}$-alkyl-$R^2$, —S—$C_{1-6}$-alkyl-$R^2$, —O—$C_{1-6}$-alkyl-$R^2$, -phenyl-$C_{1-6}$alkyl-$R^2$, -phenyl-$R^2$, —S-phenyl-$C_{1-6}$alkyl-$R^2$, —S-phenyl-$R^2$, —O-phenyl-$C_{1-6}$alkyl-$R^2$, —O-phenyl-$R^2$, -phenyl-NH—$C_{1-6}$alkyl-$R^2$, -phenyl-NH$R^2$, —S-phenyl-NH—$C_{1-6}$alkyl-$R^2$, —S-phenyl-NH$R^2$, —O-phenyl-NH—$C_{1-6}$alkyl-$R^2$, —O-phenyl-NH$R^2$, whereby $R^2$ is as described above and whereby 1-2 carbon atoms of the $C_{1-6}$alkyl may be replaced by a carbonyl group, and/or c) substitution of the exterior benzindol rings with one or more groups $R^4$ independently selected from —$SO_3^-$Na$^+$, —COOH or —OH.

It is more preferred that the polymethine chain has a residue $R^3$ as described above at the central carbon atom, $R^4$ is H or stands for one or two —$SO_3^-$Na$^+$ groups, wherein $R^2$ is —COOH or —$SO_3^-$Na$^+$, and wherein the two adjacent carbons atoms may form a 5- or 6-membered ring together with the three carbon atoms of the polymethine chain (FIG. 20b).

A most preferred derivative of ICG is defined according to FIG. 20c with a residue $R^3$ being —S—CH$_2$—CH$_2$—COOH, -phenyl-COOH, -phenyl-CH$_2$—COOH, -phenyl-CH$_2$CH$_2$—COOH, -phenyl-CH$_2$CH$_2$CH$_2$—COOH, -phenyl-NH$_2$, -phenyl-NH(CO)—CH$_2$CH$_2$—COOH, -phenyl-NH(CO)—CH$_2$CH$_2$CH$_2$—COOH wherein the substitution at the phenyl is in para-position. An additional embodiment represents a derivative with pentamethine chain carrying the residue $R^3$ in the middle carbon (FIG. 17d).

Figure 5:
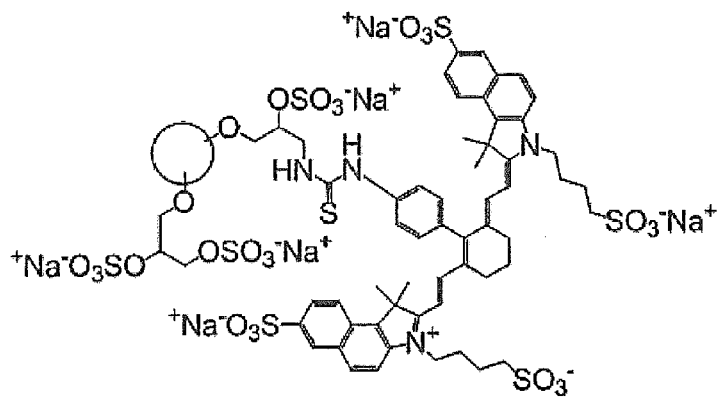
FIG. 5 depicts sulfated polyglycerol conjugates with diagnostic effector molecules out of the class of cyanine dyes according to example 3. The examples include a schematic representation of the macromolecular sulfated polyglycerol backbone (bulb) with a representative structural subunit of sulfated glycerol, and a subunit to which the linker and effector molecule is attached.
Figure 5:
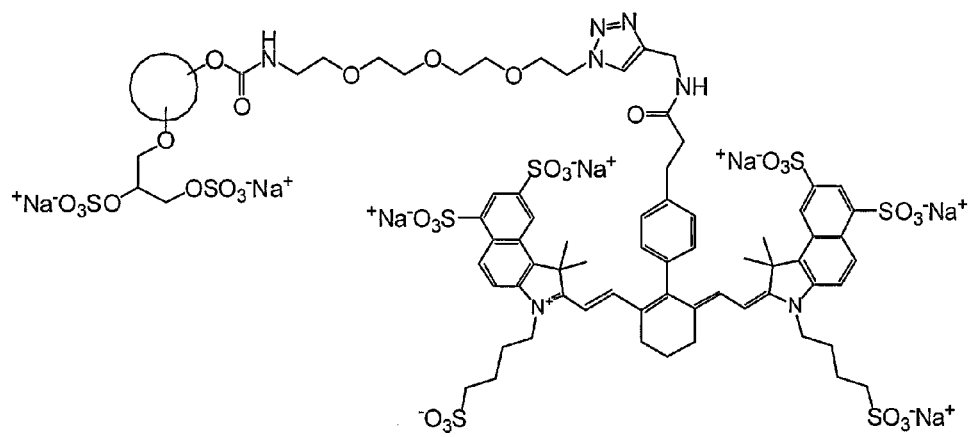
Figure 5:
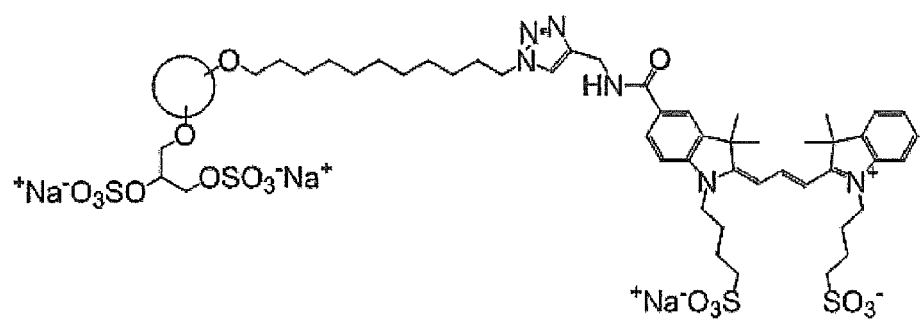

The most preferred derivative of ICG represents a derivative comprising 6 sulfonate groups together with a reactive linker according to FIG. 20c-d, thus providing highest hydrophilicity based on sulfonate groups. It was shown that labeling of IgG and Fab antibodies was possible at labeling ratios >3 without affecting the functionality of the antibody and without leading to precipitation of the conjugate. In contrast to these results, conjugates with ICG derivatives comprising 4 or less sulfonate groups are less stable in solution leading to precipitation and loss of function of the conjugates. The inventive cyanine dyes are used as effectors conjugated covalently to sulfated polyglycerol according to the invention (example 3, FIG. 5).

In yet another embodiment at least one of the effector molecules (E) is a radiolabeled complex comprising a radionuclide and a chelating structure selected from tetraazacyclododecane chelates and makrocyclic or open-chain aminocarboxylic acids. Preferably, the radiolabeled complex comprises a chelating agent selected from the group comprising 1,4,7,10-tetraazacyclododecane-N,N',N'',N'''-tetraacetic acid (DOTA), 1,4,7,10-tetraazacyclododecane-N,N',N''-triacetic acid (DO3A), 1-oxa-4,7,10-triazacyclododecane-N,N',N''-triacetic acid (OTTA), 1,4,7-triazacyclononane-N,N',N''-triacetic acid (NOTA), trans(1,2)-cyclohexanodiethylentriamine-pentaacetic acid (CDTPA), N,N,N',N'',N''-diethylentriamine-pentaacetic acid (DTPA), ethylenediamine-tetraacetic acid (EDTA), N-(2-hydroxy) ethylen-diamine triacetic acid, nitrilotriacetic acid (NTA), N,N-di(2-hydroxyethyl)glycine and derivatives thereof and a radionuclide selected from $^{90}$Y, $^{99m}$Tc, $^{111}$In, $^{47}$Sc, $^{67}$Ga, $^{51}$Cr, $^{177m}$Sn, $^{67}$Cu, $^{167}$Tm, $^{97}$Ru, $^{188}$Re, $^{177}$Lu, $^{199}$Au, $^{203}$Pb, $^{141}$Ce, $^{86}$Y, $^{94m}$Tc, $^{110m}$In, $^{68}$Ga, $^{64}$Cu. More preferably, the radiolabeled complex is selected from the group comprising 1,4,7,10-tetraazacyclododecane-N,N',N'',N'''-tetraacetic acid (DOTA), 1,4,7,10 tetraazacyclododecane-N,N',N''-triacetic acid (DO3A), N,N,N',N'',N''-diethylentriamine-pentaacetic acid (DTPA) and a radionuclide selected from $^{90}$Y, $^{99m}$Tc, $^{111}$In, $^{68}$Ga, $^{86}$Y, $^{64}$Cu. Even more preferably, the radiolabeled complex is selected from the group comprising 1,4,7,10-tetraazacyclododecane-N,N',N'',N'''-tetraacetic acid (DOTA) with one acetic acid modified to an amide using a reactive structure for covalent conjugation with G (Formula I-III), 1,4,7,10 tetraazacyclododecane-N,N',N''-triacetic acid (DO3A) with one nitrogen carrying hydroxyethyl moiety substituted with a reactive structure for covalent conjugation with G (Formula I-III), and a radionuclide selected from $^{111}$In, $^{68}$Ga, $^{86}$Y, $^{64}$Cu. It is understood that the radioisotopes can impart diagnostic function as well as therapeutic function, when selecting a radioisotope with therapeutically active radioemission, such as β-radiation emitting radionuclides. The complexation chemistry is principally identical and not depending on the type of radioemission. In the present invention, β-emitting radiotopes, preferably $^{90}$Y, are preferred. Radiolabeling for imaging and radiotherapy is known to the skilled person; see also in: Liu et al., Adv Drug Deliv Rev. 60: 1347, 2008; Zwanziger et al., Curr Pharm Des. 14: 2385, 2008; Maecke, Ernst Schering Res Found Workshop. 49: 43, 2005.

In yet another embodiment at least one of the effector molecules (E) is a complex comprising a paramagnetic metal and a complexing structure selected from tetraazacyclododecane chelates and makrocyclic or open-chain aminocarboxylic acids (Kobayashi et al., Curr Pharm Biotechnol. 5: 539, 2004). The invention describes the ability to couple up to 5 gadolinium complexes to a azide-modified sulfated polyglycerol (example 5). Such inventive conjugates are used as contrast agent for Magnetic Resonance Imaging (MRI), due to the high intracellular delivery of Gadolinium into activated cells. Thus, the paramagnetic metal is preferably Gadolinium (Gd$^{3+}$), and the complexing structure is selected from the group comprising 1,4,7,10-tetraazacyclododecane-N,N',N'',N'''-tetraacetic acid (DOTA) with one acetic acid modified to an amide using a reactive structure for covalent conjugation with G (Formula I-III), 1,4,7,10 tetraazacyclododecane-N,N',N''-triacetic acid (DO3A) with one nitrogen carrying hydroxyethyl moiety at substituted with a reactive structure for covalent conjugation with G (Formula I-III).

In yet another preferred embodiment the effector molecule (E) is an effector molecule with therapeutic function, comprising a photosensitizer with phototherapeutic efficacy after excitation in the UV/visible (400-800 nm) or near-infrared (700-1000 nm) spectral range (example 6a). More preferably, the photosensitizer is selected from the group comprising tetrapyrroles, porphyrins, sapphyrins, chlorins, tetraphenylporphyrins, tetraphenylchlorins, bacteriochlorins, tetraphenylbacteriochlorins, pheophorbides, bacteriopheophorbides, pyropheophorbides, bacteriopyropheophorbides, purpurinimides, bacteriopurpurinimides, benzoporphyrins, phthalocyanines, naphthalocyanines and derivatives thereof. Even more preferably, the photosensitizer is selected from the group comprising pheophorbide a, pyropheophorbide a, 3-acetylpheophorbide a, 3-acetylpyropheophorbide a, purpurin-18-N-alkylimide, purpurin-18-N-hydroxylimide, 3-acetylpurpurin-18-N-alkylimide, 3-acetylpurpurin-18-N-hydroxylimide, chlorine e6, Sn-chlorine e6, m-tetrahydroxyphenylchlorin (m-THLC) and benzoporphyrin derivative, benzoporphyrin derivative monoacid (BPD-MA, verteporfin). Yet even more preferably, the photosensitizer is selected from the group comprising pheophorbide a, pyropheophorbide a, 3-acetylpheophorbide a, 3-acetylpyropheophorbide a, purpurin-18-N-alkylimide, purpurin-18-N-hydroxylimide, 3-acetylpurpurin-18-N-alkylimide, 3-acetylpurpurin-18-N-hydroxylimide and chlorine e6, benzoporphyrin derivative, benzoporphyrin derivative monoacid (BPD-MA, verteporfin). Most preferably, the photosensitizer is selected from the group comprising pheophorbide a, pyropheophorbide a, purpurin-18-N-alkylimide, purpurin-18-N-hydroxylimide and chlorine e6, verteporfin.

Examples of synthesis routes leading to photosensitizers which may be used in accordance with the present invention are published in WO 2003/028628, US 2005/0020559, Zheng G et al, J Med Chem 2001, 44, 1540-1559; Li G et al., J. Med. Chem. 2003, 46, 5349-5359; Lunardi C N et al., Curr Org Chem 2005, 9, 813-821; Chen Y et al., Curr Org Chem 2004, 8, 1105-1134.

In yet another preferred embodiment optionally at least one of the effector molecules (E) is a therapeutic effector molecule of the class of antineoplastic agents such as alkylating and alkylating-like antineoplastic agents, e.g. cisplatin, carboplatin, oxaliplatin, mechlorethamine, cyclophosphamide, ifosfamid, trofosfamid, melphalan, chlorambucil, alkylsulfonate, busulfan, treosulfan, carmustin, lomustin, nimustin, estramustin, streptozotocin, procarbazin, dacarbazin, temozolomid, thiotepa, or a therapeutic effector molecule of the class of anti-metabolites such as purine analogues (6-thioguanin, pentostatin, azathioprin, 6-mercaptopurin, fludarabin, cladribin) or pyrimidine analogues (gemcitabin, 5-fluouracil) or antifolates (methotrexate), plant alkaloids and terpenoids such as vinca alkaloids (vincristine, vinblastine, vinorelbine, vindesine), disorazoles and derivatives (disorazole A1, A2, E1, Z), podophyllotoxin such as etoposide and teniposide, taxanes (docetaxel, paclitaxel), topoisomerase inhibitors such as camptothecin derivates irinotecan and topotecan, amsacrine, etoposide, etoposide phosphate, and teniposide, antitumour antibiotics such as dactinomycin, doxorubicin, daunorubicin, epirubicin, bleomycin, mitomycin.

Another class of therapeutic effector molecules are toxins such as abrin, alpha toxin, diphtheria toxin, exotoxin, gelonin, pokeweed antiviral protein, ricin, saponin and pseudomonas exotoxin.

Another class of therapeutic effector molecules are small-interfering-RNAs (siRNAs), e.g. VEGF or EGF siRNA. siRNA is preferably conjugated to polyglycerol-linker via cleavable bonds, such as disulfide bonds (example 6e and example 20).

Preferred are the therapeutic effector molecules paclitaxel and chlorambucil, its derivatives with functional groups suited for formation of covalent bonds with the macromolecule. Used according to the invention for the synthesis of conjugates are its precursor derivatives carrying reactive groups for covalent conjugation. Preferred groups are propargyl, carboxylic acid, carboxylic acid-NHS-ester, isothiocyanate, maleimide, Pyridinium-disulfide. Most preferred are paclitaxel-succinate-NHS-ester (Formula E28 in Table 1, Thierry et al., J. Am. Chem. Soc. 127: 1626, 2005) and Chlorambucil-NHS-ester (Formula E25, WO96/022303), paclitaxel-succinate-propargylamide (Formula E27), chlorambucil-propargylamide (Formula E24).

Hence, according to the invention, the effector molecule (E) is attached to the functional group (G) of at least one linker of the polyglycerol sulfate derivative thereby forming an ether, thioether, carboxylic ester, sulfonylester, amide, amine, carbamate, thiocarbamate, urea, thiourea, hydrazone, imine, disulfide, triazole, or vinyl bond.

A particular embodiment of the invention is a compound according to the formula $P(OSO_3^-M^+)_n(L-G)_m$, wherein L is —O—, m is a number >1, and G stands for $SO_3^-M^+$, thus giving a sulfate group. As described above, sulfate groups are a direct effector function when they are assembled in a plurality enabling the effect of uptake into activated and proliferating cells. M is preferably sodium.

According to the invention, the macromolecule is capable to transport the covalently attached effector molecules, as described above, into activated and proliferating cells. In the examples of the present invention is shown that the type of effector molecule can chosen without hampering the biological efficacy of the sulfated polyglycerol. It is an embodiment of the invention that sulfated polyglycerol is conjugated to 1-100 effector molecules. However, the overall molecular weight of effector molecules should not exceed the average molecular weight of the sulfated polyglycerol. Thus, it a preferred embodiment to have 1-10 effector molecules conjugated, more preferred 1-5 effector molecules. The resulting ratio of the average molecular weight of sulfated polyglycerol to the overall molecular weight of all effector molecules coupled to the sulfated polyglycerol is preferably 3, more preferably 5, even more preferably 10.

The solubility of sulfated polyglycerol in aqueous solution is high at >200 mg/mL. Lipophilic effector molecules, which are not soluble in aqueous media, are brought into solution via conjugation to sulfated polyglycerol. Surprisingly, the conjugate with paclitaxel (example 6b) exhibits solubility in water of >100 mg/mL. The resulting overall solubility of effector conjugates in water or in aqueous buffers (pH range 6.0 to 8.5) is therefore preferably >50 mg/mL, and more preferably >100 mg/mL.

Macromolecules with the assembly of a plurality of sulfate groups, shown for sulfated polyglycerols, bind the intracellular transcription factor NF-kappaB in IC50 values of below 10 nM (example 11) and inhibit TGF-β release (example 10). Accordingly, a preferred embodiment of the invention are sulfated polyglycerols as well as polyglycerols as conjugates with binding of NF-kappaB is better than an $IC_{50}$ of 50 nM, more preferably better than 20 nM, most preferably better than 10 nM in the binding assay described in example 11.

Preferred examples for reactive effector molecules as precursurs for covalent conjugation to macromolecules, in particular group G (Formula I-III) are depicted in Table 1:

E1

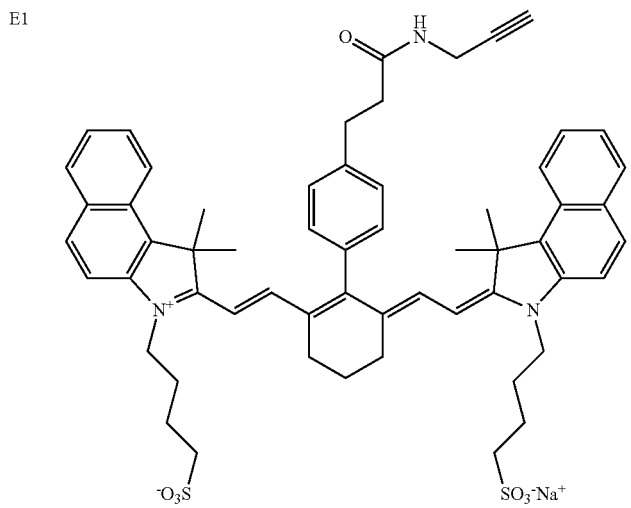

-continued
E2
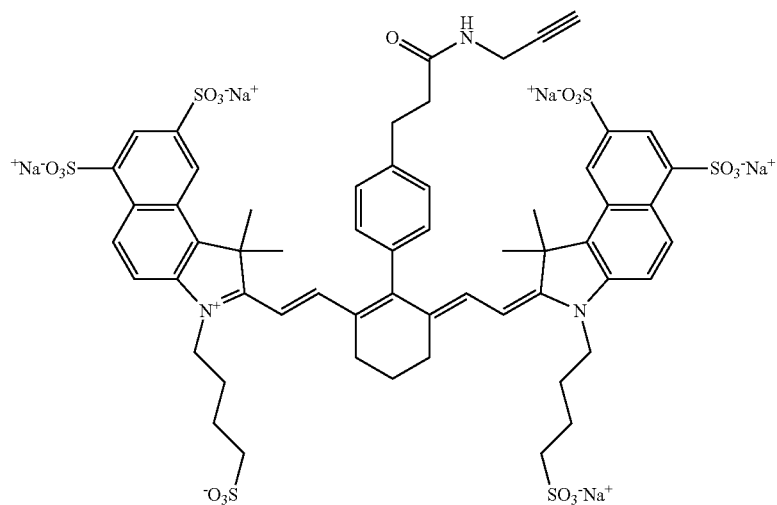
E3
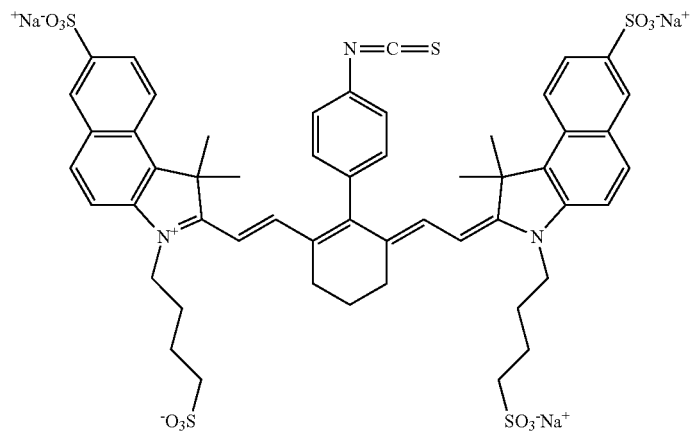
E4
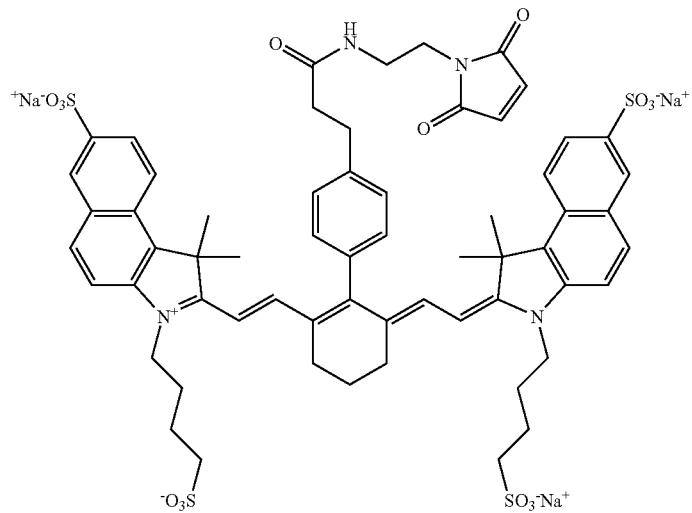

-continued
E5
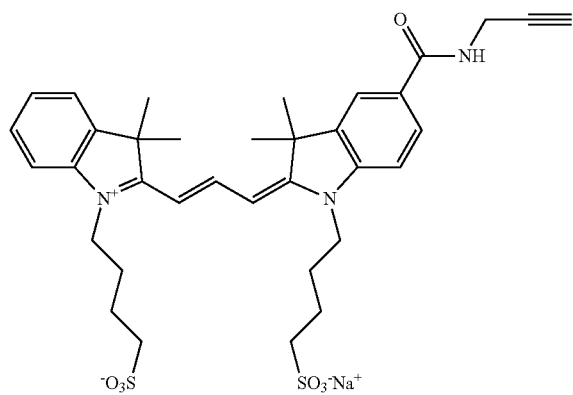
E6
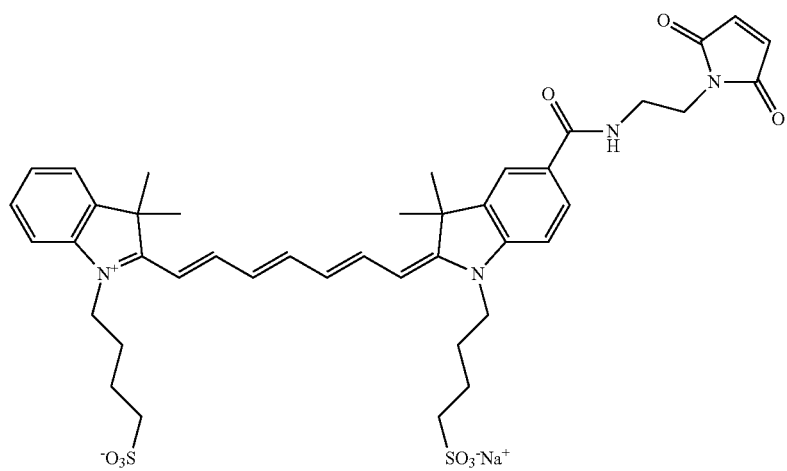
E7
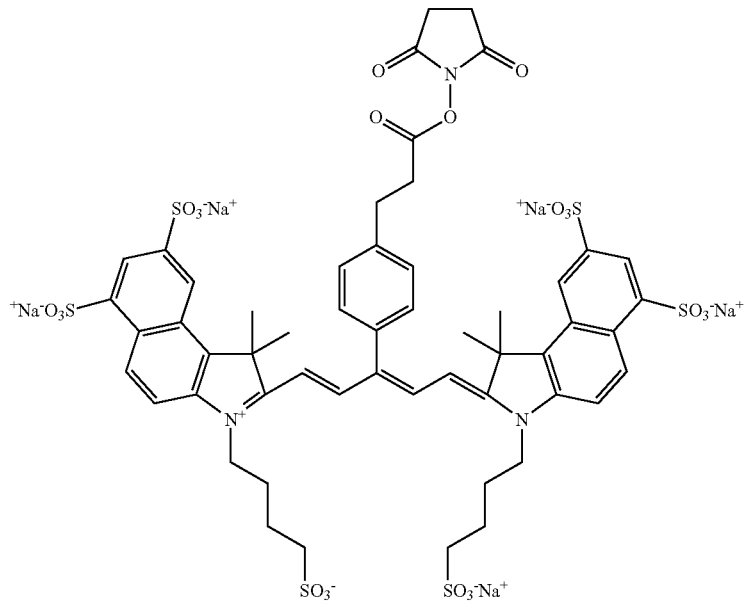

-continued
E8
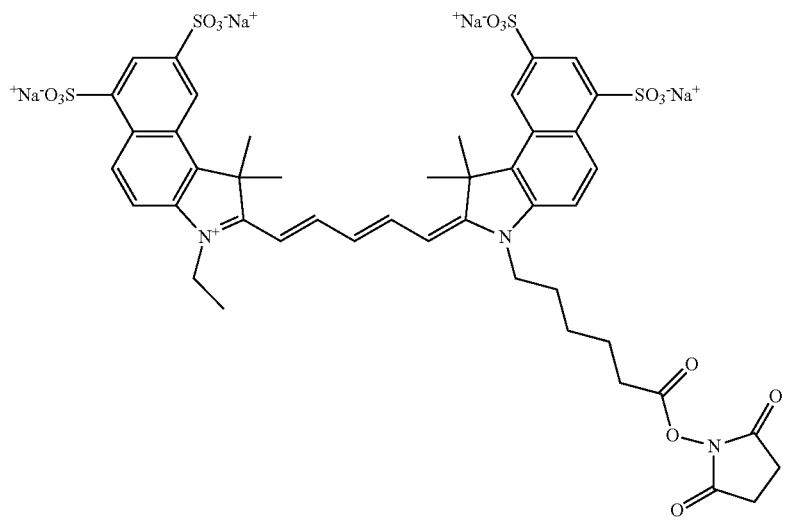
E9
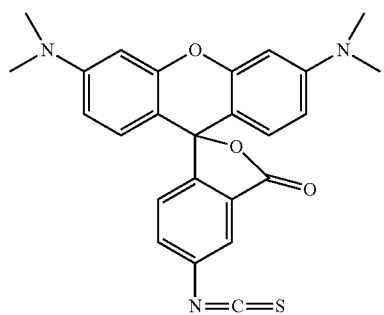
E10
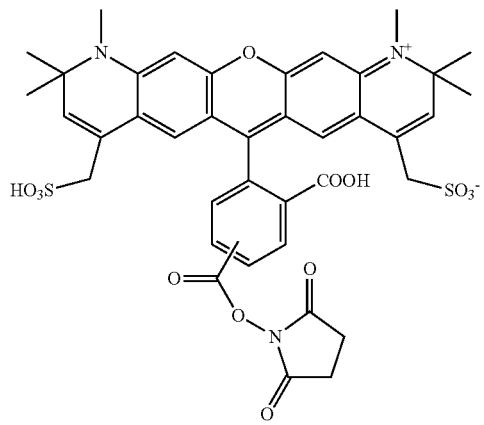
E11
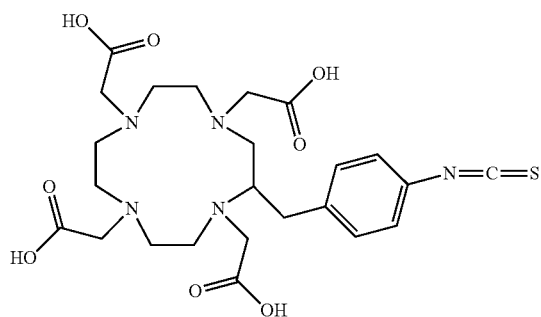 [SMILES: O=C(O)CN1CCN(CC(=O)O)CCN(CC(=O)O)C(Cc2ccc(N=C=S)cc2)CN(CC(=O)O)CC1]

E12 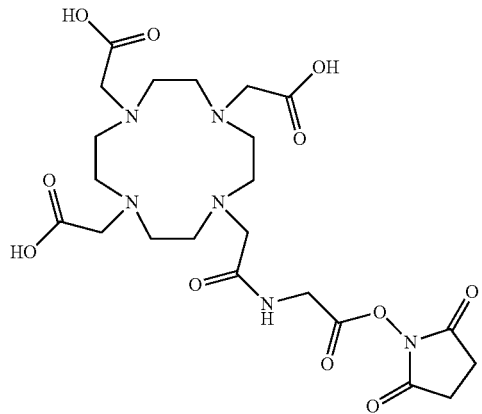 [SMILES: O=C(O)CN1CCN(CC(=O)O)CCN(CC(=O)NCC(=O)ON2C(=O)CCC2=O)CCN(CC(=O)O)CC1]
E13 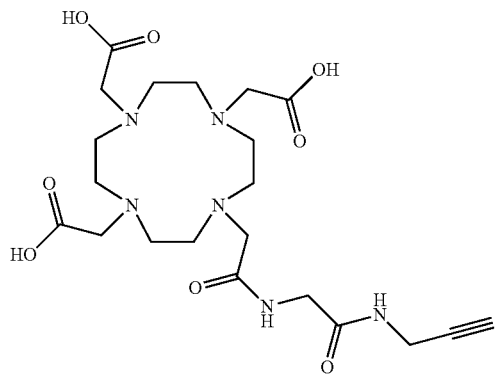 [SMILES: C#CCNC(=O)CNC(=O)CN1CCN(CC(=O)O)CCN(CC(=O)O)CCN(CC(=O)O)CC1]
E14 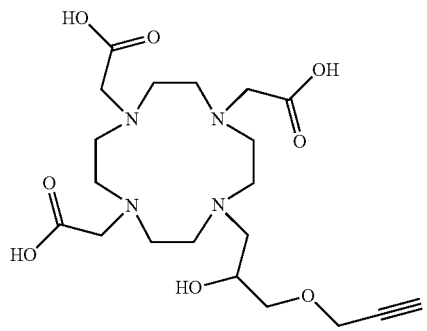 [SMILES: C#CCOCC(O)CN1CCN(CC(=O)O)CCN(CC(=O)O)CCN(CC(=O)O)CC1]
E15 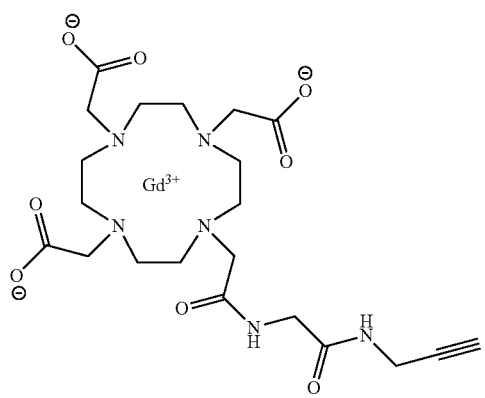

E16 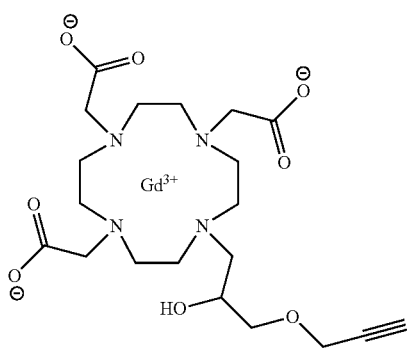
E17 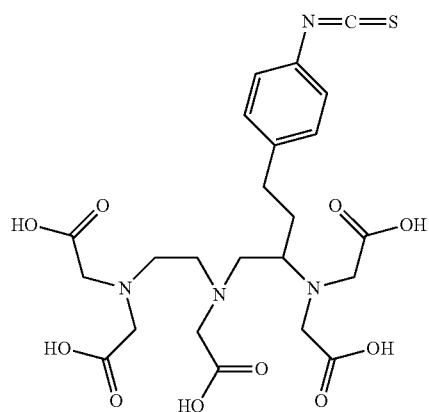 [SMILES: O=C(O)CN(CCN(CC(=O)O)CC(CCc1ccc(N=C=S)cc1)N(CC(=O)O)CC(=O)O)CC(=O)O]
E18 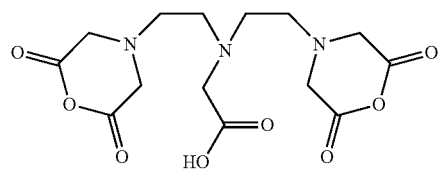 [SMILES: O=C(O)CN(CCN1CC(=O)OC(=O)C1)CCN1CC(=O)OC(=O)C1]
E19 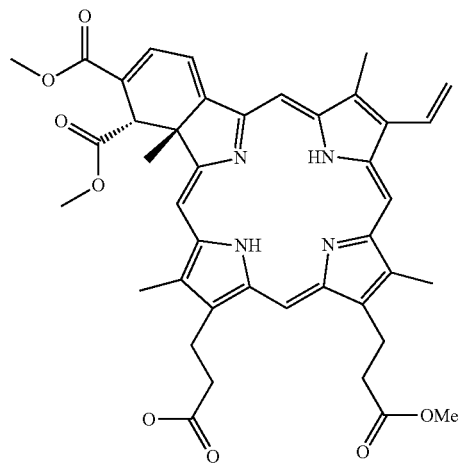 [SMILES: C=Cc1c(C)c2cc3nc(cc4[nH]c(cc5nc(cc1[nH]2)C(C)=C5CCC(=O)OC)c(CCC(=O)O)c4C)[C@@]1(C)C3=CC=C(C(=O)OC)[C@H]1C(=O)OC]

-continued
E20
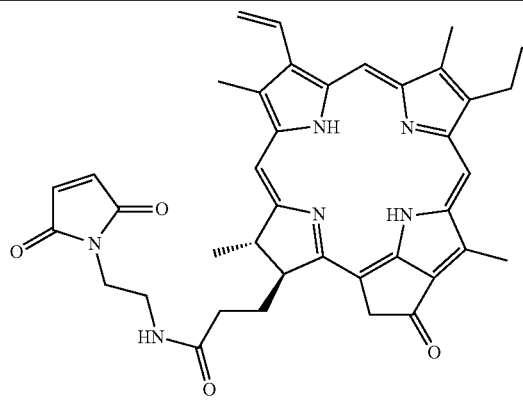
E21
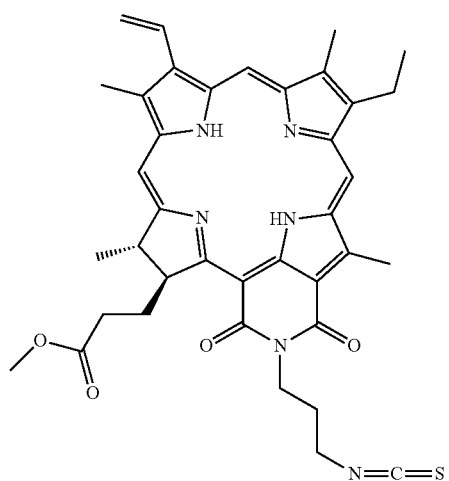 [SMILES: C=Cc1c(C)c2cc3nc(c4c5[nH]c(cc6nc(cc1[nH]2)C(C)=C6CC)c(C)c5C(=O)N(CCCN=C=S)C4=O)[C@@H](CCC(=O)OC)[C@@H]3C]
E22
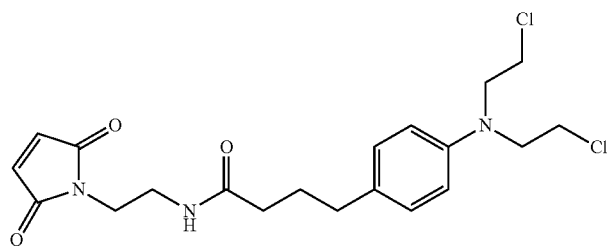 [SMILES: O=C(CCCc1ccc(N(CCCl)CCCl)cc1)NCCN1C(=O)C=CC1=O]
E23
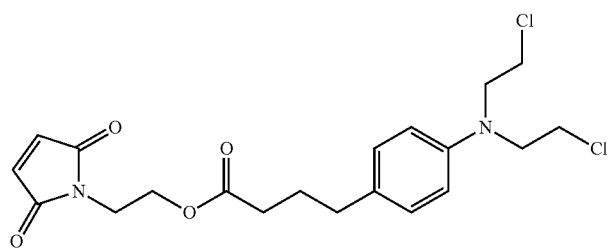 [SMILES: O=C(CCCc1ccc(N(CCCl)CCCl)cc1)OCCN1C(=O)C=CC1=O]
E24
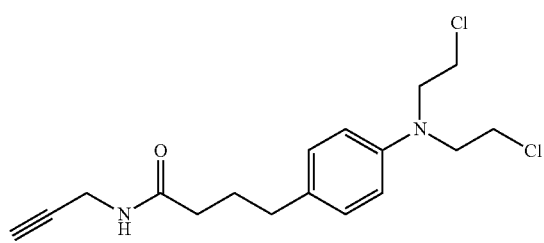 [SMILES: C#CCNC(=O)CCCc1ccc(N(CCCl)CCCl)cc1]

E25
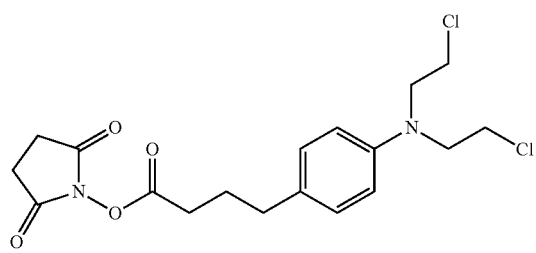 [SMILES: O=C(CCCc1ccc(N(CCCl)CCCl)cc1)ON1C(=O)CCC1=O]
E26
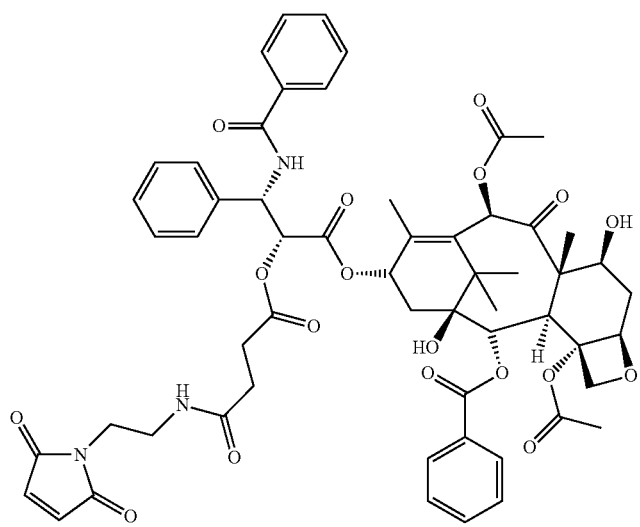
E27
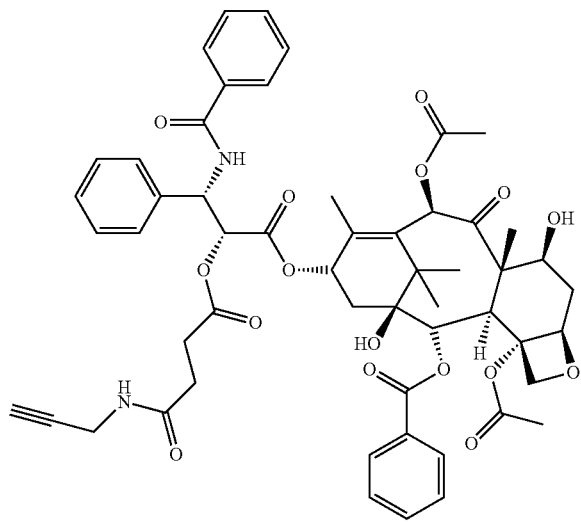

E28
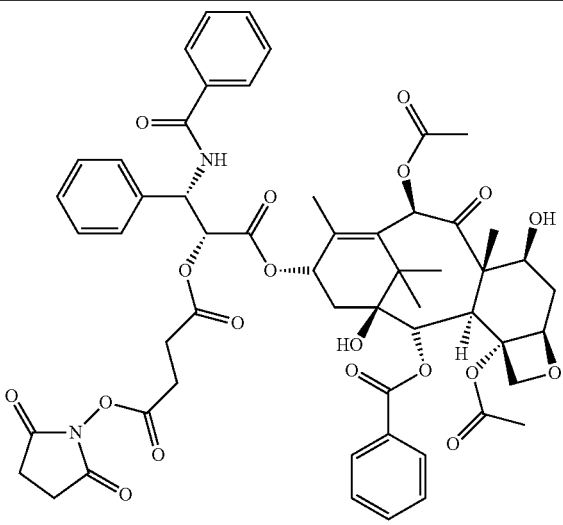

E29
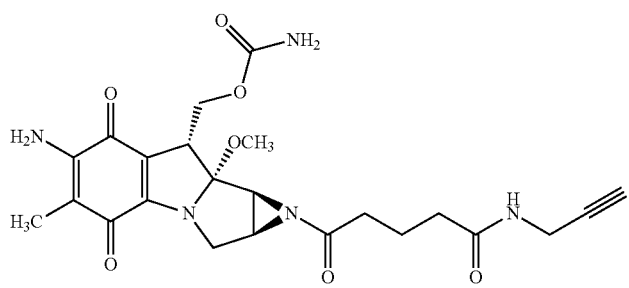 [SMILES: C#CCNC(=O)CCCC(=O)N1[C@H]2[C@@H]1CN1C3=C(C(=O)C(N)=C(C)C3=O)[C@H](COC(N)=O)[C@@]21OC]

E30
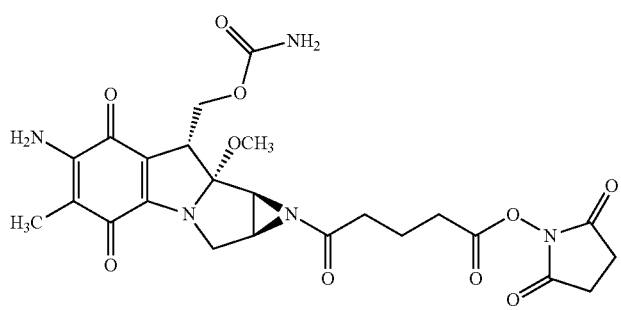 [SMILES: CO[C@]12[C@@H]3[C@H](CN1C1=C(C(=O)C(N)=C(C)C1=O)[C@@H]2COC(N)=O)N3C(=O)CCCC(=O)ON1C(=O)CCC1=O]

E31
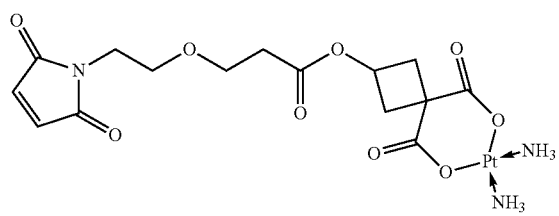

E32  siRNA with 3'-amino linker
E33  siRNA with 3'-pyridyldisulfide linker

The synthesis of the sulfated polyglycerols is known to persons skilled in the art as described above. The synthesis of linker derivatives comprises one or more additional synthetic steps. Generally, the linkers are covalently attached to the polyglycerol core by reaction with one or more OH groups of the polyglycerol. The reaction with the OH groups is accomplished in situ during the polymerization reaction by adding an appropriate electrophilic linker precursor to the reaction solution at an amount of 1-50 mol % of the glycidol momomers. The reaction with the OH groups is furthermore done using an isolated polyglycerol material, which is deprotonated with an appropriate base followed by the addition of an appropriate electrophilic linker precursor to the reaction solution at an amount of 1-50 mol % of the glycidol momomers. Examples for appropriate bases are sodium hydride, sodium methylate, sodium carbonate, potassium t-butylate. Sulfation is achieved preferably by using sulfurtrioxide complexes (pyridinium-SO$_3$, trimethylamine-SO$_3$, triethylamine-SO$_3$, dimethylformamide-SO$_3$). Sulfation is performed either on isolated polyglycerol or polyglycerol-linker derivatives, or subsequently after the polymerization in one step by adding the sulfation reagent directly into the polymerization reactor.

Appropriate electrophilic linker precursor materials are those of general formulas (VII)-(XI),

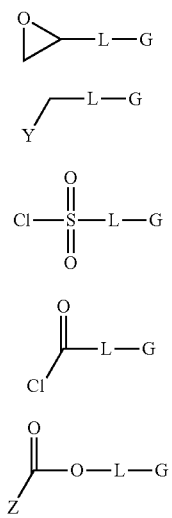

Formula VII
Formula VIII
Formula IX
Formula X
Formula XI wherein L is a branched or linear C$_{1-20}$-alkyl group in which one or more (preferably one to four) non-consecutive methylene groups may be replaced by a group selected from the group comprising O, S, NH, C(O)NH, C(NH$_2^+$)NH, SO$_2$, SO, aryl, ethene or ethyne, and wherein G is selected from the group comprising —OH, —OSO$_3$H, —OSO$_3$Na, —NH$_2$, —N$_3$, —COOH, —SH, —SO$_3^-$, —C≡C, with —OH, —NH$_2$, —SH. —COOH being optionally functionalized with protecting groups known to the skilled person, and wherein Y stands for a leaving group of an nucleophilic substitution reaction, such as Cl, Br, I, tosylate, mesylate, triflate or nosylate, and wherein Z stands for a leaving group selected from Cl, N-hydroxysuccinimidyl, imidazoyl, p-nitrophenyloxy.

Figure 4:
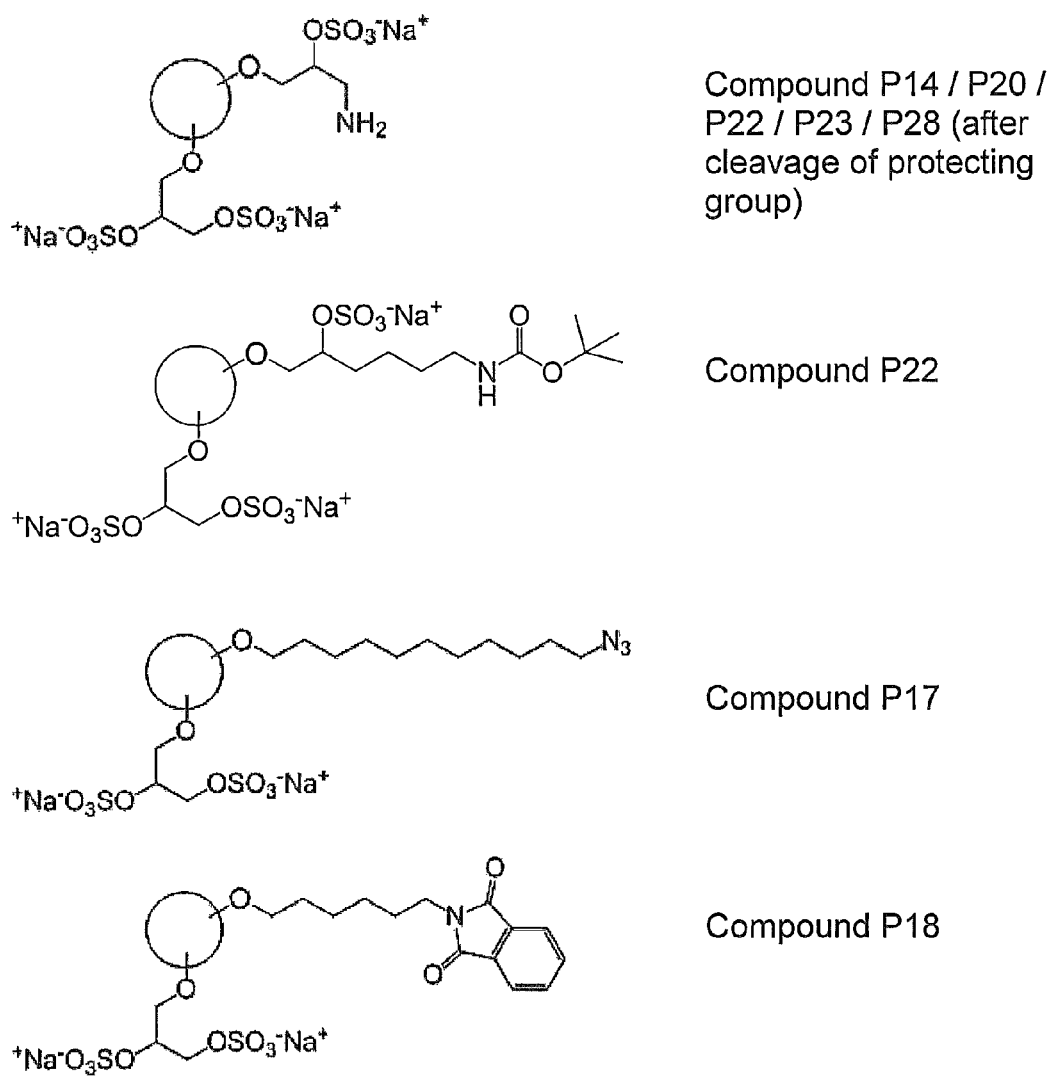
FIG. 4 depicts sulfated polyglycerols with linkers according to example 2. The examples include a schematic representation of the macromolecular sulfated polyglycerol backbone (bulb) with a representative structural subunit of sulfated glycerol, and a subunit to which the linker is attached.

Preferred electrophilic linker precursor materials are those of formula VII, wherein L is a linear C$_{1-20}$-alkyl group in which one or more (preferably one to four) non-consecutive methylene groups may be replaced by a group O giving —CH$_2$CH$_2$O— units and/or C(O)NH, C(NH$_2^+$)NH, C(O), and wherein G is selected from the group comprising —NH$_2$, —N$_3$, —COOH, —SH wherein these groups are optionally functionalized with protecting groups known to the skilled person. Exemplary structures according to the invention are depicted in FIG. 4. It is understood that the covalent attachment of a compound of formula VII represents the addition of a 3-carbon glycerol moiety wherein one hydroxyl group is replaced by the subunit L-G. This results in a polyglycerol where the linker adds an additional free hydroxyl group to the overall polymer backbone when reacting with a hydroxyl group by way of opening the epoxide reactive moiety. The resulting free hydroxyl group of the opened epoxide will be subject to sulfation accordingly (see FIG. 4, first entry).

Preferred reactive linker precursors are N-2,3-epoxypropylphthalimide, N-Boc-2,3-epoxypropylamine, N-Cbz-2,3-epoxypropylamine.

A particularly preferred linker is obtained by reacting an amino group with iminothiolane (Traut's reagent) yielding a linker unit of —NH—C(NH$_2^+$)—CH$_2$CH$_2$CH$_2$SH.

Chemical structures of linker precursor compounds are depicted in Table 2:

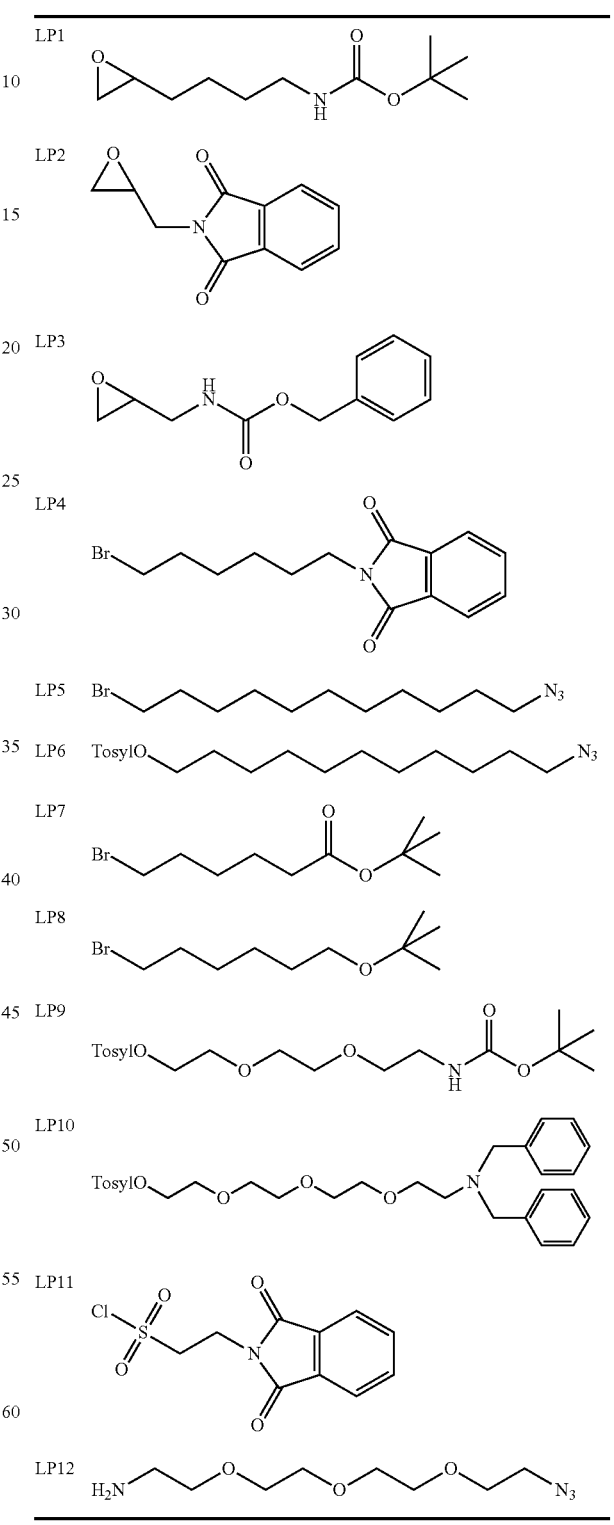

The compounds according to the present invention can be provided, for example, when used as medicaments, in form of pharmaceutical compositions, which comprise one or more of the compounds of the present invention as well as pharmaceutical acceptable carriers.

Preferably, these pharmaceutical compositions have a unit dosage form, such as tablets, pills, capsules, powder, granulate, sterile parenteral solutions or suspensions. Further dosage forms are known to the person of skill in the art. Another embodiment is a solid formulation of the compounds according to the invention together with known pharmaceutically acceptable carriers and/or excipients. The pharmaceutically acceptable carrier and/or excipient can have a wide variety of forms depending on the desired route of application (e.g. subcutaneous, intravenous, intraperitoneal). Suitable carrier and excipients are known in the art and can be selected by a person of skill in the art. Carrier include inert pharmaceutical excipients, like binding agents, suspension agents, lubricants, flavoring agents, sweetener, preservative agents, coloring agents and coating agents.

A particularly preferred embodiment is the pharmaceutical dosage form of a lyophilisate. It was surprisingly found that solutions of sulfated polyglycerol in aqueous media or buffers exhibit the tendency to form agglomerates or higher aggregates with increasing storage time. It was found that an immediate reconstitution of a solution from a lyophilized solid containing pharmaceutically acceptable additives does not lead to agglomerates or higher aggregates. The reconstitution can take place prior to administration. Preferred additives are cryoprotecting compounds (cryoprotectants or lyoprotectants), such as sucrose, mannose or trehalose, which can be used alone, as mixtures, or in combination with known other binding agents, suspension agents, buffering agents, lubricants, flavoring agents, sweetener, preservative agents, coloring agents and coating agents. Sucrose, mannose or trehalose are preferably used at an amount of 1-100 fold, more preferably 5-20 fold of the amount of sulfated polyglycerol and its conjugates according to the invention. Most preferred is the use of trehalose at a 5-20 fold amount, e.g. 10 mg drug with 100 mg trehalose.

Example 21 illustrates a time course of fluorescence of a conjugate of ICG derivative with sulfated polyglycerol (conjugate P17/E1) in aqueous solution. The decrease of fluorescence intensity indicates the ongoing degree of aggregation thus causing fluorescence quenching. It was surprisingly found that a freshly prepared solution from lyophilized drug substance using the additives described above, does not exhibit aggregation within the time scale studied (approx. 1 h). It is therefore an inventive step to propose lyophilized material of sulfated macromolecules, preferably sulfated polyglycerol, sulfated polyglycerol with linkers, and its conjugates with effector molecules according to the invention.

A medicament or a pharmaceutical composition comprises a therapeutically effective amount of the drug or of several drugs, i.e. a therapeutically effective amount of one or more compounds of the present invention. A skilled person will be able to determine the therapeutically effective amount on the basis of the disease to be treated and in consideration of the state of the patient. A medicament or a pharmaceutical composition can suitably contain between about 5 and 1000 mg, preferably about 10 to 500 mg of a compound according to the present invention.

The route of administration of the compounds according to the invention is preferably parenteral, including subcutaneous, intravenous, intraperitoneal, intraocular, intramuscular, intratumoral. Most preferred is the intravenous and subcutaneous route of administration. It was surprisingly found, that a repeated daily dosing (subcutaneous) up to 30 days in different animal disease models (example 13, 14, 15) did not lead to observations of toxicity and did not cause adverse events over the entire time range of treatment. Thus, the invention comprises the use of sulfated polyglycerol and conjugates of sulfated polyglycerol with effector molecules for treating a disease selected from the group comprising cancer, inflammation, autoimmune disease and fibrosis with multiple dosages of compounds. Multiple dosages means treatments using more than one dosage, including daily treatment, treatment every 2 up to 7 days, treatment more than once daily, or time intervals such as treatment in intervals of five days. More specifically, the invention comprises the multiple treatment of patients with a subcutaneous dose of 10 mg/kg up to 1000 mg/kg, preferably 20 mg/kg to 500 mg/kg, most preferably 50 mg/kg to 200 mg/kg body weight. The invention comprises further the multiple treatment of patients with an intravenous dose of 1 mg/kg up to 200 mg/kg, preferably 10 mg/kg to 100 mg/kg, most preferably 20 mg/kg to 50 mg/kg body weight.

EXAMPLES

Example 1

Generation of Polyanionic Multivalent Macromolecules for Intracellular Targeting of Proliferation and Protein Synthesis by the Synthesis of Sulfated Polyglycerols Example 1a Generation of dendritic polyglycerol cores by anionic polymerization of glycidol: Dendritic polyglycerols are obtained and characterized according to Bioconjugate Chemistry 15, 2004, 162-167; Advanced Materials 12, 2000, 235-239; Macromolecules 32, 1999, 4240. A variety of polymeric materials of different average molecular weights are obtained from different starter molecules (1,1,1-tris(hydroxymethyl) propane (TMP), 1,1,1-tris(hydroxymethyl)ethane (TME) and penterythrol (PE)) and applied to sulfation reactions.

Example 1b

Synthesis of highly sulfated polyglycerols: sulfated polyglycerols are synthesized based on the experimental description in Bioconjugate Chemistry 15, 2004, 162-167. To achieve high degrees of sulfation, the published procedure is modified. $SO_3$/pyridine complex is added in 1.2-fold molar excess at 90° C., and stirring at 90° C. is continued for 18 h. Purification is achieved by dialysis and ultrafiltration (MW cut-off 2000). Degree of sulfation is determined by elementary analysis. All compounds are obtained as sodium salts (Table 3).

A desired degree of sulfation cannot be adjusted by the use of a defined molar ratio of the sulfation reagent in the reaction mixture, since its reactivity depends on the nature, purity and origin of the reagents and starting materials used. However, with excess of sulfation reagent a degree of sulfation above 90% is ensured, while less sulfation reagent, preferably 0.6 to 1 molar equivalents, allow to receive products in the area of 50 to 90% sulfation.

TABLE 3

Sulfated polyglycerol obtained in example 1b:

| Comp. # | Starter molecule | Mean molecular weight (Mn) of PG core (g/mol) | Degree of sulfation (%) | Mean molecular weight (Mn) of polyglycerol sulfate (g/mol) |
|---|---|---|---|---|
| P1  | PE  | 2,600  | 88   | 5,750  |
| P2  | PE  | 2,600  | 91   | 5,860  |
| P3  | PE  | 6,000  | 92   | 13,600 |
| P4  | PE  | 7,000  | 92   | 15,880 |
| P5  | PE  | 7,500  | 82.5 | 16,030 |
| P6  | PE  | 7,500  | 86   | 16,390 |
| P7  | PE  | 7,500  | 92   | 16,920 |
| P8  | PE  | 10,500 | 92   | 23,820 |
| P9  | TMP | 3,000  | 88   | 6,640  |
| P10 | TMP | 6,000  | 85   | 13,030 |
| P11 | TMP | 6,000  | 91   | 13,530 |
| P12 | TMP | 7,500  | 89   | 16,700 |
| P13 | TMP | 7,500  | 94   | 17,220 |

Example 1c

General procedure for the synthesis of sulfated polyglycerols as "one step" procedure. The reaction is conducted in a reactor equipped with mechanical stirrer. The whole apparatus is dried under vacuum and flushed with dried argon. The drying procedure is repeated 4 times. Glycidol applied from Acros (purity >96%) is stirred over $CaH_2$ over night and distilled at 45° C. and 1 mbar. Fraction 1 (5% of the glycidol amount used) consists of di-/trimers. Fraction 2 is the desired pure glycidol. The distilled glycidol is kept in the fridge and only opened under dry conditions. TMP (2.68 g, 20 mmol) is added to the reactor and melted at 60° C. in vacuo. Under argon atmosphere, KOtBu (1 M in THF, 6 mL) is added and the precipitate is dissolved by addition of NMP. The mixture is heated to 120° C. and stirred for 2 h to remove the t-butyl alcohol. Glycidol (100 g, 1.35 mol) is dissolved in 225 mL dry THF (ratio 1:2.5) and added with a dosing pump over 18 h. The mixture is cooled down to 90° C. and diluted with 200 mL dry DMF. Pyridine-$SO_3$ complex (215 g, 1.35 mol) is added as solid and further 50 mL dry DMF is added. After stirring for 24 h, 350 mL water is added to the reaction mixture in a separate flask, and the mixture is neutralized with 2M NaOH to a pH of approximately 9-10. After evaporation to dryness, the crystalline solid is stirred over diethyl ether to remove NMP. Purification is achieved by ultrafiltration (water, reg. cellulose membrane; MWCO 1000). After evaporation and drying in high vacuum, the product is obtained as pale yellow amorphous solid.

Example 2

Generation of Polyanionic Macromolecular Carrier Molecules for Intracellular Targeting of Proliferation and Protein Synthesis by the Synthesis of Sulfated Polyglycerols with Linkers for Covalent Conjugation of Effector Molecules

Example 2a

General procedure for the synthesis of dendritic polyglycerol cores with additional functionalized linker units attached in the course of the polymerization reaction: A modified polymerization synthesis is performed based on the published synthesis in Bioconjugate Chemistry 15, 2004, 162-167. After finished addition of the monomeric reaction partner glycidol, the polymerization reaction is continued by the addition of the reactive linker species which is attached to the deprotonated hydroxyl groups at a temperature 60-100° C. Linker was added at 1-50 mol % relative to glycidol and reaction is continued for 2-24 h. The crude polymer is obtained by repeated precipitation from methanol/acetone and dried in high vacuum at 50-80° C. for 24 h. This material is used in the sulfation reaction.

Example 2b

General procedure for the attachment of a linker via ether bond via a second synthetic step using an isolated polyglycerol material leading to example compounds P14 to P25: Dendritic polyglycerols obtained in example 1a are purified by dialysis (water, MWCO 3000), evaporated in vacuum and dried in high vacuum (0.05 mbar) for 24 h at 60° C. 1 g polyglycerol is dissolved in dry DMF (20 mL) at 60° C. and treated with sodium hydride (2.5 molar equivalents per OH to be derivatized with linker), followed by stirring at 80° C. for 18 h. Then, a solution of an equal molar amount of linker containing bromide or tosylate leaving groups or epoxide reactive groups (table 2) in DMF is added at 80° C. and the solution is stirred for another 18 h. The product is quenched by addition of methanol, precipitated with acetone, dried in vacuum and dialysed in methanol (MWCO 1000) for 2 days, followed by drying in high vacuum at 60° C.

Example 2c

General procedure for the attachment of a linker via carbamate bond via a second synthetic step using an isolated polyglycerol material leading to example compounds P26 and P27: Dendritic polyglycerols are obtained in example 1a were purified by dialysis (water, MWCO 3000), evaporated in vacuum and dried in high vacuum (0.05 mbar) for 24 h at 60° C. 1 g polyglycerol is dissolved in dry DMF (20 mL). To this solution is added carbonyldiimidazol (CDI; 5 molar equivalents per OH to be derivatized with linker) and the solution is stirred for 24 h. Then, acetone is added to precipitate the activated polyglycerol. The residue is dissolved in 15 mL of DMF and a solution of LP12 (1.5 equivalents per OH; 12 eq. overall; see table 2) in DMF is added and the mixture stirred at room temp. for another 18 h. The product is precipitated with acetone, dried in vacuum and dialysed in methanol (MWCO 2000) for 2 days, followed by drying in high vacuum at 60° C.

Example 2d

Synthesis of sulfated polyglycerols with linkers by sulfation of compounds of example 2a-c: The reaction is conducted according to Bioconjugate Chemistry 15, 2004, 162-167 and example 1b. Purification is achieved by dialysis and ultrafiltration. Degree of sulfation is determined by elementary analysis. All compounds are obtained as sodium salts (Table 4).

TABLE 4

Polyglycerol sulfates P14-P27 with linkers obtained in example 2a-d (before cleavage of protecting groups), and P28 obtained in example 2e:

| Comp. # | Starter molecule | Mean molecular weight (Mn) of PG core (g/mol) | Degree of sulfation (%) | Linker molecule # | Degree of linker substitution (%) | Mean molecular weight (Mn) of polyglycerol sulfate with linker (g/mol) |
|---|---|---|---|---|---|---|
| P14 | PE  | 7,500  | 74 | LP2  | 3  | 15,770 |
| P15 | PE  | 7,500  | 91 | LP4  | 3  | 17,600 |
| P16 | PE  | 10,500 | 86 | LP9  | 7  | 25,250 |
| P17 | PE  | 6,000  | 92 | LP6  | 3  | 13,800 |
| P18 | TMP | 7,000  | 86 | LP4  | 5  | 16,380 |
| P19 | TMP | 10,000 | 72 | LP4  | 20 | 26,110 |
| P20 | TMP | 5,500  | 83 | LP3  | 10 | 12,780 |
| P21 | TMP | 7,500  | 78 | LP3  | 12 | 17,180 |
| P22 | TME | 3,000  | 92 | LP1  | 5  | 7,220 |
| P23 | TME | 3,000  | 75 | LP2  | 15 | 7,340 |
| P24 | TME | 2,500  | 85 | LP3  | 5  | 5,840 |
| P25 | TME | 2,500  | 80 | LP3  | 10 | 6,080 |
| P26 | PE  | 6,000  | 80 | LP12 | 8  | 14,200 |
| P27 | PE  | 6,000  | 75 | LP12 | 15 | 15,160 |
| P28 | TMP | 5,500  | 88 | LP2  | 5  | 13,000 |

The following procedures to remove protecting groups can be applied, but are not limited to. Boc-protected amino groups, ᵗbutylester, ᵗbutyl-protected hydroxyl group, THP-protected hydroxyl group: 100 mg of polymer is dissolved in 5 mL of trifluoroacetic acid/water (1:2) and stirred for 2 h at room temperature. The solvent is removed in vacuum, the residue is repeatedly treated with dichloromethane and evaporated. Then 5 mL of water are added. The pH of the solution is adjusted to 8 by the addition of 1M NaOH solution. Purification of the final product is achieved by ultrafiltration in destilled water.

Phthalimido-protected amino groups: 100 mg of polymer are dissolved in 5 mL of methanol/water (1:1) and to this solution is added hydrazine monohydrate (1 mL). The solution is stirred for 4 h at room temperature. The solvent is removed in vacuum, the residue is repeatedly treated with dichloromethane and evaporated. Then 5 mL of water is added. The pH of the solution is adjusted to 8 by the addition of 1M NaOH solution. Purification of the final product is achieved by ultrafiltration in water.

A second method to deprotect the phthalimido group using sodium borohydride and acetic acid is described in example 2e.

Carbobenzyloxy (Cbz)-protected amino groups, benzyl and dibenzyl-protected amino groups, Benzyl esters: 100 mg of polymer is dissolved in 10 mL of methanol/water (9:1) and to this solution is 10 mg 10% Pd/C catalyst. The solution is stirred for 24 h under hydrogen at 3 mbar. The mixture is filtrated via celite, the solvent is removed in vacuum, the residue is repeatedly treated with dichloromethane and evaporated. Then 5 mL of water are added. The pH of the solution is adjusted to 8 by the addition of 1M NaOH solution. Purification of the final product is achieved by ultrafiltration in aqua dest.

Reduction of azido groups to amino groups: 100 mg of polymer are dissolved in 20 mL of THF/water (1:1) and to this solution is added 5 mol-eq. triphenylphosphine per azido group. The solution is stirred for 48 h under argon at room temperature. The solvent is removed in vacuum, the residue is resuspended in water and the precipitate filtered off and discarded. The aqueous solution is then subjected to ultrafiltration in aqua dest.

Example 2e

Procedure for the synthesis of sulfated polyglycerols with linker as "one step" procedure using linker precursor derivative N-(2,3-epoxypropyl)phthalimide (LP2): The reaction is conducted in a reactor equipped with mechanical stirrer. The whole apparatus is dried under vacuum and flushed with dried argon. The drying procedure is repeated 4 times. Glycidol applied from Acros (purity >96%) is stirred over $CaH_2$ over night and distilled at 45° C. and 1 mbar. Fraction 1 (5% of the glycidol amount used) consists of di-/trimers. Fraction 2 is the desired pure glycidol. The distilled glycidol is kept in the fridge and only opened under dry conditions. TMP (2.68 g, 20 mmol) is added to the reactor and melted at 60° C. in vacuo. Under argon atmosphere, KOtBu (1 M in THF, 6 mL) is added and the precipitate is dissolved by addition of NMP. The mixture is heated to 120° C. and stirred for 2 h to remove the t-butyl alcohol. Glycidol (100 g, 1.35 mol) is dissolved in 225 mL dry THF (ratio 1:2.5) and added with a dosing pump over 18 h. N-(2,3-epoxypropyl)phthalimide (27.4 g, 135 mmol) is dissolved in 55 mL dry THF by heating, added with a syringe over 70 minutes and stirred over night. The mixture is cooled down to 90° C. and diluted with 200 mL dry DMF. Pyridine-$SO_3$ complex (215 g, 1.35 mol) is added as solid and further 50 mL dry DMF is added. After stirring for 24 h, 350 mL water is added to the reaction mixture in a separate flask, and the mixture is neutralized with 2M NaOH to a pH of approximately 9-10. After evaporation to dryness, the crystalline solid is stirred over diethyl ether to remove NMP. Purification is achieved by ultrafiltration (water, reg. cellulose membrane; MWCO 1000). After evaporation and drying in high vacuum, the product is obtained as pale yellow amorphous solid.

For example compound P28 GPC analysis (eluent: water, standards: pullulan) of a probe removed before addition of pyridine-$SO_3$ complex gives a $M_n$ of 5,500 g/mol and a polydispersity index of 1.4. MALDI-TOF allows to determine specimens of 4-5 phthalimido linkers in average. Sulfation yields a degree of 88%. Deprotection is achieved by treating 10 g (approx. 13,000 g/mol) of sulfated intermediate with sodium borohydride (1.5 g) in 25 mL water for 5 h at room temp. To this mixture is added acetic acid (5 mL) followed by stirring at 80° C. for 3 h. Purification is achieved by ultrafiltration (sat. NaCl, then dest. water, reg. cellulose membrane; MWCO 2000) yielding 8 g of sulfated aminopolyglycerol as white amorphous solid.

Example 3

Synthesis of Conjugates of Sulfated Polyglycerol with Diagnostic Effector Molecules (E) Out of the Class of Cyanine Dyes

Example 3a

Generation of cyanine dye conjugate by reaction of an isothiocyanate cyanine dye (E3) with amino-modified sulfated polyglycerol P14: 200 mg of P14 is deprotected with hydrazine according to example 2d yielding 160 mg material after dialysis. These 160 mg of polymer P14 are dissolved in 1 mL sodium acetate buffer (100 mM) and treated with isothiocyanate cyanine dye E3 (3 eq.) for 24 h at 40° C. The product is purified by separating unreacted dye by ultrafiltration (reg. cellulose, MWCO 3000) in water, followed by lyophilization. Product: 140 mg of a green amorphous solid (see FIG. 5).

Example 3b

Generation of cyanine dye conjugate by reaction of a propargyl cyanine dye (E2) with azido-modified sulfated polyglycerol P26: Polymer P26 (30 mg) and dye E2 (5.5 mg) are dissolved in a mixture of 0.6 mL phosphate-buffered saline (PBS; pH7.4) and 0.2 mL methanol. To this mixture is added 0.1 mL of a solution of $CuSO_4$.pentahydrate (12 mg/mL in PBS) and 0.1 mL sodium ascorbate (3.8 mg/mL in PBS). The solution is incubated under vigorous shaking at 40° C. for 5 days under light protection. Purification is achieved by ultrafiltration (reg. cellulose, MWCO 4000-6000) in dest. water, followed by size-exclusion chromatography (Sephadex G-50). Lyophilization afforded a green solid (19 mg). (see FIG. 5).

Example 3c

Generation of cyanine dye conjugate by reaction of a propargyl cyanine dye E5 (Sisson et al., Angew. Chem. Int. Ed. 48: 7540-7545, 2009) with azido-modified sulfated polyglycerol P17: Polymer P17 (30 mg) and dye E5 (5 mg) are dissolved in a mixture of 0.4 mL phosphate-buffered saline (PBS; pH7.4) and 0.4 mL ethanol. To this mixture is added 0.1 mL of a solution of $CuSO_4$.pentahydrate (12 mg/mL in PBS) and 0.1 mL sodium ascorbate (3.8 mg/mL in PBS). The solution is incubated under vigorous shaking at 40° C. for 5 days under light protection. Purification was achieved by a combination of ultrafiltration (reg. cellulose, MWCO 4000-6000) in methanol and prep. HPLC (RP18, water) giving the product as immediately eluting peak. Lyophilization afforded 18 mg of indocarbocyanine (ICC) conjugate (purple red lyophilisate). (see FIG. 5).

The reaction procedure of example 3b and 3c can be further applied to the preparation of the conjugates based on polymer/dye combinations such as P17/E1, P17/E2, P26/E1, P26/E5, P27/E1, P27/E2, P27/E5.

Example 3d

Generation of cyanine dye conjugate by reaction of a cyanine dye-NHS-ester E7 with amino-modified sulfated polyglycerol P28: 200 mg of P28 are dissolved in a mixture of DMF/water of 9:1 (2 mL). To this mixture is added 86 mg of NHS-ester dye E7 (4 mol-eq.) followed by 48 h of stirring at room temp. After evaporation to dryness, purification of the solid residue was achieved as described in example 3c. Lyophilization afforded 185 mg of indodicarbocyanine conjugate (blue lyophilisate).

The reaction procedure of example 3d can be further applied to the preparation of the conjugates of P28 with dye E8 and other NHS esters of diagnostic and therapeutic effector molecules (see also Example 4b).

Example 3e

Synthesis of cyanine dyes used in examples 3a-d: Propargyl cyanine dye (E1) is synthesized with modification of Lee et al., J. Org. Chem. 73: 723 (2008) describing the derivatization of IR-820 by Suzuki reaction using phenylboronic acid precursors. In the present invention, IR-820 was reacted with 4-carboxyethylphenylboronic acid giving the respective Suzuki-coupled product. Conversion to E1 was achieved with propargylamine and HBTU using a known procedure of amide formation. In accordance to this procedure, the novel analogs of IR-820 with a higher substitution of the aromatic rings with sulfonate groups are obtained, followed by Suzuki coupling and amidation with propargyl amine (see E2-E4 in table 1). For this purpose, 1-(4-sulfonatobutyl)-2,3,3-trimethylbenzindoleninium-5,7-disulfonate, disodium salt and 1-(4-sulfonatobutyl)-2,3,3-trimethylbenzindoleninium-6-sulfonate, sodium salt was prepared according to methods published, followed by conversion into IR-820 analogs using N-[(3-(anilinomethylene)-2-chloro-1-cyclohexene-1-yl)methylene]aniline monohydrochlorid (Salon et al., J. Heterocycl. Chem. 42: 959 (2005)).

Example 3f

Synthesis of conjugate of cyanine dye E1 with sulfated glycerol dendron: The synthesis yields a dye conjugate with a defined dendron comprising 16 sulfate groups. E1 was reacted with [G3.0]-azide (compound 14 in Wyszogrodzka et al., Chemistry 14: 9292 (2008)) as described in example 3b. Deprotection of acetals is achieved as described by Wyszogrodzka et al., followed by sulfation according to example 2d. HPLC analysis yields the conjugate in 25% yield.

Example 4

Synthesis of Conjugates of Sulfated Polyglycerol with Diagnostic Effector Molecules (E) Out of the Class of Chelates/Complexing Agents for Radiolabeling

Example 4a

Figure 6:
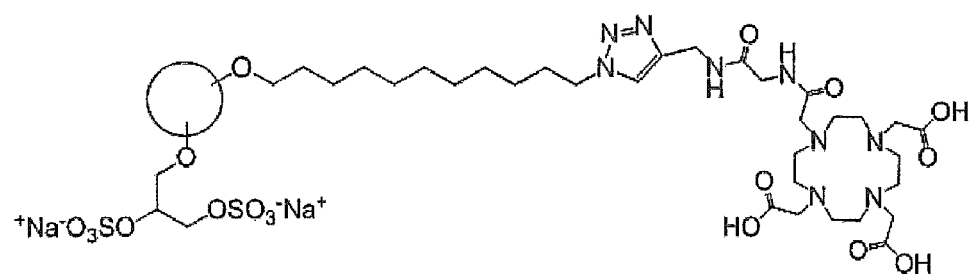
FIG. 6 depicts sulfated polyglycerol conjugates with diagnostic effector molecules out of the class of chelators for radiolabeling (radiodiagnostics and radiotherapy) according to example 4 and metal complexes for MRI according to example 5. The examples include a schematic representation of the macromolecular sulfated polyglycerol backbone (bulb) with a representative structural subunit of sulfated glycerol, and a subunit to which the linker and effector molecule is attached.
Figure 6:
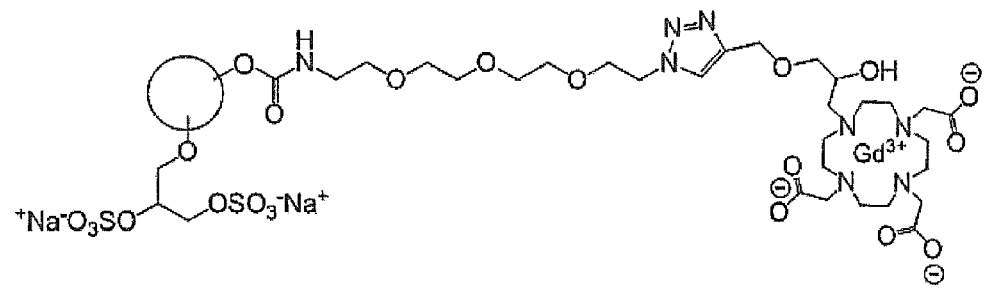

Generation of polyglycerol chelator conjugate by reaction of propargyl-DOTA (E13) with azido-modified sulfated polyglycerol P17: Polymer P17 (30 mg) and propargyl-DOTA E13 (3 mg) are dissolved in a mixture of 0.4 mL phosphate-buffered saline (PBS; pH7.4) and 0.4 mL ethanol. To this mixture is added 0.1 mL of a solution of $CuSO_4$.pentahydrate (12 mg/mL in PBS) and 0.1 mL sodium ascorbate (3.8 mg/mL in PBS). The solution is incubated under vigorous shaking at 40° C. for 5 days under light protection. Purification is achieved by a ultrafiltration (reg. cellulose, MWCO 4000-6000) in water yielding 20 mg of conjugate as white solid (FIG. 6).

Example 4b

Generation of polyglycerol chelator conjugate by reaction of propargyl-DO3A (E14) with azido-modified polyglycerolsulfate P17: The reaction is performed as described for example 4a.

Furthermore, DOTA chelator conjugates can be obtained by reaction of amino-modified sulfated polyglycerol with DOTA-NHS ester according to the procedure in example 3d, such as using P28 and E12.

Example 5

Synthesis of Conjugates of Sulfated Polyglycerol with Diagnostic Effector Molecules (E) Out of the Class of $Gd^{3+-}$ Complexes for Magnetic Resonance Imaging (MRI)

Example 5a

Generation of polyglycerol conjugate with gadolinium complex by reaction of propargyl-$Gd^{3+-}$DO3A derivative (E16) with azido-modified polyglycerol sulfate P27. The high number of azido groups (15%) is required to yield a high effector/polymer ratio. Polymer P27 (50 mg) and complex E16 (36 mg) are dissolved in a mixture of 0.8 mL phosphate-buffered saline (PBS; pH8.5) and 0.4 mL methanol. To this mixture is added 0.2 mL of a solution of $CuSO_4$.pentahydrate (12 mg/mL in PBS) and 0.2 mL sodium ascorbate (3.8 mg/mL in PBS). The solution is hold under vigorous shaking at 25° C. for 3 days. Purification is achieved by a ultrafiltration (reg. cellulose, MWCO 4000-6000) in water yielding 52 mg of conjugate as white solid. Metal analysis by ICP-MS yields a gadolinium content of 5 moles gadolinium complex per mole polymer (FIG. 6).

Example 6

Figure 7:
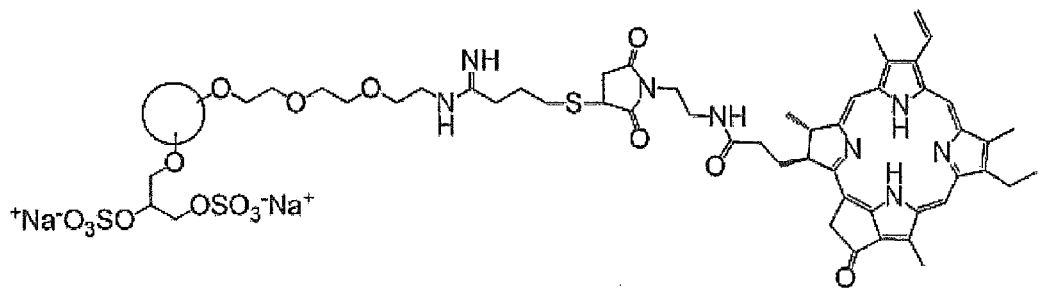
FIG. 7 depicts sulfated polyglycerol conjugates with therapeutic effector molecules out of the class of photosensitizers, cytostatics (chloroambucil and paclitaxel) and siRNA according to example 6. The examples include a schematic representation of the macromolecular sulfated polyglycerol backbone (bulb) with a representative structural subunit of sulfated glycerol, and a subunit to which the linker and effector molecule is attached.
Figure 7:
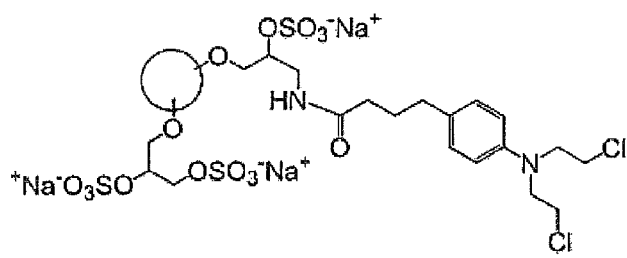
Figure 7:
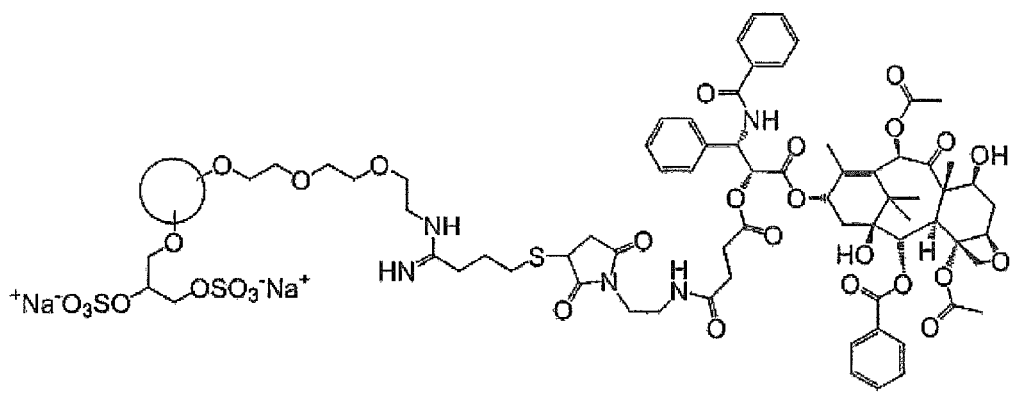
Figure 7:
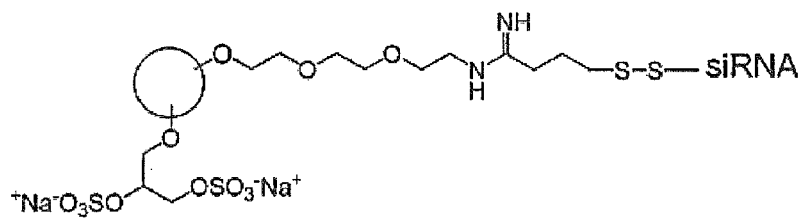

Synthesis of Conjugates of Sulfated Polyglycerol with Therapeutic Effector Molecules (E) Out of the Class of Photosensitizers, Cytostatics or siRNA Example 6a Generation of photosensitizer conjugate by reaction of a maleimido photosensitizer (E20) with thiol-modified sulfated polyglycerol: Thiol-modification of sulfated polyglycerol is achieved by using polymer P16. 50 mg of polymer P16 are stirred in 1 mL water/trifluoroacetic acid for 2 h and then precipitated with ethanol, followed by drying in high vacuum. This material is dissolved in 0.5 mL of 10 mM phosphate buffer (pH 7.0) and treated with 10 mol-eq. of 2-iminothiolane for 1 h at room temp. To this mixture is added 0.67 mL (10 mol-eq.) of a solution of maleimido-pyropheophorbide (E16) in DMF (conc. 20 mg/mL), The reaction mixture is shaken vigorously at 45° C. for 24 h. Product is isolated by evaporating the mixture, and washing/centrifuging the residue several times with dichloromethane. Final purification is achieved by prep. HPLC (RP18, water/methanol) yielding 20 mg of conjugate (FIG. 7).

Example 6b

Generation of chloroambucil conjugate by reaction of a chloroambucil-N-hydroxysuccinimidylester (E25) with amino-modified sulfated polyglycerol: 200 mg of P14 is deprotected with sodium borohydride/acetic acid according to example 2e yielding 160 mg material after dialysis. These 160 mg of polymer P14 were dissolved in 1 mL of a mixture (9:1) of DMF and 50 mM phosphate buffer (pH8.0) To this mixture is added E25 (15 eq.) followed by vigorous stiffing for 24 h at 40° C. Product is isolated by evaporating the mixture, and washing/centrifuging the residue several times with dichloromethane. Aromatic signals in the $^1$H-NMR reveal conjugation of approx. 1.8 chloroambucil molecules per polymer in average (FIG. 7).

Similarly, reaction with paclitaxel succinate NHS ester (E28) gives 1.2 paclitaxel molecules per polymer in average.

Example 6c

Generation of paclitaxel conjugate by reaction of a maleimido paclitaxel (E26) with thiol-modified sulfated polyglycerol: Thiol-modification of polyglycerolsulfate using 2-iminothiolane is achieved as described in example 6a. To a solution of thiol-modified sulfated polyglycerol (50 mg/mL) is added 10 mol-eq. of maleimido paclitaxel (E20; solution of 10 mg/mL in DMF), The reaction mixture is shaken vigorously at 25° C. for 24 h. Product is isolated by evaporating the mixture, and washing/centrifuging the residue several times with dichloromethane. Aromatic signals in the $^1$H-NMR reveal conjugation of approx. 2 paclitaxel molecules per polymer in average (FIG. 7).

Similarly, reaction with chloroambucil maleimides (E22 or E23) gives 2.2 chloroambucil molecules per polymer in average.

Furthermore, paclitaxel conjugates can be obtained by reaction of amino-modified sulfated polyglycerol with paclitaxel-NHS ester according to the procedure in example 3d by using P28 and E28, giving conjugates of 1 paclitaxel molecule per polymer in average.

Example 6d

Generation of conjugate with diamine platinum(II) complex (carboplatin analog) by reaction of maleimido linker derivative (E31) and thiol-modified sulfated polyglycerol: Thiol-modification of polyglycerolsulfate using 2-iminothiolane is achieved as described in example 6a. Carboplatin maleimide (E31) is synthesized according to Warnecke et al. Bioconjugate Chem. 2004, 15(6), 1348-1359. To a solution thiol-modified sulfated polyglycerol (50 mg/mL) are added 15 mol-eq. of E31 (solution of 20 mg/mL in ethanol), the reaction mixture is shaken vigorously at 25° C. for 24 h. Product is isolated by evaporating the mixture, and washing/centrifuging the residue several times with dichloromethane and n-butanol. Platinum content is determined by ICP-MS (metal-to-polymer ratio 2:1).

Example 6e

Synthesis of conjugates of sulfated polyglycerol with siRNA.

VEGF siRNA was obtained according to J. Contr. Release 2006, 116, 123-129.

```
sense strand:
                                        (SEQ ID NO: 1-dTdT)
5'-GGAGUACCCUGAUGAGAUCdTdT-3' antisense strand:
                              (SEQ ID NO: 2-dTdT-hexylaminom)
5'-GAUCUCAUCAGGGUACUCCdTdT-3'-hexylaminom (E32).
```

Activation is achieved using SPDP giving a 2-pyridyldisulfide group (J. Contr. Release 2006, 116, 123-129) yielding effector E33 for reaction with thiol-modified sulfated polyglycerol, allowing covalent conjugation by sulfhydryl exchange reaction. Thiol-modification of amino-modified, sulfated polyglycerol is achieved by using polymer P16 according to example 6a. 10 mg of polymer P16 were stirred in 100 μL water/trifluoroacetic acid for 2 h and then precipitated with ethanol, followed by drying in high vacuum. This material is dissolved in 200 μL of 10 mM HEPES buffer (pH 8.0) and treated with 5 mol-eq. of 2-iminothiolane for 1 h at room temp. To this solution is added VEGF siRNA (1.2 mol-eq.) and the mixture is incubated at room temp. for 2 h at 40° C. This mixture is passed through a NAP10 column using HEPES buffer (pH8.0) and then used directly in cell culture experiments (FIG. 7).

Example 7

Incubation of Human Lung Tumor A549 Cells with Fluorescent Polyglycerols of Different Molecular Weights and In Vitro Fluorescence Imaging The epithelial human lung cancer cell line was routinely propagated as follows: DEMEM medium, with 10% fetal calf serum, 2% glutamine, and penicillin/streptomycin (all from PAN Biotech) added. Cells were seeded into medium at $1\times10^5$ cells/ml, cultured at 37° C. with 5% $CO_2$, and split 1:5 two times a week. For in vitro fluorescence imaging cell were seeded at $2\times10^5$ cells/ml in 24-well culture plates on glass coverslips (Sigma), and cultured for 24 hours at 37° C. Thereafter, cells were cultured with medium containing $10^{-6}$M polyglycerols with different molecular weights conjugated with indocarbocyanine (ICC) propargyl ester (compound E5) or $10^{-6}$ M ICC-triglycerol conjugate (Angew Chem Int Ed Engl. 48: 7540, 2009) as control for 1 hour at 37° C. Afterwards, cells were fixed with cold acetone. 4,6-diamidino-2-phenylindole (DAPI, Abcam) was used for nuclear counterstain. Image acquisition was performed using a Leica DMRB microscope (Leica). Images were taken with a digital camera (Spot 32, Diagnostic Instruments).

Figure 8:
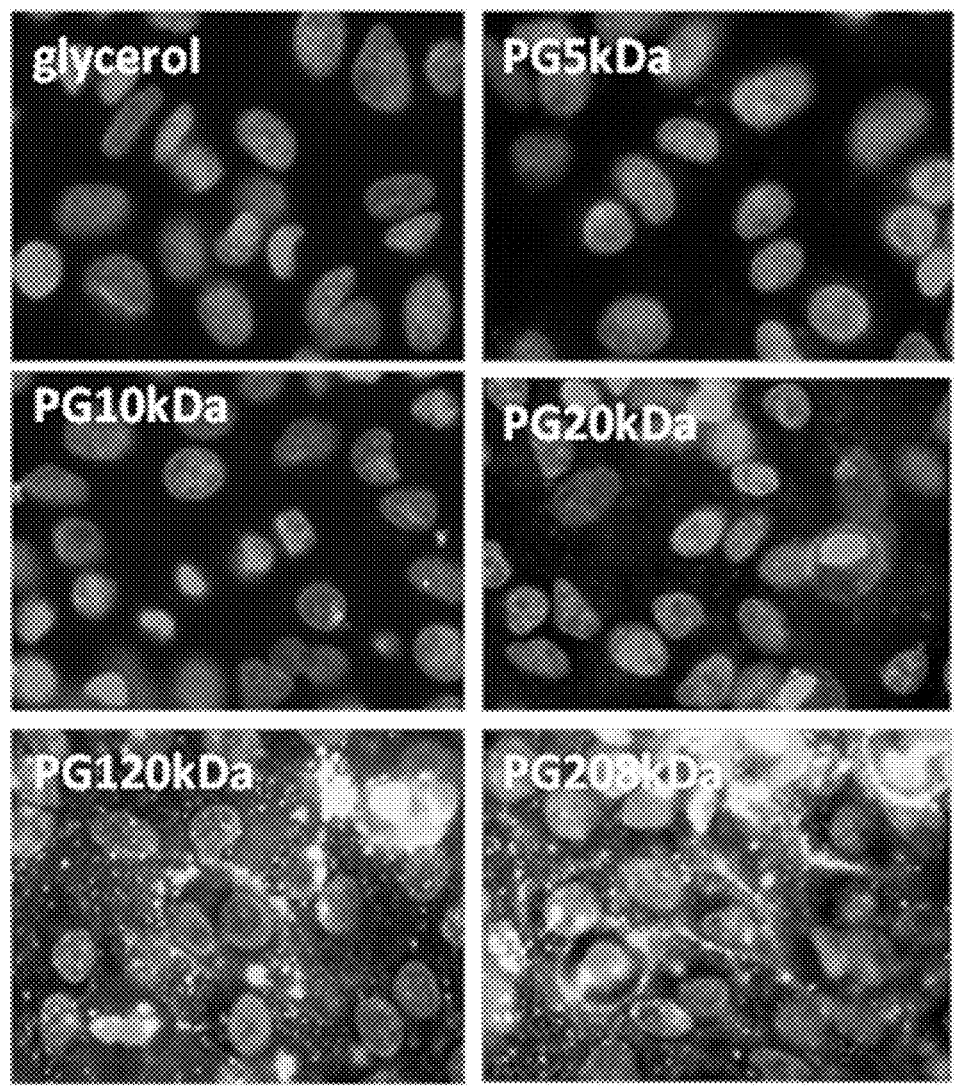
FIG. 8 illustrates the cellular uptake of fluorescent triglycerol or polyglycerol conjugates (ICC dye) of different molecular weights by A549 human lung cancer cells incubated in vitro for 1 hour in a cytochemical staining (nuclear staining with DAPI) (example 7).

There was no cell uptake of polyglycerols with lower molecular weights (up to 20 kDa) or ICC-triglycerol conjugate. Intracellular localization of polyglycerols with high molecular weights (120 or 208 kDa) was clearly demonstrated. Results are illustrated in FIG. 8.

Example 8

Figure 9:
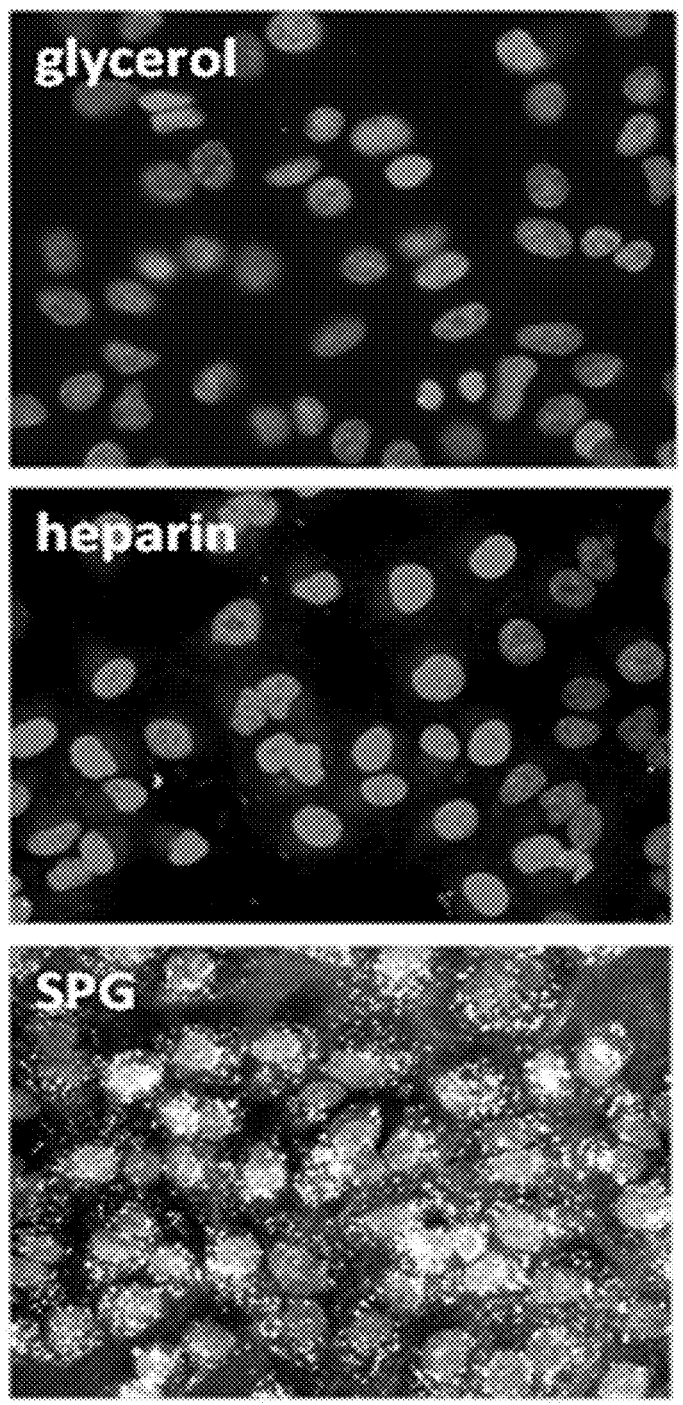
FIG. 9 illustrates the cellular uptake of ICC-triglycerol conjugate and the sulfated macromolecule heparin and sulfated polyglycerol (example 3c) by A549 human lung cancer cells incubated in vitro for 4 hours in a cytochemical staining (nuclear staining with DAPI). Only sulfated polyglycerol (SPG) localizes in the cell (example 8).

Incubation of Human Lung Tumor A549 Cells with Fluorescent Polyanionic Macromolecules and In Vitro Fluorescence Imaging The epithelial human lung cancer cell line was routinely propagated and treated in 24-well culture plates as described in example 7. Cells were cultured with medium containing $10^{-6}$M heparin-ICC conjugate or sulfated polyglycerol-ICC conjugate (example 3c) or $10^{-6}$ M ICC-triglycerol conjugate (Angew Chem Int Ed Engl. 48: 7540, 2009) as control for 4 hours at 37° C. Afterwards, cells were fixed with cold acetone. 4,6-diamidino-2-phenylindole (DAPI, Abcam) was used for nuclear counterstain. Image acquisition was performed using a Leica DMRB microscope (Leica). Images were taken with a digital camera (Spot 32, Diagnostic Instruments). There was no cell uptake of heparin or glycerol-ICC conjugates, whereas sulphated polyglycerol-ICC was demonstrated in the cytoplasm of A549 cells. Results are illustrated in FIG. 9.

Example 9

Figure 10:
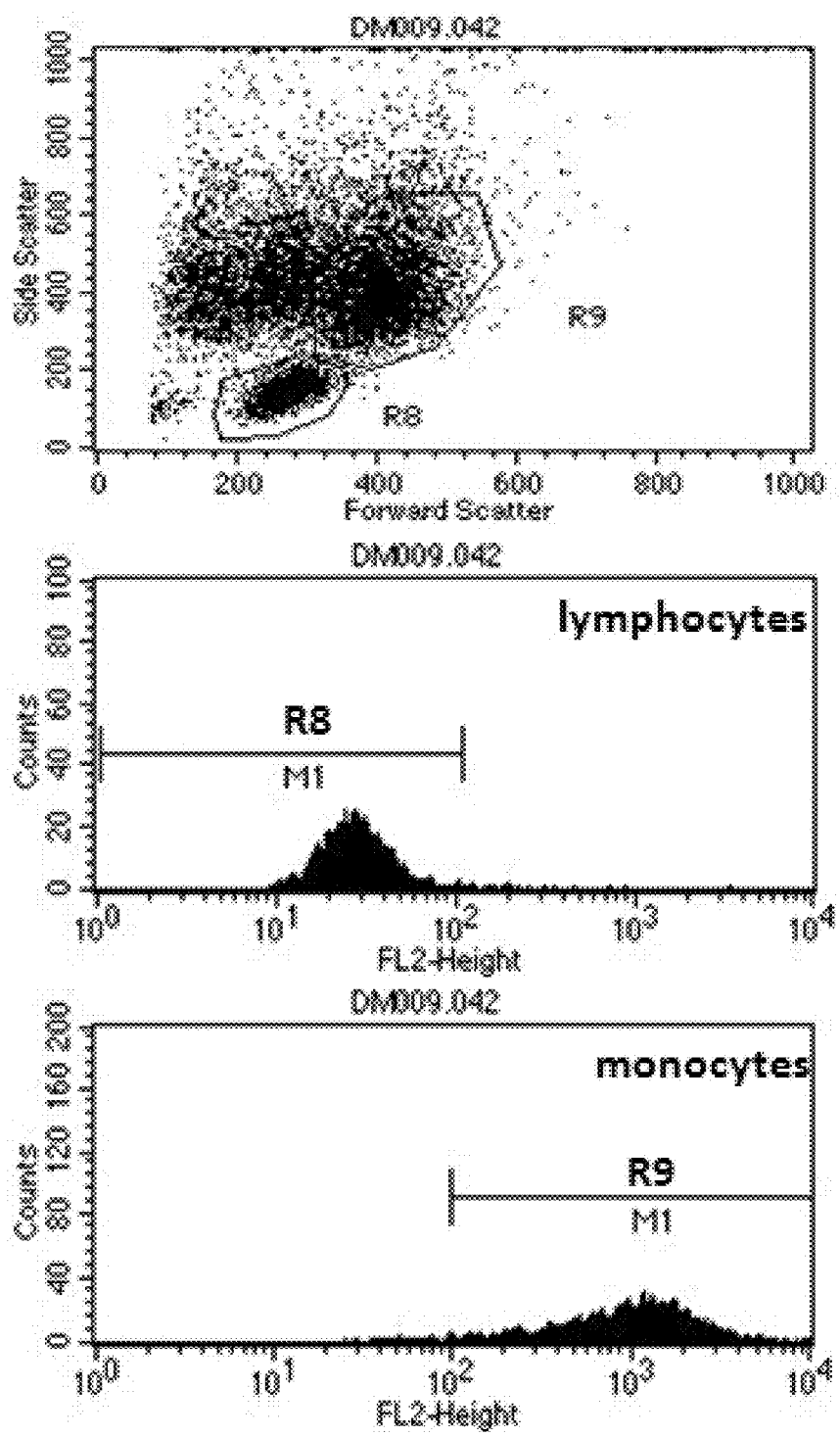
FIG. 10 shows by flow cytometric analysis (FACS) that monocytes can take up sulfated polyglycerol (compound of example 3c) in very high quantities, whereas lymphocytes show only marginal uptake (example 9).

Flow Cytometric Analysis of Isolated Human Peripheral Blood Mononuclear Cells Incubated with ICC-Conjugated Sulfated Polyglycerol Cells from the mononuclear fraction of human blood were isolated by differential centrifugation on Ficoll-Hypaque, and subsequent washing with RPMI containing 10% fetal calf serum (PAN Biotech). $2\times10^5$ cells/ml cells were cultured in 24-well-plates with RPMI culture medium or medium containing $10^{-6}$ M sulfated polyglycerol-ICC conjugate (example 3c) or $10^{-6}$M ICC-triglycerol conjugate (Angew Chem Int Ed Engl. 48: 7540, 2009) as control for 4 hours. Thereafter, cells were washed with PBS and detached with 200 μl/well accutase (PAA) and washed two times with PBS. Cells were fixed with 500 μl 3% paraformaldehyde for 10 min at 4° C., stopped with 2 ml PBS and centrifuged with 250 g, for 10 min at 4° C. Supernatants were removed and cells were suspended in 200 μl PBS with 0.5% bovine serum albumin (Roth). Fixed cells were kept at 4° C. until analysis in a FACS Calibur analysis instrument (Becton-Dickinson). Monocytes or lymphocytes were identified by analyzing of size and granularity of the cells (forward/side-scatter) and the uptake of sulfated polyglycerol-ICC conjugate was quantified. In monocytes about hundertfold higher quantity of sulfated polyglycerol was detected as in lymphocytes. Results are illustrated in FIG. 10.

Example 10

Inhibition of TGF-β-1 Release

Figure 11:
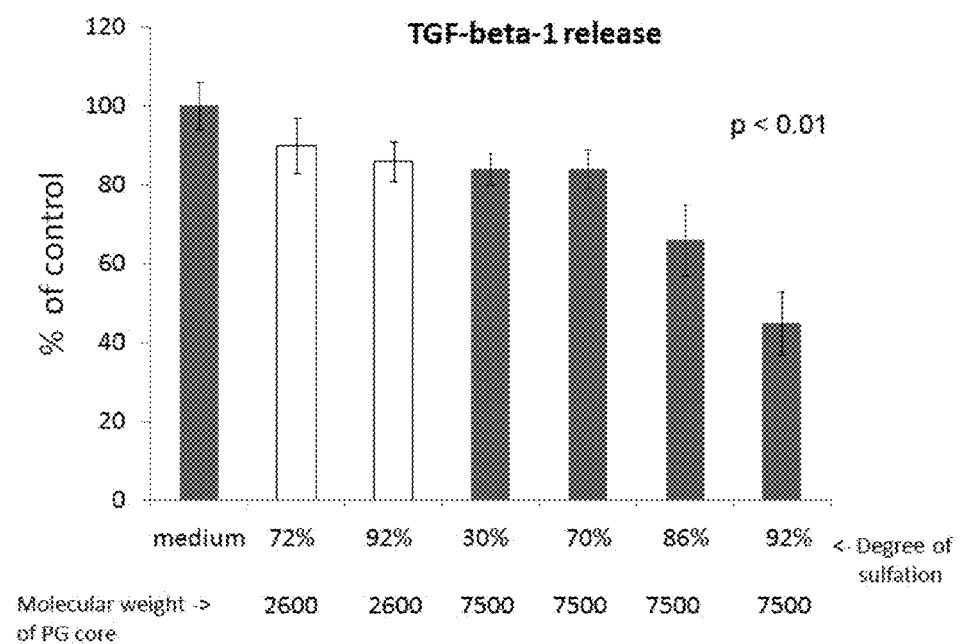
FIG. 11 demonstrates that sulfated polyglycerols induce a statistically significant inhibition of TGF-beta-1 release from CASKI cells. Cells were treated for 48 hours and TGF-beta-1 detected in culture supernatants by ELISA (example 10).

CASKI cells were cultured as follows: DEMEM medium, with 10% fetal calf serum (FCS), 2% glutamine and penicillin/streptomycin (all from PAN Biotech) added. Cells were seeded into medium at $1\times10^5$ cells/ml, cultured at 37° C. with 5% $CO_2$, and split 1:5 two times a week. Sulfated polyglycerols with different degrees of sulfation (30%, 70%, 86% or 92% of sulfation) or different molecular weight of polyglycerol core (2600 or 7500 Da) were applied for 48 hours to CASKI cells at a concentration of $10^{-8}$ M. Culture with medium alone was used as control. The culture supernatants were withdrawn centrifuged and stored at −20° C. The content of TGF-beta-1 in the culture supernatants was detected using a commercially available ELISA-kit (eBioscience Inc). Results are illustrated in FIG. 11.

Example 11

NF-kappaB Binding of Sulfated Polyglycerols Using SPR Technology

Figure 12:
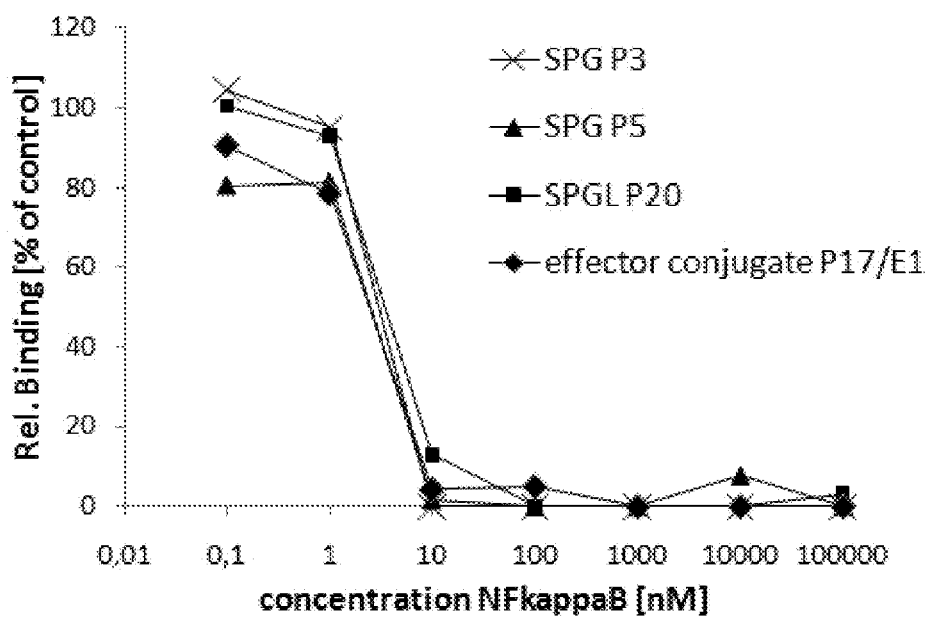
FIG. 12 shows that sulfated polyglycerols (SPG), sulfated polyglycerols with linkers (SPGL), and conjugates with effector molecules bind in high affinity to intracellular transcription factor NF-kappaB measured by SPR/Biacore. Binding affinities increase with increasing degree of sulfation and molecular weight shown by decreasing $IC_{50}$ values. Linkers and effector molecules do not hamper binding affinity (example 11).
Figure 12:
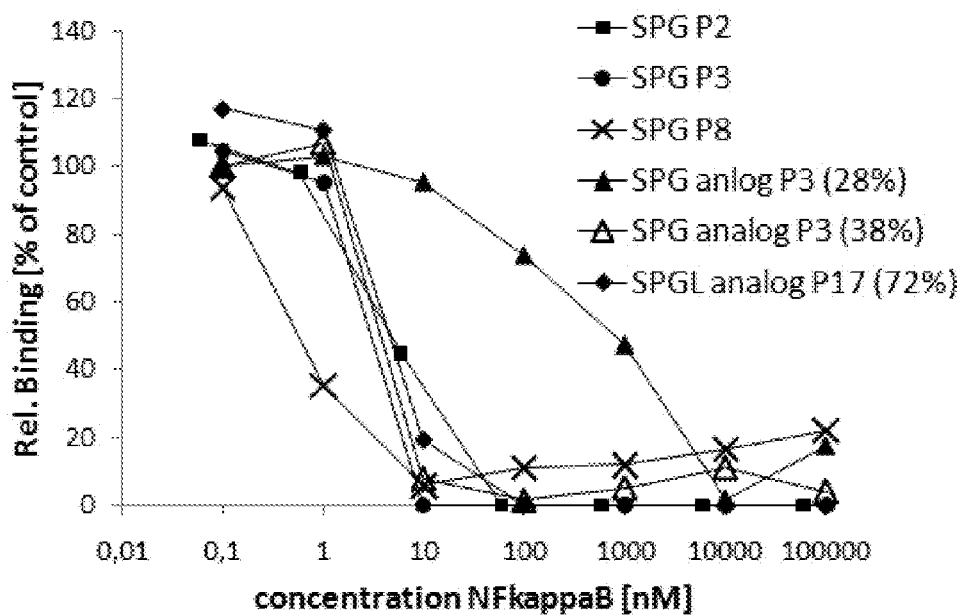

Experiments were performed on a BIACORE X instrument (Biacore AB, Uppsala, Sweden) at 25° C. Ligand immobilization involved the use of HBS-EP buffer (Biacore AB), consisting of 10 mM HEPES, pH 7.4, 150 mM NaCl, 3 mM EDTA, and 0.005% Surfactant P20. HBS-EP buffer was used as well as running buffer during the assay. Biotinylated single strands of the κB DNA sequence motif (bold) (5'-biotin-AGTTGAGGGGACTTTCCCAGGC-3' (forward; biotin-SEQ ID NO:3) and 5'-biotin-GCCTGGGAAAGTCCCCT-CAACT-3' (reverse; biotin-SEQ ID NO:4) were purchased from metabion international AG (Martinsried, Germany). 30 μl of both single strand solutions (each at a concentration of 100 μM) were mixed, heated for 5 mM at 80° C. and cooled down slowly to room temperature to enable perfect hybridization. Subsequently, 60 μl of HBS-EP buffer was added to the sample and the biotinylated probe was immobilized on a streptavidin functionalized sensor chip SA (Biacore AB). For reference purposes, the second lane of the same chip remained empty. For a better performance, the sensor chip was initially conditioned with three consecutive 1 min injections of 1 M NaCl in 50 mM NaOH before starting immobilization. The chip was loaded with the kappaB DNA sequence motif to a baseline shift of 1300 resonance units (RU). The immobilization procedure was followed by several washes with running buffer to equilibrate the chip surface. Recombinant NF-kappaB p50 protein was purchased from Active Motif (Carlsbad, Calif., USA). The final working concentration of NF-kappaB protein was approximately 28.6 nM (molarity is based on a molecular weight of the NF-kappaB monomer; 50,000 Da). Before loading, each sample was incubated with the respective sulfated polyglycerol compound (see table 5) for 18 min at room temperature at final inhibitor concentrations of 0 nM, 0.1 nM, 1 nM, 10 nM, 100 nM, 1 µM, 10 µM, or 100 µM. The samples were injected over the reference and the ligand (kappaB DNA oligonucleotides) lane at a flow rate of 20 µl/min. Each measurement cycle consisted of a 105 s period for injecting the sample (association phase), a 180 s undisturbed dissociation phase, and a wash of the flow system with 1 M NaCl. For data evaluation, the reference lane data were subtracted from ligand (kappaB DNA sequence) lane data. Responses of the sample injections were extracted between report points set at the start of the injection (0 sec) and at the end of the dissociation phase (285 sec). The final response values were used for curve creation. Each data point represents the mean value (±SEM) of two measurements. Binding curves are depicted in FIG. 12. $IC_{50}$ values are listed in table 5. Binding affinities increase with increasing degree of sulfation and molecular weight shown by decreasing $IC_{50}$ values. Linkers and effector molecules do not hamper binding affinity. Assembly of sulfates on dendrons at a number of only 16 sulfates does not exhibit sufficient binding affinity (G3.0-dendron/E1).

TABLE 5

$IC_{50}$ values of sulfated polyglycerols, sulfated polyglycerols with linkers, and conjugates with effector molecules (examples 1, 2, 3):

| Compound type | example | IC50 value |
|---|---|---|
| sulfated polyglycerol (P3) | 1 b | 3.5 nM |
| sulfated polyglycerol (P10) | 1 b | 3.0 nM |
| sulfated polyglycerol (P2) | 1 b | 5.0 nM |
| sulfated polyglycerol (P8) | 1 b | 0.7 nM |
| sulfated polyglycerol analog to P3 with 38% sulfation | 1 b | 4.5 nM |
| sulfated polyglycerol analog to P3 with 28% sulfation | 1 b | 1000 nM |
| sulfated polyglycerol with linker (P20) | 2 d | 3.0 nM |
| sulfated polyglycerol with linker analog to P17 with 72% sulfation | 2 d | 5.5 nM |
| sulfated polyglycerol - cyanine dye conjugate (P26/E2) | 3b | 3.0 nM |
| sulfated polyglycerol - cyanine dye conjugate (G3.0-dendron/E1) | 3 e | 1000 nM |

Example 12

Inhibition of Lung Tumor Cell Growth In Vitro

In order to test potential effects of sulfated polyglycerol on cell growth of lung tumor cells, the human A549 cell line was used. The A549 cell line was routinely propagated as follows DEMEM medium, with 10% fetal calf serum (FCS), 2% glutamine and penicillin/streptomycin (all from PAN Biotech) added. Cells were seeded into medium at $1 \times 10^5$ cells/ml, cultured at 37° C. with 5% $CO_2$, and split 1:5 two times a week.

Analysis of cell proliferation was performed with cells cultured in 24-well-plates. $2 \times 10^5$ cells/ml were incubated in 1 ml culture medium containing increasing concentrations of test substances. After 2 days of culture, cell number, viability and cell diameter as one parameter of apoptotic processes were analyzed in a cell counter and analyzer system (CASY®, Schärfe Systems). In addition, drug influence was assessed in vitro using the MTT assay (cellular reduction of 3-(4,5-dimethylthiazol-2-yl)-2,5-diphenyltetrazolium bromide) as a test for metabolic activity of the cells. Briefly, $1 \times 10^4$ cells per well were plated in 96-well plates in 100 µl culture medium containing increasing concentration of the test substance. After 2 days of culture, 10 µl MTT (5 mg/ml in PBS, obtained from Sigma) was added to each well and the plates were incubated for 4 h. The resulting formazan product was dissolved with acid isopropanol and the absorbance at a wavelength of 570 nm (Ex570) was read on a Microplate Spectrophotometer (Anthos htII, Microsystems).

Figure 13:
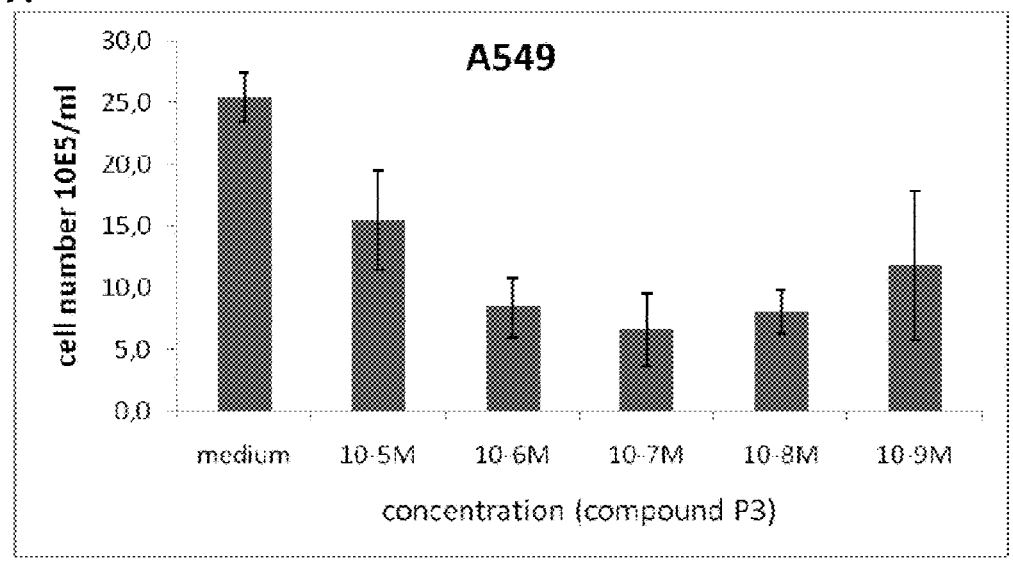
FIG. 13 highlights that sulfated polyglycerol induces a statistically significant and biologically relevant inhibition of lung A549 tumor cell growth (FIG. 13A) and metabolic activity (FIG. 13B). A549 cells were cultured for 7 days with sulfated polyglycerol and cell number and metabolic activity were detected. Tumor cell number (A) and results of MTT-Test (B) after 7 days of culture is shown (MW+/−SD) (example 12).
Figure 13:
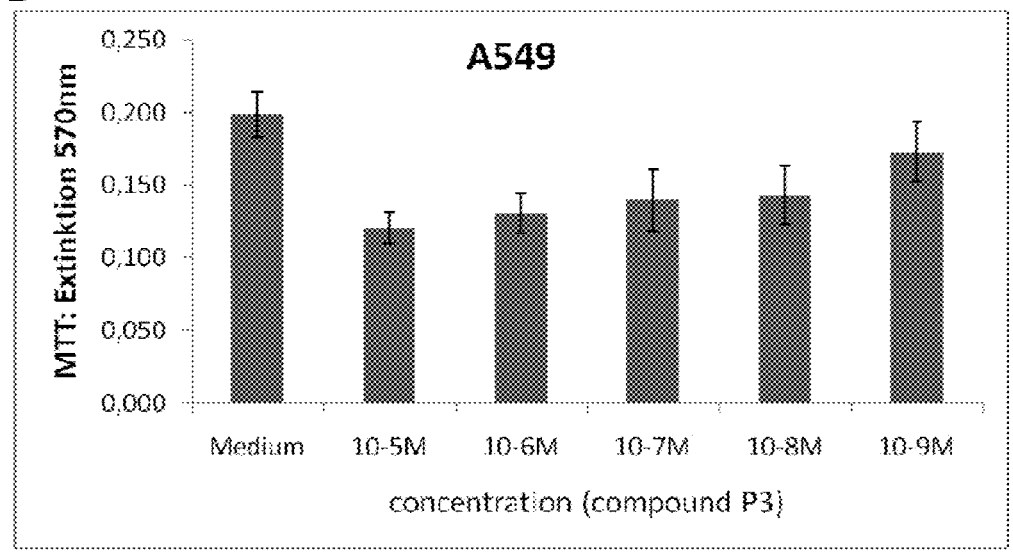

Sulfated polyglycerol (compound P3) was applied for 48 hours to A549 cells at a concentration of $10^{-5}$M to $10^{-9}$M. Culture with medium alone was used as control. Results are illustrated in FIG. 13.

Example 13

Efficacy in a Tumor Mouse Model In Vivo

Figure 14:
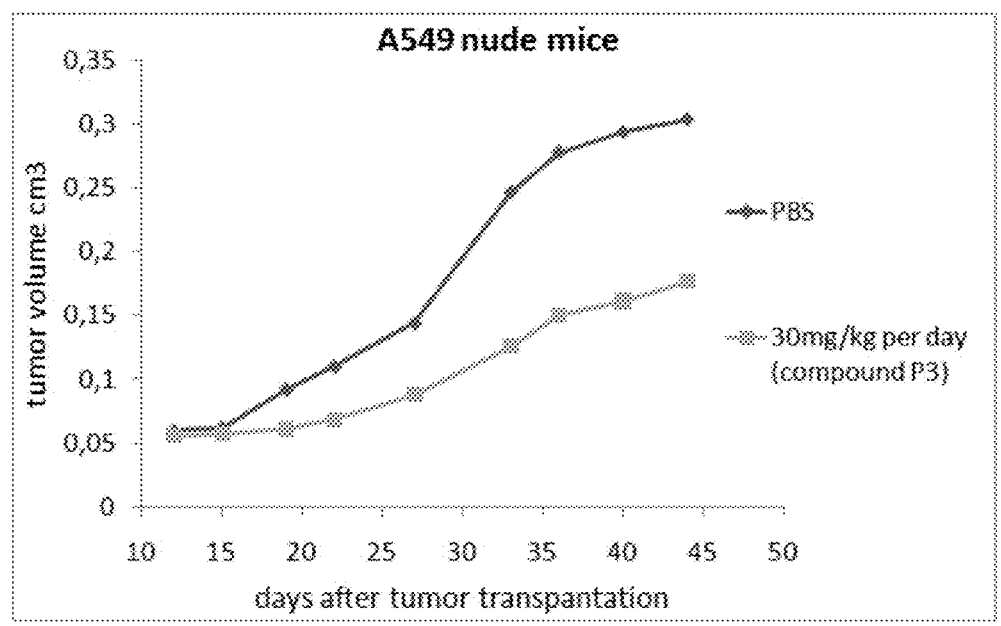
FIG. 14 shows the time course of the tumor volume of nude mice (A549 lung cancer model) treated sulfated polyglycerol or PBS (control). Sulfated polyglycerol (compound P3) in daily doses of 30 mg/kg body weight inhibits the tumor growth indicating a strong therapeutic effect after 45 days of treatment (example 13).

To test whether sulfated polyglycerol is effective in suppression of tumor growth in vivo, a well-established nude mouse model of lung cancer was used. Human non-small lung cancer cells A549 ($0.7 \times 10^7$ cells/mouse) were injected s.c. into the flanks of athymic male NMRI nu/nu mice (Taconic Europe). Daily treatment with 100 µl PBS or 30 mg/kg b.w. sulfated polyglycerol (compound P3) in 100 µl PBS s.c. was performed at days 12-16, 19-23 and 26-30 after cell implantation. Tumor volumes were determined on 10 point of time between day 12 and 44 after cell implantation. Tumor size was measured with a caliper, and the volume was estimated according to the formula: volume ($cm^3$)_ ½(L_W2), where L and W are the length (cm) and width (cm) of the transplanted tumor. Results are illustrated in FIG. 14. In addition, no signs of toxicity and adverse events due to drug treatment were identified over the entire time of treatment of the mice.

Example 14

Efficacy in the Collagen-Induced Rheumatoid Arthritis-Model

Figure 15:
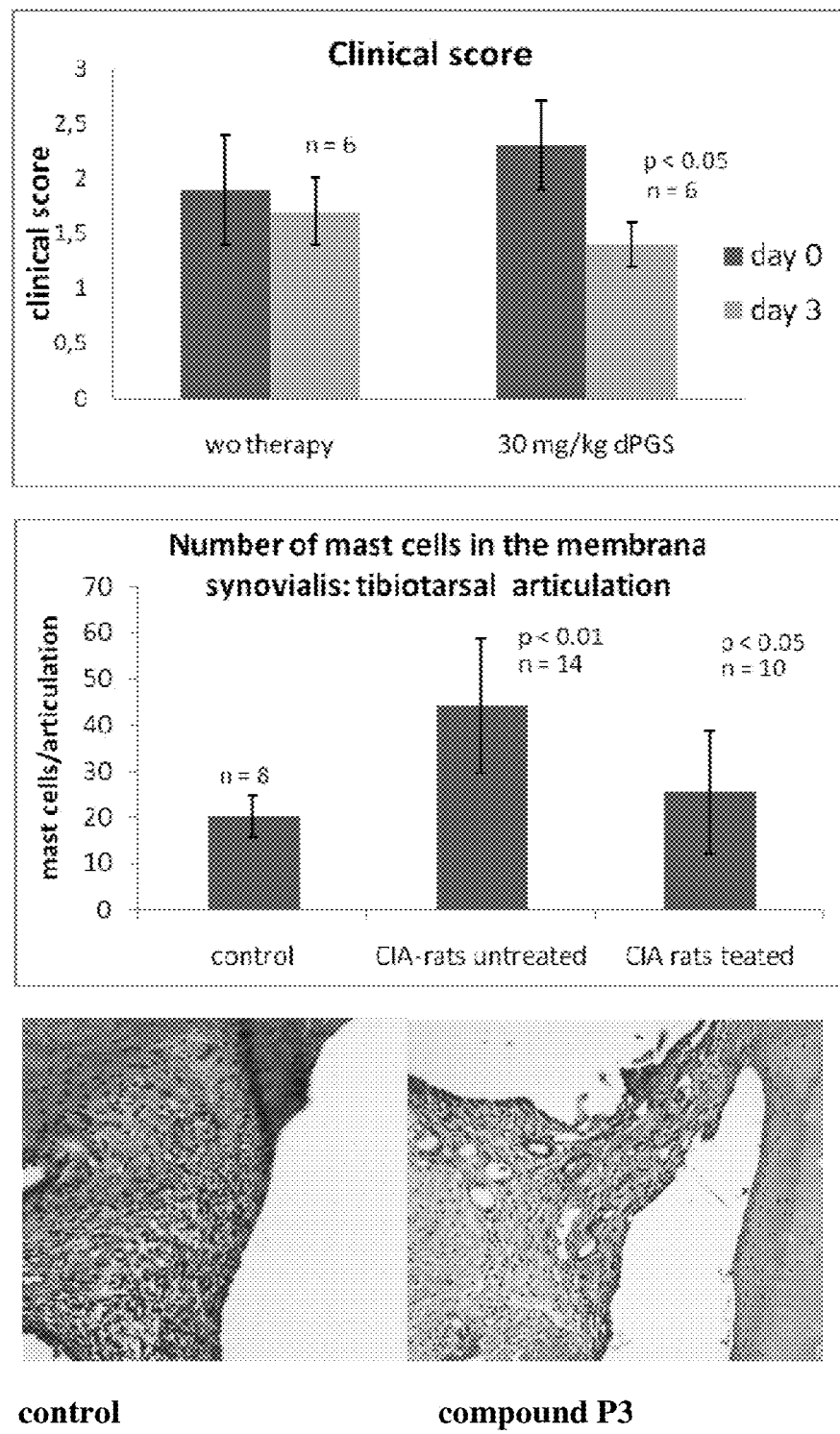
FIG. 15 verifies the effect of daily subcutaneous treatments of rats with collagen induced arthritis and healthy controls with sulfated polyglycerol. The clinical score, number of mast cells and inflammatory infiltrate in the membrane synovialis are influenced after treatment with sulfated polyglycerol in daily doses of 30 mg/kg indicating significant therapeutic outcome (example 14).

To test whether sulfated polyglycerol are effective in suppression of rheumatoid arthritis, the experimental collagen-induced rheumatoid arthritis (CIA) was induced in rats. CIA was induced by immunization of female Lewis rats with an emulsion of bovine type II collagen and incomplete Freund's adjuvant (DIFCO Laboratories). Paw inflammation was assessed by the increase in paw volume after two weeks. Rats were monitored daily for clinical signs of disease and assigned disease scores from 0 to 3. For in vivo treatment, 30 mg/kg body weight of sulfated polyglycerol (compound P3) in 200 µl PBS was administered daily by s.c. injection to control and CIA-rats from day 14 until day 16 after immunization. Lesions of bone and cartilage and inflammatory infiltrate were assessed on the basis of histological change in paraffin slices of knee joint. Mast cells were stained with toluidin blue (Sigma) in 0.5N HCL (Roth) overnight and counted in the synovium. Results are illustrated in FIG. 15. In addition, no signs of toxicity and adverse events were identified over the entire time of treatment of the mice.

Example 15

Efficacy in the Experimental EAE-Model

To test whether sulfated polyglycerols are effective in suppression of experimental multiple sclerosis, the experimental autoimmune encephalitis (EAE) was induced in mice. EAE was induced in female SJL mice 8 to 12 weeks of age by immunization of mice s.c. with 100 µg PLP in 100 µl PBS and 100 µl CFA. CFA was prepared by mixing of incomplete Freund's adjuvant (DIFCO Laboratories) with 8 mg/ml of *Mycobacterium tuberculosis* H37RA (desiccated; DIFCO Laboratories). At the time of immunization and 2 days later, mice were injected i.v. with 200 ng of pertussis toxin (List Biological Laboratories) in 100 µl PBS. Mice were monitored daily for clinical signs of disease and assigned disease scores from 0 to 5 based on the severity of EAE as follows: 0, no disease; 1, limp tail; 2, hind limb weakness; 3, hind limb paralysis; 4, hind limb and forelimb paralysis; 5, morbidity and death.

For in vivo treatment, sulfated polyglycerol (compound P3) was administered daily by s.c. injection to PLP-immunized mice from day 2 until day 20. The mice were monitored daily for clinical signs of disease. Table 6 demonstrates the therapeutic effect of sulfated polyglycerol in daily sc. doses of 30 mg/kg. Whereas the control animals exhibited at day 10 and day 20 after immunization a clinical score of 3.1 and 2.3 respectively, sulfated polyglycerol in daily doses of 30 mg/kg body weight decreased the clinical score to 1.7 and 1.1, respectively. In addition, no signs of toxicity and adverse events due to drug treatment were identified over the entire time of treatment of the mice.

TABLE 6

Effect of sulfated polyglycerol (P3) on the clinical score in the EAE mouse model

| | Clinical Score Day 10 | Clinical Score Day 20 |
|---|---|---|
| Control group | 3.1 | 2.3 |
| Treatment group | 1.7 | 1.1 |

Example 16

Efficacy in the Experimental Subacute Sepsis Model

Sulfated polyglycerols were tested in a model of subacute sepsis in female NMRI mice. Sepsis was induced by a single intraperitoneal injection of LPS in a single dose of 0.2 mg/kg. Negative controls received a single injection of saline. Sulfated polyglycerol (compound P3) was applied in a single dose of 15 mg/kg by subcutaneous injection 30 minutes before LPS (Sigma Aldrich) application. The serum level of the complement protein C5a (Alpco Diagnostics) was measured as an indicator of non-lethal sepsis. The measurement was performed 2 hours or 6 hours after application of LPS. Compared to negative controls LPS induced a stimulation of serum C5a to 245%. Sulfated polyglycerol in a single dose of 15 mg/kg induced a strong inhibition of the LPS-mediated stimulation to 105% of the level of negative controls. The inhibition was also evident 6 hours after application of LPS.

TABLE 7

Effect of sulfated polyglycerol on the LPS-induced sepsis induction in mice

| | Serum level of C5a 2 hours after LPS induction compared to negative controls | Serum level of C5a 6 hours after LPS induction compared to negative controls |
|---|---|---|
| Negative controls - no LPS induction | 100% | 100% |
| Positive controls - LPS induction | 245% | 185% |
| Sulfated polyglycerol (P3) treatment - LPS induction | 105% | 110% |

Example 17

Figure 16:
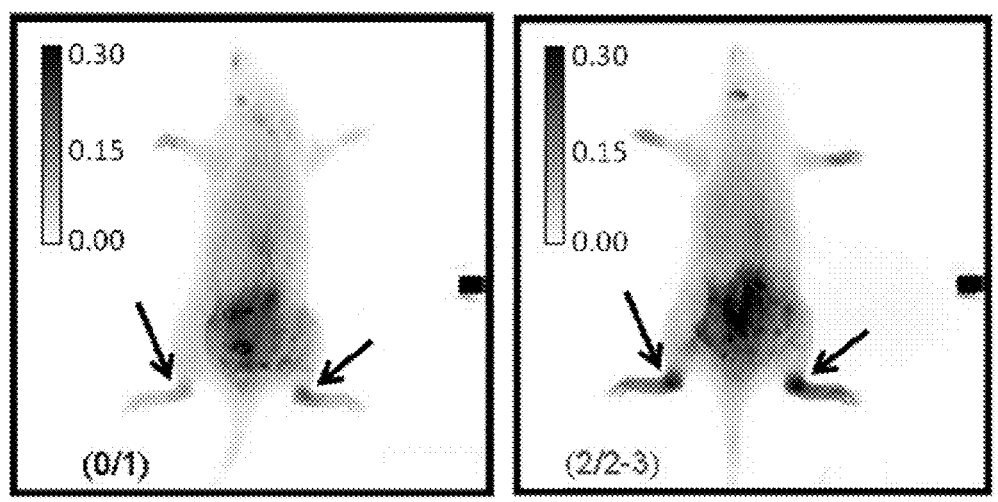
FIG. 16 depicts fluorescence images of anaesthetized rats with collagen induced rheumatoid arthritis with fast and high uptake of sulfated polyglycerol conjugate with cyanine dye (compound P26/E2, example 3b) and fluorescence contrast in arthritic joints (10 min) increasing with disease activity (low to high with score 1 to 3). Arrows indicate arthritic joints with high fluorescence contrast (example 17).

Uptake of Sulfated Polyglycerol in the Experimental Model of Rheumatoid Arthritis by In Vivo Fluorescence Imaging Effector conjugate P26/E2 (example 3b) was dissolved in 0.9% NaCl (concentration: 1 mg/ml) and injected into the tail vain of rats with collagen-induced rheumatoid arthritis (animal model as described in example 14; dose: 2 mg/kg). A planar fluorescence imaging set-up consisting of a laser unit (excitation wavelength 760 nm) and a CCD camera with long-pass filter (observation >780 nm) was used according to J. Biomed. Optics 10, 41205 (2005). Fluorescence images of anaesthetized rats were taken at 10 min, 30 min, 1 h, 6 h and 24 h post injection. Results are depicted in FIG. 16 showing fast and high uptake and fluorescence contrast in arthritic joints (10 min) lasting up to 24 h (data not depicted), whereas healthy joints do not exhibit enhanced fluorescence. Arrows indicate arthritic joints of increasing disease progression (disease scores 1, 2 and 3) with fluorescence contrasts increasing with the score, thus demonstrating the ability of the conjugate to monitor disease activity.

Example 18

Figure 17:
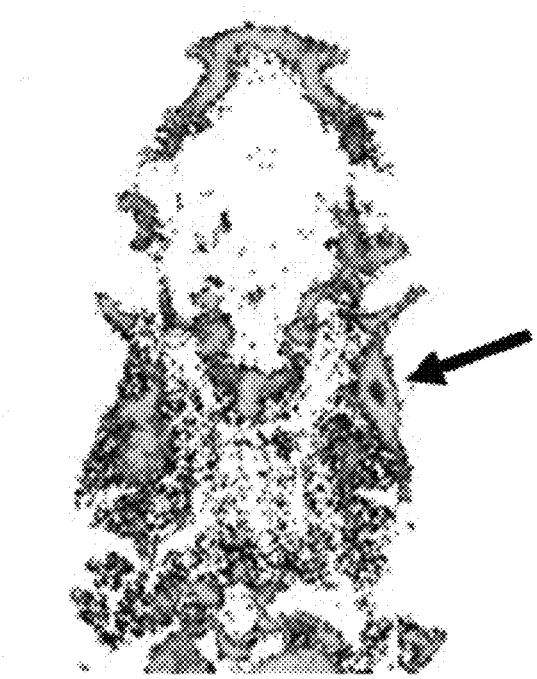
FIG. 17 shows a PET image of a sulfated polyglycerol conjugate with DOTA radiolabeled with $^{64}Cu$ (compound P17/E13, example 4a) in a mouse model for skin inflammation (contact hypersensitivity). Image of anaesthetized mice showing a high contrast in the inflamed ear tissue. The arrow indicates the inflamed area (example 18).

Uptake of Sulfated Polyglycerol Conjugate with DOTA Conjugate in the Experimental Model of Dermatitis (Mouse) by In Vivo PET Imaging C57Bl/6 mice (female, 8 weeks) were sensitized to TNCB by topical application of 450 µg TNCB onto the abdominal skin. After five days, mice were challenged by topical application of 45 µg TNCB onto the right ear. Effector conjugate P17/E13 example 4a was labeled with Cu-64 according to methods published in the literature (generation of Cu-64 in the form of $CuCl_2$ solution: Appl. Radiat Isot. 2007, 65, 1115). Labeling was performed in Acetate buffer (pH 5) for 1 h at 37° C. (100 MBq) using 0.1 mg conjugate. Radiochemical purity was determined by HPLC and radio-TLC. Radiochemical yield was 90%. The Cu-64-labeled HSPG DOTA conjugate was obtained as solution in phosphate buffer pH7.4 after SEC purification. 100 µCi were injected into the tail vain of mice. High resolution 10 min PET images were repeatedly acquired with a clinical PET scanner. Images of anaesthetized mice were taken at 30 min post injection of the Cu-64-labeled HSPG DOTA conjugate. Results are depicted in FIG. 17 showing fast and high uptake in areas with inflammation (inflamed tissue at the mice ear) as indicated by the arrow.

Example 19

Increase of Cytotoxic Effects of Cytostatic Drugs on Tumor Cells by Cytostatic Effector Conjugated to Sulfated Polyglycerol In order to test potential effects of conjugation with sulfated polyglycerol on cytotoxic effects of cytostatic drugs, the human A549 cell line was used. The A549 cell line was routinely propagated as follows DEMEM medium, with 10% fetal calf serum (FCS), 2% glutamine and penicillin/streptomycin (all from PAN Biotech) added. Cells were seeded into medium at $1\times10^5$ cells/ml, cultured at 37° C. with 5% $CO_2$, and split 1:5 two times a week.

Analysis of cell proliferation was performed with cells cultured in 24-well-plates. $2\times10^5$ cells/ml were incubated in 1 ml culture medium containing increasing concentrations of test substances. After 24 hours of culture, medium with test substances was removed and substituted with normal culture medium. After other 24 hours of culture, cell number, viability and cell diameter as one parameter of apoptotic processes were analyzed in a cell counter and analyzer system (CASY®, Schärfe Systems). In addition, drug influence was assessed in vitro using the MTT assay (cellular reduction of 3-(4,5-dimethylthiazol-2-yl)-2,5-diphenyltetrazolium bromide) as a test for metabolic activity of the cells. Briefly, $1\times10^4$ cells per well were plated in 96-well plates in 100 µl culture medium containing increasing concentration of the test substance (paclitaxel conjugate of example 6b). After 2 days of culture, 10 µl MTT (5 mg/ml in PBS, obtained from Sigma) was added to each well and the plates were incubated for 4 h. The resulting formazan product was dissolved with acid isopropanol and the absorbance at a wavelength of 570 nm (Ex570) was read on a Microplate Spectrophotometer (Anthos htII, Microsystems). Paclitaxel (taxol) was applied at A549 cells at a concentration of $10^{-7}$M and test substance at concentrations of $10^{-7}$ M to $10^{10}$ M. Culture with medium alone was used as control.

Figure 18:
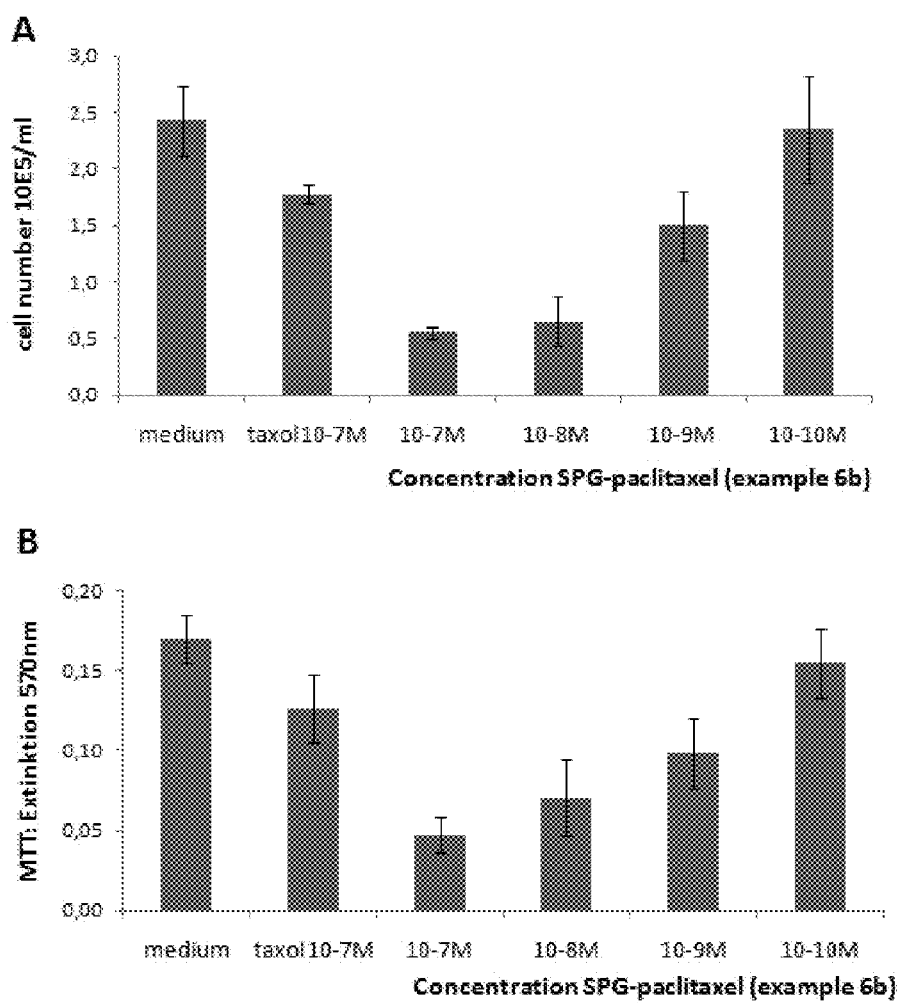
FIG. 18 demonstrates that sulfated polyglycerol conjugate with paclitaxel (taxol) (compound of example 6b) increases the inhibition of cell growth and metabolic activity of lung tumor cells A549 compared to paclitaxel (taxol) without conjugation. Tumor cell number (FIG. 18A) and results of MTT-Test (FIG. 18B) after 48 hours of culture is shown (MW+/−SD, n=4) (example 19).

Results are illustrated in FIG. 18 showing superior efficacy at comparable concentration of $10^{-7}$M, as well as cytotoxic effects at 1/100 lower concentrations.

Example 20

Figure 19:
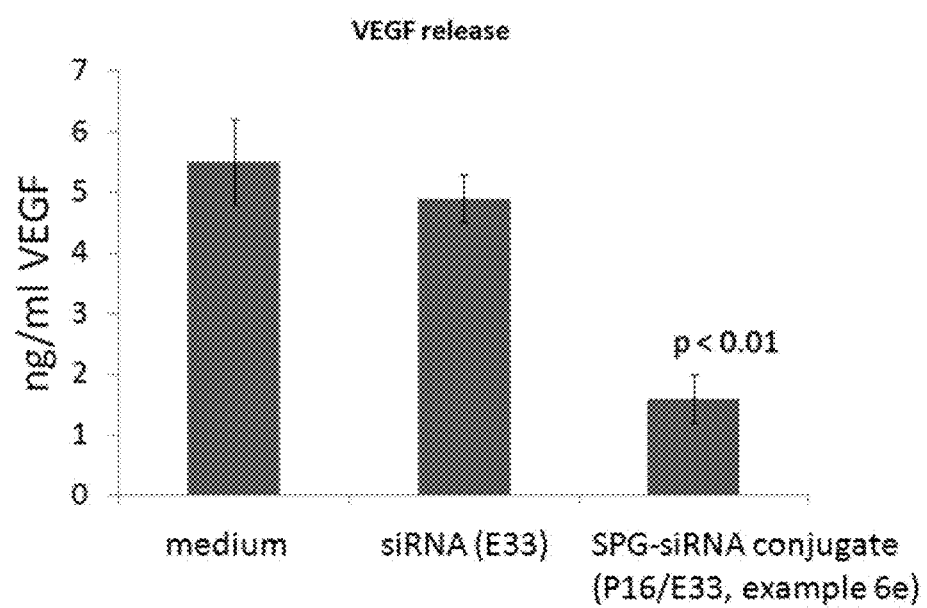
FIG. 19 shows VEGF production in A549 lung cancer cell lines after incubation with sulfated polyglycerol (SPG) conjugated to VEGF-siRNA (example 6e) or VEGF-siRNA alone. VEGF protein was measured by ELISA in 48 h conditioned cell culture medium. Each bar is the mean±SEM of three determinations from three independent experiments (example 20).

Inhibition of VEGF Expression by Sulfated Polyglycerol Conjugated to Effector VEGF-siRNA The lung cancer cell line A549 was grown as described in example 11. To collect supernatants for VEGF detection, cells were seeded at $1\times10^6$ cells/ml in a 24-well culture plate for 24 hours. Thereafter, the VEGF-siRNA or VEGF-siRNA coupled with sulfated polyglycerol (conjugate P16/E33, example 6e) were used to incubate the cells without addition of other transfection reagents. Four hours after transfection, culture medium was replaced by fresh medium with 10% FCS. After further 48 h, the culture supernatants were collected for ELISA. The content of VEGF in the supernatants was detected using a commercially available ELISA-kit (Quantikine, R&D Systems). Results are illustrated in FIG. 19 showing VEGF production in A549 lung cancer cell lines after incubation with the test substances. VEGF protein was measured by ELISA in 48 h conditioned cell culture medium. Each bar is the mean±SEM of three determinations from three independent experiments.

Example 21

Test of Aggregation of Solutions of Sulfated Polyglycerol in Buffer

Figure 21:
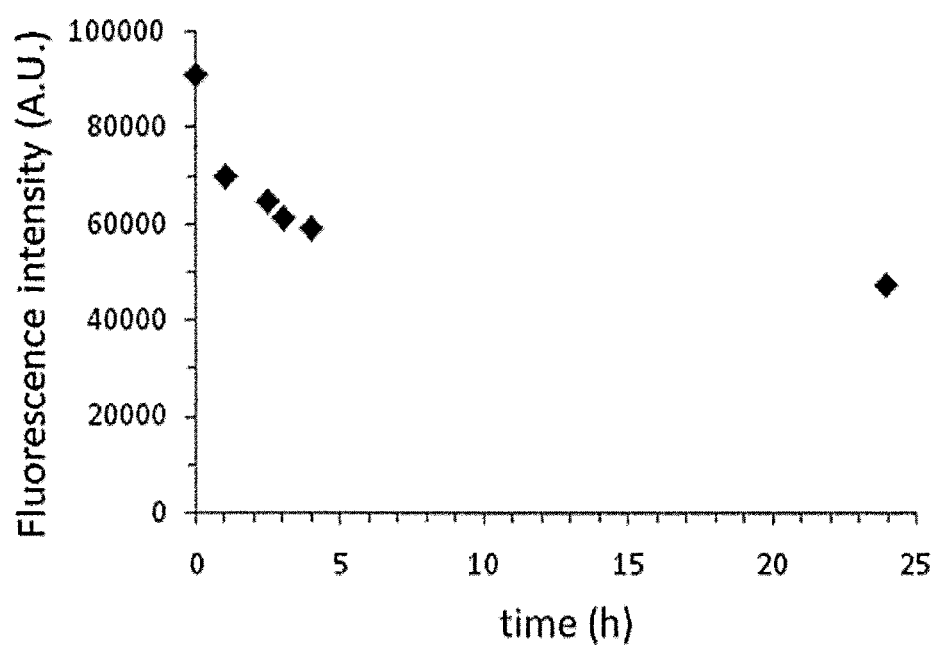
FIG. 21 illustrates the decrease of fluorescence of sulfated polyglycerol conjugate with cyanine dye (compound P17/E1, example 3c) in 0.9% NaCl due to aggregation.

A solution of sulfated polyglycerol conjugated to cyanine dye (compound P17/E1) in 0.9% NaCl (saline) was prepared at a concentration of 0.1 µM. Fluorescence intensity of the solution was determined (excitation 760 nm, detection >780 nm) at different storage times at room temperature in the dark (0, 1, 2.5, 3, 4, 24 h). The results are illustrated in FIG. 21 showing a steady decrease of fluorescence due to aggregation in solution. In aqua dest. or methanol no such decay was observed. Dialysis in aqua dest., addition of trehalose (10 mg per mg of sulfated polyglycerol) and lyophilisation yielded a solid material. Resuspension in aqua dest. yielded a fluorescence signal at the initial level.

---

The invention claimed is:

1. A pharmaceutical composition comprising
a pharmaceutically acceptable carrier, and
a conjugate of a sulfated polyol and a therapeutic effector molecule suitable for treating a disease selected from the group consisting of cancer, inflammation, autoimmune disease and fibrosis of the following formula $$P(OSO_3^-M^+)_n(L\text{-}G\text{-}E)_m,$$

wherein
P is a polyol macromolecule wherein a number n of the hydroxyl groups of the polyol macromolecule is substituted by sulfate groups $OSO_3^-M^+$,
n is a number >10,
M is a cationic inorganic or organic counter ion to the anionic sulfate group,
E is a therapeutic effector molecule suitable for treating a disease selected from the group consisting of cancer, inflammation, autoimmune disease and fibrosis,
L is a linker or spacer between P and E,
G is a reactive group suitable for the covalent attachment between L and E, and
m is a number of from 1 to 100.

2. The pharmaceutical composition according to claim 1, wherein the sulfated polyol is a sulfated polyglycerol that is covalently conjugated to the therapeutic effector molecule E.

3. The pharmaceutical composition according to claim 1, which is a waterless formulation.

4. The pharmaceutical composition according to claim 1, which is a waterless formulation comprising a lyophilisate containing a buffer salt and/or at least one cryoprotectant selected from the group consisting of sucrose, mannose and trehalose.

5. A conjugate of a sulfated polyol and a therapeutic effector molecule suitable for treating a disease selected from the group consisting of cancer, inflammation, autoimmune disease and fibrosis of the following formula $$P(OSO_3^-M^+)_n(L\text{-}G\text{-}E)_m$$

wherein
P is a polyol macromolecule wherein a number n of the hydroxyl groups of the polyol is substituted by sulfate groups $OSO_3^-M^+$,
n is a number >10,
M is a cationic inorganic or organic counter ion to the anionic sulfate group,
E is a therapeutic effector molecule suitable for treating a disease selected from the group consisting of cancer, inflammation, autoimmune disease and fibrosis,
L is a linker or spacer between P and E,
G is a reactive group suitable for the covalent attachment between L and E, and
m is a number of 1-100.

6. The conjugate of claim 5, wherein the sulfated polyol is a sulfated polyglycerol that is covalently conjugated to a therapeutic effector molecule E.

7. The conjugate of claim 5, wherein the effector molecule E accounts for less than 50% by weight of the conjugate, and the conjugate has a solubility in water of more than 100 mg/mL.

8. The conjugate according to claim 5, wherein
a) the polyol P is a polymeric polyglycerol composed of repeating units of glycerol of the formula (RO—CH$_2$)$_2$CH—OR on a multifunctional starter molecule which is a polyhydroxy compound having from 1 to 1,000 OH groups, wherein R is H or further glycerol units, and wherein the core has a branching degree of >60% and an average molecular weight of 500 to 20,000 g/mol;
b) a plurality of n OH groups of the glycerol units is substituted with —OSO$_3$H or —OSO$_3^-$M$^+$ groups, n being a number above 10, and the degree of sulfation X is from 30 to 100%, with M$^+$ being a cationic inorganic or organic counter ion;
c) the average molecular weight of the sulfated polyglycerol is from 1,000 to 30,000 g/mol,
d) the linker unit L carries a functional group G and is attached to at least one of the OH groups of the polyglycerol up to maximum number of 100-X % of the OH groups, wherein X is the degree of sulfation, with the functional groups G being able to be conjugated to one or more additional therapeutic effector molecules E,
e) one or more therapeutic effector molecules E being covalently attached to one to up to the maximum number of said functional groups G, the therapeutic effector molecules E being selected from the group consisting of cytostatics, anti-angiogenetic drugs, photosensitizers and siRNAs.

9. The conjugate according to claim 5, wherein L is a linker consisting of a branched or linear C$_{1-20}$-alkyl group in which one or more non-consecutive methylene groups are optionally replaced by a group selected from the group consisting of O, S, NH, C(O)NH, C(O), SO$_2$, SO, aryl, ethene and ethyne, and wherein G is selected from the group consisting of —OH, —OSO$_3$H, —OSO$_3^-$, —NH$_2$, —N$_3$, —COOH, —SH, —SO$_3^-$ and —C≡C.

10. The pharmaceutical composition according to claim 2, which is a waterless formulation.

11. The pharmaceutical composition according to claim 2, which is a waterless formulation comprising a lyophilisate containing a buffer salt and/or at least one cryoprotectant selected from the group consisting of sucrose, mannose and trehalose.

12. The conjugate of claim 6, wherein the effector molecule E accounts for less than 50% by weight of the conjugate, and the conjugate has a solubility in water of more than 100 mg/mL.

13. The conjugate according to claim 6, wherein
a) the polyol P is a polymeric polyglycerol composed of repeating units of glycerol of the formula (RO—CH$_2$)$_2$CH—OR on a multifunctional starter molecule which is a polyhydroxy compound having from 1 to 1,000 OH groups, wherein R is H or further glycerol units, and wherein the core has a branching degree of >60% and an average molecular weight of 500 to 20,000 g/mol;
b) a plurality of n OH groups of the glycerol units is substituted with —OSO$_3$H or —OSO$_3^-$M$^+$ groups, n being a number above 10, and the degree of sulfation X is from 30 to 100%, with M$^+$ being a cationic inorganic or organic counter ion;
c) the average molecular weight of the sulfated polyglycerol is from 1,000 to 30,000 g/mol,
d) the linker unit L carries a functional group G and is attached to at least one of the OH groups of the polyglycerol up to maximum number of 100-X % of the OH groups, wherein X is the degree of sulfation, with the functional groups G being able to be conjugated to one or more additional therapeutic effector molecules E,
e) one or more therapeutic effector molecules E being covalently attached to one to up to the maximum number of said functional groups G, the therapeutic effector molecules E being selected from the group consisting of cytostatics, anti-angiogenetic drugs, photosensitizers and siRNAs.

14. The conjugate according to claim 6, wherein L is a linker consisting of a branched or linear C$_{1-20}$-alkyl group in which one or more non-consecutive methylene groups are optionally replaced by a group selected from the group consisting of O, S, NH, C(O)NH, C(O), SO$_2$, SO, aryl, ethene and ethyne, and wherein G is selected from the group consisting of —OH, —OSO$_3$H, —OSO$_3^-$, —NH$_2$, —N$_3$, —COOH, —SH, —SO$_3^-$ and —C≡C.

15. The pharmaceutical composition according to claim 1, wherein E is a therapeutic effector molecule suitable for treating cancer.

16. A method for delivery of a therapeutic effector molecule into activated or proliferative cells of a subject which comprises administering to said subject the conjugate according to claim 5.

17. A method for delivery of a therapeutic effector molecule into activated or proliferative cells of a subject which comprises administering to said subject the conjugate according to claim 6.

18. The method according to claim 16, wherein multiple administrations with doses of 1 mg/kg to 1000 mg/kg of said conjugate per administration are performed.

19. The pharmaceutical composition according to claim 1, wherein E is a therapeutic effector molecule suitable for treating an autoimmune disease.

20. The pharmaceutical composition according to claim 1, wherein E is a therapeutic effector molecule suitable for treating fibrosis.

21. The pharmaceutical composition according to claim 1, wherein E is a therapeutic effector molecule suitable for treating inflammation.

22. The pharmaceutical composition according to claim 1, wherein E is a therapeutic effector molecule suitable for treating a disease selected from the group consisting of cancer, inflammation, autoimmune disease and fibrosis, which treatment is achieved by intracellular uptake into activated cells or proliferative cells and by inhibiting NF-kappaB and/or AP-1 and/or inhibiting TGF-beta synthesis in said cells.

23. The conjugate according to claim 5, which does not contain any molecules suitable for diagnostics and does not contain any photosensitizers.

24. The pharmaceutical composition according to claim 1, in which the conjugate does not contain any molecules suitable for diagnostics and does not contain any photosensitizers.

* * * * *

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
ggaguacccu gaugagauct t                                                 21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: Description of Combined DNA/RNA Molecule:
      Synthetic oligonucleotide
<220> FEATURE:
<223> OTHER INFORMATION: 3'-hexylaminom

<400> SEQUENCE: 2
gaucucauca ggguacucct t                                             21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-biotin

<400> SEQUENCE: 3
agttgagggg actttcccag gc                                            22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-biotin

<400> SEQUENCE: 4
gcctgggaaa gtcccctcaa ct                                            22
```